US009051555B2

(12) United States Patent (10) Patent No.: US 9,051,555 B2
Noel et al. (45) Date of Patent: Jun. 9, 2015

(54) METHODS AND COMPOSITION FOR ISOPRENOID DIPHOSPHATE SYNTHESIS

(75) Inventors: Joseph P. Noel, San Diego, CA (US); Nikki M. Dellas, La Jolla, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 410 days.

(21) Appl. No.: 13/384,534

(22) PCT Filed: Jul. 19, 2010

(86) PCT No.: PCT/US2010/042472
§ 371 (c)(1),
(2), (4) Date: Mar. 27, 2012

(87) PCT Pub. No.: WO2011/009132
PCT Pub. Date: Jan. 20, 2011

(65) Prior Publication Data
US 2012/0202234 A1 Aug. 9, 2012

Related U.S. Application Data

(60) Provisional application No. 61/226,582, filed on Jul. 17, 2009.

(51) Int. Cl.
*C12N 9/12* (2006.01)
*C12P 9/00* (2006.01)
(52) U.S. Cl.
CPC .............. *C12N 9/1217* (2013.01); *C12P 9/00* (2013.01)
(58) Field of Classification Search
CPC combination set(s) only.
See application file for complete search history.

(56) References Cited

U.S. PATENT DOCUMENTS

2010/0184178 A1* 7/2010 Beck et al. .................... 435/167

OTHER PUBLICATIONS

Altschul, Stephen F. et al., "Gapped BLAST and PSI-BLAST: a new generation of protein database search programs", Nucleic Acids Research 25(17):3389-3402 (1977).
Briozzo, Pierre et al., "Structure of *Escherichia coli* UMP kinase differs from that of other nucleoside monophosphate kinases and sheds new light on enzyme refulation" The Journal of Biological Chemistry 280(27):25533-25540 (2005).
Brunger, Axel T., "Version 1.2 of the crystallography and NMR system", Nature Protocols 2(11):2728-2733 (2007).
Dellas, Nikki et al., "Mutation of archael isopentenyl phosphate kinase highlights mechanism and guides phosphorylation of additional isoprenoid monophosphates", ACS Chemical Biology 5(6):589-601 (2010).
Grochowski, Laura L. et al., "Met6hanocaldococcus jannaschii uses a modified mevalonate pathway for biosynthesis of isopentenyl diphosphate", Journal of Bacteriology 188(9):3192-3198 (2006).
Henikoff, Steven et al., "Amino acid substitution matrices from protein blocks", Proc. Natl. Acad. Sci. USA 89:10915-10919 (1992).
International Preliminary Report on Patentability and Written Opinion dated Jan. 17, 2012 for International PCT Application No. PCT/US2010/042472, 5 pages.
International Search Report and Written Opinion dated Mar. 30, 2011 for International PCT Application No. PCT/US2010/042472, 11 pages.
Jensen, Kristine S. et al., "Structural and enzymatic investigation of the sulfolobus solfatacricus uridylate kinase shows competitive UTP inhibition and the lack of GTP stimulation", Biochemistry 46:2745-2757 (2007).
Kabsch, Wolfgang, "Automatic processing of rotation diffraction data from crystals of initially unknown symmetry and cell constants", Journal of Applied Crystallography 26:795-800 (1993).
Lindsley, Janet E. "Use of a real-time, coupled assay to measure the ATPase activity of DNA topoisomerase II", Methods in Molecular Biology 95:57-64 (2001).
O'Maille, Paul E. et al., "A single-vial analytical and quantitative gas chromatography-mass spectrometry assay for terpene synthases", Analytical Biochemistry 335:210-217 (2004).
Pakhomova, Svetlana et al., "Crystal structure of fosfomycin resistance kinase fomA from streptomyces wedmorensis", Journal of Biological Chemistry 283(42):28518-28526 (2008).
Pearson, William R., "Improved tools for biological sequence comparison", Proc. Natl. Acad. Sci. USA 85:2444 (1988).
Ramon-Maiques, Santiago et al., "Structure of acetylglutamate kinase, a key enzyme for arginine biosynthesis and a prototype for the amino acid kinase enzyme family, during catalysis", Structure 10:329-342 (2002).
Ramon-Maiques, Santiago et al., "Structural bases of feed-back control of arginine biosynthesis, revealed by the structures of two hexameric n-acetylglutamate kinases, from thermotoga maritime and *Pseudomonas aeruginosa*", J. Mol. Biol. 356:695-713 (2006).
Rohmer, Michel, "The discovery of a mevalonate-independent pathway for isoprenoid biosynthesis in bacteria, algae and higher plants", Nat. Prod. Rep. 16:565-574 (1999).
Schramm, Andrew M. et al., "Backbone flexibility, conformational change, and catalysis in a phosphohexomutase from *Pseudomonas aeruginasa*", Biochemistry 47(35):9154-9162 (2008).
Sieiro, C. et al., "Genetic basis of microbial carotenogenesis", Int. Microbiol. 6:11-16 (2003).
Smit, Arian et al., "Biosynthesis of isoprenoids via mevalonate in archaea: the lost pathway", Genome Res. 10:1468-1484 (2000).
Smith, Temple F., "Comparison of biosequences", Advances in Applied Mathematics 2:482-489 (1981).
Terwilliger, Thomas, "Solve and resolve: automated structure solution, density modification, and model building", J. Synchrotron Rad. 11:49-52 (2004).
Tiedge, Markus et al., "Importance of cysteine residues for the stability and catalytic activity of human pancreatic beta cell glucokinase", Archives of Biochemistry and Biophysics 375(2):251-260 (2000).
Uda, Kouji et al., "The role of Arg-96 in Danio rerio creatine kinase in substrate recognition and active center configuration", International Journal of Biological Macromolecules 44(5):413-418 (2009).

* cited by examiner

*Primary Examiner* — Sheridan Swope
(74) *Attorney, Agent, or Firm* — Kilpatrick Townsend and Stockton LLP

(57) ABSTRACT

Provided herein are methods and compositions relating to the synthesis of isoprenoid diphosphates using a mutated isopentenyl phosphate kinase.

4 Claims, 23 Drawing Sheets

Fig. 1A.

```
                    From  Sequence                                                                To
                              β1                      αA                     β2
         IPK-Mj       1    M--LTILKIGGSILSDKNVPYSIKWDNLERIAMEIKNALDYYKNQNKEIK                      48
         NAGK-Ec      1    MMNPLIIKIGGVLLD--------SEEALERLFSALVNYRE---SHQR--P                     37

β2         αB         β3   β4              αC
         IPK-Mj      49    LILVHGGAFGHPVAKKY--LKIEDGKKIFINMEKGFWEIQRAMR-RFNN                      95
         NAGK-Ec     38    LVIVHGGGCVVDELMKGLN-LPVKKKNGLRVTPADQIDIITGALAGTANK                     84

αC           β5   η1      β6          β7         αD
         IPK-Mj      96    IIIDTLQSYDIEAVSIQPSS----FVVFGDK----LIF----DTSAIKEM                    133
         NAGK-Ec     85    TLLAWAKKHQIAAVGLFLGDGDSVKVTQLDEELGHVGLAQPGSPKLINSL                    135

αD     β8    β9    β10      αE               β11
         IPK-Mj     134    LKRNIVPVIHGDIVIDDKNGYRIISGDDIVPYLANEIKADLILYATDVDG                    184
         NAGK-Ec    136    LENGYLPVVSSIGVTDE-GQLMNVNADQAATALAATIGA-DLILLSDVSG                    184

β12  β13 β14        αF                          αG
         IPK-Mj     185    VLIDN-KEI-KRIDKNNIYKILNYLSGSNSIDVTGGMKYKIDMIRKN-KC                    230
         NAGK-Ec    185    IIDGKGQRI-AE--M-TAAK-AEQLIEQGI--ITDGMIVKVNAALDAART                    227

β15        αH        β16
         IPK-Mj     231    ---RGFVFNGNKAN-NIYKALIGEVEGTEIDFSE                                    260
         NAGK-Ec    228    LGREVDIASWRHAEQLPALFNGMPM-GTRILA--                                    258
```

Fig. 8B.

| IPK source | SEQ ID | From | Sequence | To |
|---|---|---|---|---|
| Methanocaldococcus | 1 | 1 | ----------------------MLTIIKLGGSILSDKNVPYSIKWDNLERIAMEIKNALDYYKNQN | 44 |
| Methanococcus | 8 | 1 | -----------------------MFAIIKLGGSILCDKNVPYSINWENLENIAIEIKEAIEYYSSKN | 44 |
| Branchiostoma | 9 | 1 | ------------------------GSAVTDKSTLETPRLDAIRAAADIISQVR-------- | 53 |
| Trichoplax | 10 | 1 | MVHKCCLCQCTDVLSGLECIVKLGGSAITSKQHLEKANTQAINIAASHVHEMI---------- | 44 |
| Arabidopsis | 11 | 1 | ---MEINISESRSRSIRCIVKLGGAAITCKNELEKIHDENLEVVACQLRQAMLEGSAPS | 56 |
| Methanocaldococcus | 1 | 45 | KE-------------------IKILIVHGGGAFGHPVAKKYLKIEDG----- | 72 |
| Methanococcus | 8 | 45 | ED-------------------FKLIIVHGGGSFGHPVAKKYLKNEK----- | 71 |
| Branchiostoma | 9 | 54 | ---------------------GRCIVVHGAGSFGHFQAREHGVVWGYRDK | 82 |
| Trichoplax | 10 | 45 | ---------------------RKCVIVHGAGSFGHFHAKKYNIATGF----- | 70 |
| Arabidopsis | 11 | 57 | KVIGMDWSKRPGGSSEISCDVDDIGDQKSSEFSKFVVVHGAGSFGHFQASRSGVHKQG--- | 113 |
| Methanocaldococcus | 1 | 73 | ---LEKPIVKAGFVATRISVTNLNLEIVRALAREGIPTIGMSFPSCG--WSTSKRDVASAD | 126 |
| Methanococcus | 8 | 72 | -NDTDFEQRIGFSQTRLSVTRLNHIIVQALIEKDVPAVSISP---CGLWKTTDRSVTSTF | 127 |
| Branchiostoma | 9 | 83 | ETDTEVQTVKLGFCRTRQSVTKLLIHITEEFVRLGIPAVGVSP---LSSWVTIDDASVVKAD | 140 |
| Trichoplax | 10 | 71 | ----FEDMGKGYWEIQKAMRPKFNNIVIERLQNFE--PAVSIQA---SSFITFNHKSNLHFD | 123 |
| Arabidopsis | 11 | 114 | ---KKIFINMEKGFWEIQRAMRRFNNIIDTLQSYDIPAVSIQP---SSFVFGDKLI--FD | 185 |
| Methanocaldococcus | 1 | 127 | TSAIKEMLKRNLVPVIHGDIVIDDKN-GYTRIISGDDIVPYLANELKADLILYATDVDGVL | 185 |
| Methanococcus | 8 | 124 | TNAIEKMLIDKGLIPVIHGDIVIDEKTDNFKIFSGDHALPFLSKKLNPDLSLHASDVDGVWW | 183 |
| Branchiostoma | 9 | 141 | TDNIRDMLLEGFLPVMHGDAVLDRKR-GCTIISGDTIIKHICSVFRPRVVFLTDVPGIY | 199 |
| Trichoplax | 10 | 128 | LQPINDLLRAGFVPVVHGDAVTDTSL-GCTIISGDTTIIQILAENLCPKRIFIFTDTNGIY | 186 |
| Arabidopsis | 11 | 170 | LATVAKTIIDSGFVPVLHGDAVLDNIL-GCTIISGDVTIIRHLADHLKPEYVVFLTDVLGVT | 228 |
| Methanocaldococcus | 1 | 186 | IDNK--PIK-------RIDKNNIYRIL--------NYLSGSNSIDVTGGMKYRID--- | 223 |
| Methanococcus | 8 | 184 | -DSEFKIIE------NINSKNIEDVL------KSLKPSNKEDVTGGMHIKNVM-- | 222 |
| Branchiostoma | 9 | 200 | -DRP--PEQPGAQLIPEIQVDPDRKLHV----------SIATSSQAHDVTGGIAIKLKSA | 246 |
| Trichoplax | 10 | 187 | -DRP--PHNDDAKLLRYISVTKDGRVTN----------EIETSQLEHDVTGGVQTKIASA | 233 |
| Arabidopsis | 11 | 229 | -DRPPSPSEPDAVLKEIAVGEDGSWKVVNPLLEHTDRKVDYSVAAHDTTGGMETKISEA | 287 |
| Methanocaldococcus | 1 | 224 | -----MIRKNK--CRGFVFNGNKANNIYKALLGEVE--------GTEI----DFSE--- | 260 |
| Methanococcus | 8 | 223 | -----ECYNLG--IETIIFNGNKKRNIYNALLKNVK--------GTLI----N----- | 256 |
| Branchiostoma | 9 | 247 | IDIVTESNGHTCVMVCGIQSQAAVRACVEGQLPQG--------TGTIVQNISKHPDEVT | 297 |
| Trichoplax | 10 | 234 | AHIVSKCN--IPVHVVKLGSAAAWKLLDEGRLEES---DIATTTLQESEYPK--- | 281 |
| Arabidopsis | 11 | 288 | A-MIAKLG--VDVTIVKAATTHS-QRAINGDLRDSVPEDWLGTII----RFSK--- | 332 |

5-epi-aristolchene (5EA)

|  | Peak Area (SIMS) | [5EA] (uM) | %5FP → FPP conversion |
|---|---|---|---|
| WT | 30484 | 0.02 | 0.6% |
| I146A | 546127 | 0.3 | 10% |
| I86A | 1258955 | 0.6 | 20% |
| I86A/I146A | 1603054 | 0.8 | 27% |

METHODS AND COMPOSITION FOR ISOPRENOID DIPHOSPHATE SYNTHESIS

CROSS-REFERENCES TO RELATED APPLICATIONS

This application is a national phase application of PCT Application No. PCT/US2010/042472, filed Jul. 19, 2010, which claims the benefit of U.S. Provisional Application No. 61/226,582, filed Jul. 17, 2009, which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under MCB-0645794 awarded by the National Science Foundation. The Government has certain rights in the invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 92150-829801_ST25.TXT, created on Apr. 2, 2014, 31,298bytes, machine format IBM-PC, MS-Windows operating system, is hereby incorporated by reference.

BACKGROUND OF THE INVENTION

The biosynthesis of isopentenyl diphosphate (IPP) is essential for the production of a broad variety of isoprenoids that serve crucial roles in membrane stability, defense and communication, photoprotection, and sugar transport. Recently, a novel branch of the mevalonate pathway was discovered in the archaeon *Methanocaldococcus jannaschii* involving an enzyme called isopentenyl phosphate kinase (IPK) that could phosphorylate isopentenyl monophosphate to isopentenyl diphosphate.

Isopentenyl diphosphate (IPP) is the central precursor to a diverse collection of isoprenoids and isoprenoid-derived compounds present in many different organisms. Following its biosynthesis, successive units of IPP are used with either dimethylallyl diphosphate (DMAPP) or a growing isoprenoid diphosphate to synthesize C10, C15, or C20 oligoprenyl diphosphates known as geranyl diphosphate (GPP), farnesyl diphosphate (FPP), and geranylgeranyl diphosphate (GGPP), respectively. These three isoprenoid diphosphates are the building blocks for many downstream biosynthetic compounds that serve a colorful variety of roles amongst the different kingdoms of life. All three of them can be cyclized by their respective terpene cyclase to generate an astounding selection of volatile terpenes which are extremely important for defense and communication in plants, fungi, several insects, certain bacteria, and marine organisms (Gershenzon & Dudareva, 2007, *Nat. Chem. Biol.* 3:408-414.). FPP is the most ubiquitous of the three building blocks and is transformed into a variety of essential biomolecules throughout all kingdoms of life. Some of these biomolecules include squalene, hopanoids, and steroids (which are important for membrane structure in Archaea, Bacteria, and Eukarya, respectively) (Novakova et al., 2008, *Folia Microbiol. (Praha)* 53:237-240; Ourisson et al., 1987, *Annu. Rev. Microbiol.* 41:301-333), and dolichols, which serve a critical role in N-glycosylation and membrane anchorage of sugars in eukaryotes and archaea (Eichler & Adams, 2005, *Microbiol. Mol. Biol. Rev.* 69:393-425). GGPP is the precursor to all carotenoids, which are important for photoprotection in many plants, fungi, algae, bacteria and some archaea (Sieiro et al., 2003, *Int. Microbiol.* 6:11-16; Hemmi et al., 2003, *Biochem. Biophys. Res. Commun.* 305:586-591). Interestingly, GGPP is also a precursor to the isoprenoid-derived hydrocarbon moiety of lipids that are present exclusively in Archaea. See Koga & Morii, 2007, *Microbiol. Mol. Biol. Rev.* 71:97-120 for a review on archaeal lipids.

It is clear that IPP is a necessary building block for all downstream isoprenoids and it is essential for the survival of any organism. It is therefore crucial that we understand how this molecule is produced in various organisms. There are two known pathways that ultimately produce IPP and DMAPP (the other precursor to all downstream isoprenoid products): the mevalonate (MVA) pathway and the more recently discovered 1-deoxy-d-xylulose-5-phosphate (DXP) pathway (Rohmer, 1999, *Nat. Prod. Rep.* 16:565-574). The MVA pathway is utilized by animals, plants (cytosol), fungi, and certain bacteria, while the DXP pathway is found within plants (plastids), cyanobacteria, and certain parasitic organisms (Lange et al., 2000, *Proc. Natl. Acad. Sci. U.S.A.* 97:13172-13177). In archaea, homologs for many of the genes in the MVA pathway have been found; however, the two last genes leading up to IPP biosynthesis (normally encoding phosphomevalonate kinase and diphosphomevalonate decarboxylase) are missing. See FIG. 6. For this reason, the isoprenoid pathway in archaea has been referred to as "The Lost Pathway" (Smit & Mushegian, 2000, *Genome Res.* 10:1468-1484). Attempts to reconstruct The Lost Pathway have only recently shown promise. In 2006, a group discovered an enzyme present in the archaeon *Methanocaldococcus jannaschii* that was able to phosphorylate isopentenyl monophosphate, thereby producing IPP (Grochowski, et al., 2006, *J. Bacteriol.* 188:3192-3198). This protein, named isopentenyl phosphate kinase (IPK), not only allows for the partial reconstruction of The Lost Pathway, but also represents a completely unique branch of the universal mevalonate pathway. This is a fascinating discovery considering the fact that archaea, when compared with the other two domains from which life originated, have evolved distinct functions for isoprenoid compounds.

Isopentenyl phosphate kinase shares significant sequence homology with the amino acid kinase (AAK) superfamily (Pf000696). See FIG. 7. Members of this family usually utilize magnesium and ATP to phosphorylate small molecule substrates that contain carboxylate, carbamate, phosphonate, or phosphate functional groups. Disclosed herein, inter alia, is the crystal structure of isopentenyl phosphate kinase from *M. jannaschii* solved in its apo form and in complex with substrate. These structures coupled with the biochemical analysis of several mutants suggest an important role for an active site histidine residue which is not conserved among all AAK family members and has not previously been assigned a role in catalysis.

BRIEF SUMMARY OF THE INVENTION

Provided herein are methods and compositions pertaining to the synthesis of isoprenoid diphosphates.

In one aspect, there is provided an isolated mutated isopentenyl phosphate kinase having at least 60%, 65%, 70%, 75%, 80%, 85%, 86%, 87%, 88%, 89%, 90%, 91%, 92%, 93%, 94%, 95%, 96%, 97%, 98%, 99% or 100% sequence identity to at least a 25, 50, 100, 150, 200 or 250 contiguous amino acid sequence set forth in SEQ ID NO:1, SEQ ID NO:8, SEQ ID NO:9, SEQ ID NO:10 or SEQ ID NO:11 or the entire sequence set forth in SEQ ID NO:1, SEQ ID NO:8 SEQ ID NO:9, SEQ ID NO:10 or SEQ ID NO:11, wherein the isopentenyl phosphate kinase includes a mutation at Val62, Ala63, Tyr66, Leu67, Phe76, Met79, Phe83, Ile86, Ala89, Met90, Ile146, Ile156 and/or Tyr154 of SEQ ID NO:1 or at an equivalent amino acid of SEQ ID NO:8, SEQ ID NO:9, SEQ ID NO:10 or SEQ ID NO:11.

In another aspect, a method of synthesizing an isoprenoid diphosphate is provided. The method includes contacting an isoprenoid monophosphate and a phosphate donor with a mutated isopentenyl phosphate kinase (e.g. as described herein) thereby forming an isoprenoid diphosphate.

In another aspect, there is provided a method of identifying an amino acid substitution in an isopentenyl phosphate kinase that increases isoprenoid diphosphate formation rate. The method includes determining a hypothetical binding position of an isoprenoid monophosphate within an active site of a first isopentenyl phosphate kinase using a computer modeling program. The method further includes, based on the hypothetical binding position, making a test mutated isopentenyl phosphate kinase including an amino acid substitution relative to the first isopentenyl phosphate kinase. The method further includes contacting the test mutated isopentenyl phosphate kinase with an isoprenoid monophosphate and a phosphate donor and determining a first rate of formation of an isoprenoid diphosphate. The method further includes comparing the first rate of formation of the isoprenoid diphosphate with a second rate of formation, wherein the second rate of formation is determined by contacting the first isopentenyl phosphate kinase with the isoprenoid monophosphate and the phosphate donor, wherein a higher first rate of formation relative to the second rate of formation indicates that the amino acid substitution increases isoprenoid diphosphate formation rate.

BRIEF DESCRIPTION OF THE DRAWINGS

FIG. 1: Primary sequence, tertiary architecture and active site snapshots of IPK. FIG. 1A: Primary sequence of IPK from *M. jannaschii* (SEQ ID NO:1) is depicted aligned with *E. coli* NAGK (SEQ ID NO:22). The boxed motifs correlate with the depiction in the three-dimensional model (FIG. 1C).

FIG. 2: Position of the β-sulfate ion in the IPK active site. FIG. 2C: Monomer A of the IPK-IPPβS complex is shown depicting the β-sulfate ion and the surrounding residues. FIG. 2D: Monomer B of the IPK-IPPβS complex is depicted oriented as in FIG. 2C.

FIG. 3: The N-terminal hydrophobic pocket accommodates the tail of IP. FIG. 3A depicts a close-up view of the N-terminal domain depicting the isopentenyl tail and the surrounding hydrophobic residues. The motifs surrounding the active site are indicated by named secondary structural element as described herein. Residues within van der Waals contact of the isopentenyl chain include Ile86, Met90, and Ile156. FIG. 3B depicts dual conformation of the β1-αA loop in monomer A of the IPK-IP complex. One conformation places the loop close to the β2-αB loop and the IP substrate, while the other conformation places the loop in close proximity to the β-sulfate ion.

FIG. 4: The polar head of IP and its stabilizing residues. FIG. 4A depicts the tertiary structure superposition of monomers A and B of the IPK-IP complex. The rmsd (root mean square deviation) between the two monomers is 1.31 Å. FIGS. 4B-4C depict close-up views of residues proximal to and hydrogen bonding with the α-phosphate of IP in monomers A (FIG. 4B) and B (FIG. 4C). In monomer B, a water molecule bridges the side-chain amino group of Lys6 and a nonbridging oxygen atom of the IP phosphate. FIG. 4D depicts the tertiary structure superposition of monomers A and B of the IPK-IPP complex. The rmsd between the two monomers is 1.39 Å. FIGS. 4E-4F depict views of the multiple conformers of IPP (labeled as IPP-a and IPP-b) in both monomers A (FIG. 4E) and B (FIG. 4F).

FIG. 8: Common Ground for Kinases with Phosphate Functional Groups. FIG. 8B: Alignment of IPK homologs. As depicted in FIG. 8B, the sequences of five IPK homologs (SEQ ID NOS: 1, 8, 9, 10 and 11) were aligned for comparison. Legend: "From" and "To" refer to starting and ending sequence number of each sequence, respectively. Boxed regions indicate identical residue(s).

FIG. 11: Farnesyl phosphate (FP) phosphorylation by IPK chain length mutants. FIG. 11A depicts the coupled IPK-sesquiterpene synthase reaction used to test for FP transphosphorylation. FIG. 11B depicts comparative bar graph showing several IPK mutants qualitatively tested for their ability to convert FP to FPP, expressed as a percentage of maximal production of 5-epi-aristolocene produced from IPK-generated FPP using wild-type IPK and identical concentrations of wild-type tobacco 5-epi-aristolochene synthase incubated for equivalent lengths of time.

FIG. 14: FPP binding modes based on molecular modeling.

FIG. 15 depicts a comparison of the mutant structure (IPK I86A/I146A) in complex with GP with wild type structure of IPK in complex with IP.

FIG. 16 depicts a portion of mutant structure IPK I86A/I156A in complex with GP. Residue side chains F83, I86A, I146 are mutated to widen the cavity.

FIG. 17 depicts a portion of mutant structure IPK I86A/I156A in complex with GP. Mutation at residue I86A back to isoleucine, or other larger residue (e.g., leucine) is designed to force chain downward. Similarly, mutation at residue I156A to an even smaller residue (e.g., glycine) redirects the chain. Similarly, mutation at residue F76 to a smaller residue redirects the chain.

FIG. 18 depicts a portion of the structure of IPK in complex with GP. Mutation of His60 to a longer side chain (e.g., H60R) encourages the side chain to interact with the phosphate group of GP.

DETAILED DESCRIPTION OF THE INVENTION

I. Definitions

Figure 1B:
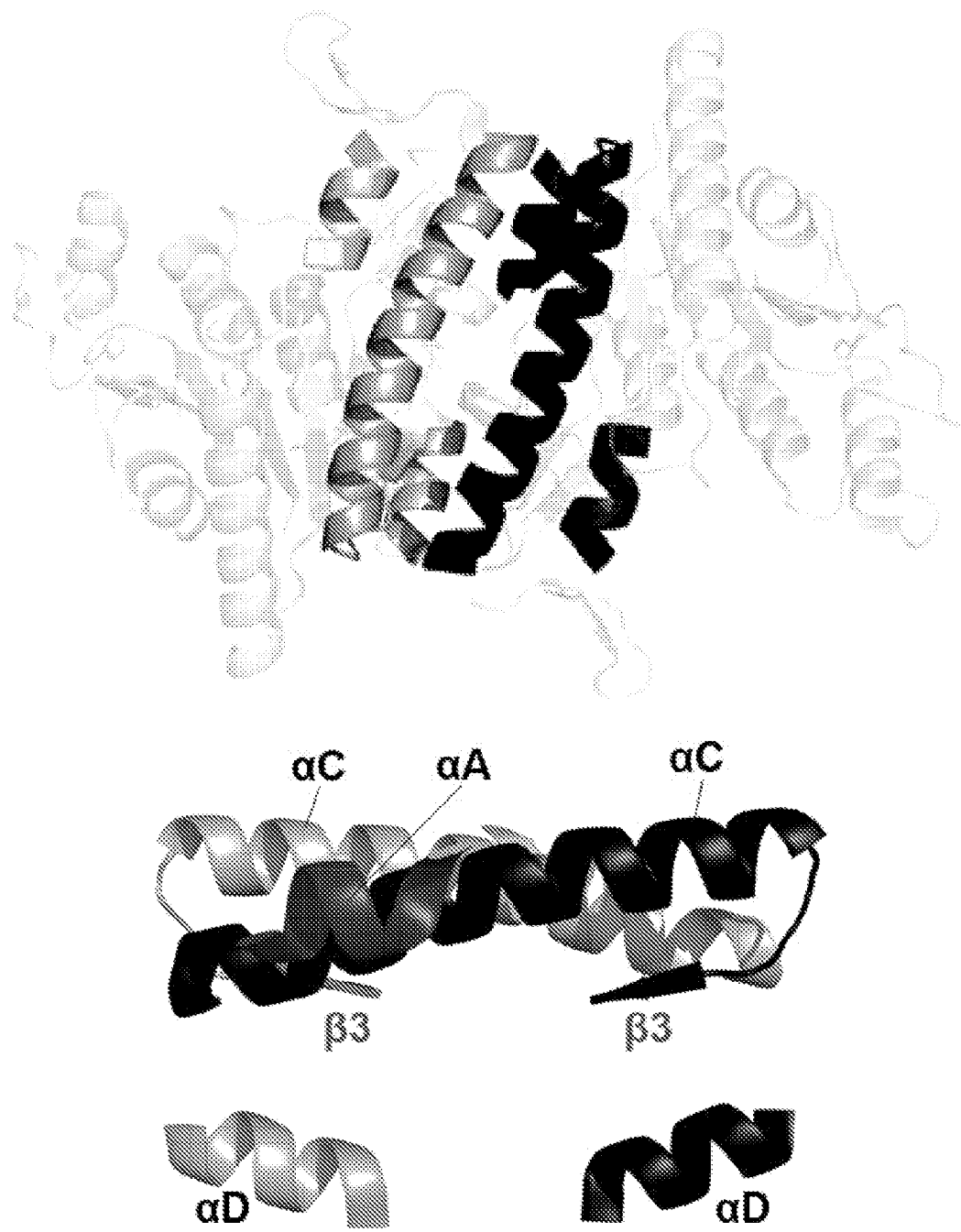
FIG. 1B: Global view of the IPK dimer (top) and a close-up view of the dimerization interface (bottom). Motifs positioned near the dimerization interface are gray for one monomer and black for the other.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched chain, or combination thereof, which may be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two heteroatoms may be consecutive, such as, for example, —CH$_2$—NH—OCH$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

For brevity, the "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo," as used herein, means an oxygen that is double bonded to a carbon atom.

The term "alkylsulfonyl," as used herein, means a moiety having the formula —S($O_2$)—R', where R' is an alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted foams of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN, and —NO$_2$ in a number ranging from zero to (2m'+1), where m' is the total number of carbon atoms in such radical. R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN, —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R"', and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"')$_d$—, where s and d are independently integers of from 0 to 3, and X' is —O—, —NR'—, —S—, —S(O)—, —S(O)$_2$—, or —S(O)$_2$NR'—. The substituents R, R', R", and R"' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or " size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or " lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are encompassed within the scope of the present invention.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., National Center for Biotechnology Information [NCBI] web site or the like). Such sequences are then said to be "substantially identical." As described below, the preferred algorithms can account for gaps and the like. Identity may exist over a region that is at least about 25 amino acids or nucleotides in length, or over a region that is 50-250 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the NCBI. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$ ,50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., John Wiley & Sons.

For PCR (polymerase chain reaction), a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

II. IPK and Related Protein Sequences

The sequence of IPK from *M. jannaschii* follows:

```
                                                       (SEQ ID NO: 1)
MLTILKLGGSILSDKNVPYSIKWDNLERIAMEIKNALDYYKNQNKEIKLILVHGGGAFGHPVA

KKYLKIEDGKKIFINMEKGFWEIQRAMRRFNNIIIDTLQSYDIPAVSIQPSSFVVFGDKLIFDTS

AIKEMLKRNLVPVIHGDIVIDDKNGYRIISGDDIVPYLANELKADLILYATDVDGVLIDNKPIK

RIDKNNIYKILNYLSGSNSIDVTGGMKYKIEMIRKNKCRGFVFNGNKANNIYKALLGEVEGTE

IDFSE.
```

The sequence of FomA from *S. wedmorensis* follows:

```
                                                       (SEQ ID NO: 2)
MTPDFLAIKVGGSLFSRKDEPGSLDDDAVTRFARNFARLAETYRGRMVLISGGGAFGHGAIR

DHDSTHAFSLAGLTEATFEVKKRWAEKLRGIGVDAFPLQLAAMCTLRNGIPQLRSEVLRDVL

DHGALPVLAGDALFDEHGKLWAFSSDRVPEVLLPMVEGRLRVVTLTDVDGIVTDGAGGDTI

LPEVDARSPEQAYAALWGSSEWDATGAMHTKLDALVTCARRGAECFIMRGDPGSDLEFLTA

PFSSWPAHVRSTRITTTASA.
```

The sequence of UMPK A from *C. pneumoniae* follows:

```
                                                       (SEQ ID NO: 3)
MAKQTRRVLFKISGEALSKDSSNRIDEMRLSRLVSELRAVRNNDIEIALVIGGGNILRGLAEQK

ELQINRVSADQMGMLATLINGMAVADALKAEDIPCLLTSTLSCPQLADLYTPQKSIEALDQG

KILICTTGAGSPYLTTDTGAALRACELNVDVLIKATMHVDGVYDKDPRLFPDAVKYDFVSYK

DFLSNQLGVMDASAISLCMDSHIPIRVFSFLQHSLEKALFDPTIGTLVSEDVNHVCSPRH.
```

The sequence of UMPK A from *E. coli* follows:

```
                                                       (SEQ ID NO: 4)
MATNAKPVYKRILLKLSGEALQGTEGFGIDASILDRMAQEIKELVELGIQVGVVIGGGNLFRG

AGLAKAGMNRVVGDHMGMLATVMNGLAMRDALHRAYVNARLMSAIPLNGVCDSYSWAE

AISLLRNNRVVILSAGTGNPFFTTDSAACLRGIEIEADVVLKATKVDGVFTADPAKDPTATMY

EQLTYSEVLEKELKVMDLAAFTLARDHKLPIRVFNMNKPGALRRVVMGEKEGTLITE.
```

The sequence of UMPK A from *R. prowazekii* follows:

```
                                                       (SEQ ID NO: 5)
MASDINALKYKKVLLKVSGEALMGNKQFGHEYEVIKKIAEDIKEVIDLGLEVAIVVGGGNIY

RGINAALVGMDRASADYIGMLATVMNALTLQNVMESLGIYTRVLSAIPMMSVCEPYIRRKA

KRHMEKKRVVIFAGGTGNPFCTTDSAAVLRAIEMNCDILLKATQVDGVYDSDPKKNPNAKK

YFTISYKDVINNHLQVMDTAAIAVARENKLPIRVFSIKEHGNFARVIQDKGQYTTIGE.
```

The sequence of UMPK A from *A. aeolicus* follows:

(SEQ ID NO: 6)
MEEKPKYKRILLKLSGEAFAGEQGYGIDPAFLEYISHEIKNVYDLGVQVAIVIGGGNIFRGFQG

KEIGVDRATADYMGMLATVINALALQSALENHVNIPTRVLSAIEMRQVAEPYIRRRAIRHLE

KGRIVIFAGGTGNPFFSTDTAAALRAAEIGAEVLIKATKVGGIYDKDPEKYPDAVLIKEISYLE

VINMGLKVMDHTALTLCKENEIPIIVLNVKEKGNLRRAVLGEEVGSVVRG.

The sequence of UMPK A from *Synechocystis* sp. follows:

(SEQ ID NO: 7)
MGGILRLTLIPCLYINGDGGMSYQRVLLKLSGEALMGDLGYGIDPAVVGTIAQEIKDVLQAG

VQLAIVVGGGNEERGVKASAAGMDRATADYIGMIATVMNAMTLQDALEQMDIPTRVLTAIA

MQEVAEPYIRRRAIRHLEKGRVVIFGAGSGNPFFTTDTTAALRAAEIDAEVVFKATKVDGVY

DSDPKTNPNARRFTTLTYSHVLAEDLKVMDSTAIALCKDNNIPIMIFDLGVPGNIVRAIKGEA

VGTLVGENCEVS.

The sequence of IPK from *Methanococcus maripaludis* (mesophilic archaea) follows:

(SEQ ID NO: 8)
MFAILKLGGSILCDKNVPYSINWENLENIAIEIKEAIEYYSSKNEDFKLIIVHGGGSFGH

PVAKKYLKNEKFEDMGKGYWEIQKAMRKFNNIVIEELQNFEPAVSIQASSFITFNHKS

NLHFDTNAIEKMLDKGLIPVIHGDIVIDEKTDNFKIFSGDHALPFLSKKLNPDLSLHAS

DVDGVWDSEFKIIENINSKNIEDVLKSLKPSNKEDVTGGMHLKVMECYNLGIETIIFN

GNKKRNIYNALLKNVKGTLIN.

The sequence of IPK from *Trichoplax adhaearens* (metazoan) follows:

(SEQ ID NO: 9)
MALENRHVDCIIKLGGSAITSKQHLEKANTQAINIAASHVHEMTRKCVIVHGAGSFG

HFHAKKYNIATGFNDTDFEQQRIGFSQTRLSVTKLNHIIVQALIEKDVPAVSISPCGLW

KTTDRSVTSTFLQPINDLLRAGFVPVVHGDAVIDTSLGCTILSGDTIIQILAENLCPKRII

FITDTNGIYDRPPHNDDAKLLRYISVTKDGKVTNEIETSQLEHDVTGGVQTKIASAAH

IVSKCNIPVHVVKLGSAAAWKLLDKGELEESDIATTITLQESEYPK.

The sequence of IPK from *Arabidopsis thaliana* (thale cress) follows:

(SEQ ID NO: 10)
MELNISESRSRSIRCIVKLGGAAITCKNELEKIHDENLEVVACQLRQAML

EGSAPSKVIGMDWSKRPGSSEISCDVDDIGDQKSSEFSKFVVVHGAGSFG

HFQASRSGVHKGGLEKPIVKAGFVATRISVTNLNLEIVRALAREGIPTIG

MSPFSCGWSTSKRDVASADLATVAKTIDSGFVPVLHGDAVLDNILGCTIL

SGDVIIRHLADHLKPEYVVFLTDVLGVYDRPPSPSEPDAVLLKEIAVGED

GSWKVVNPLLEHTDKKVDYSVAAHDTTGGMETKISEAAMIAKLGVDVYIV

KAATTHSQRALNGDLRDSVPEDWLGTIIRFSK.

The sequence of IPK from *Branchiostoma floridae* (lancelet) follows:

(SEQ ID NO: 11)
MVHKCCLCQCTDVLSGLECIVKLGGSAVTDKSTLETPRLDAIRAAADIISQVRGRCIV

VHGAGSFGHFQAREHGVVWGYRDKETDTEVQTVKLGFCRTRQSVTKLLHIITEEFV

RLGIPAVGVSPLSSWVTDDASVVKADTDNIRDMLLEGFLPVMHGDAVLDRKRGCTI

LSGDTIIKHLCSVFRPPRVVFLTDVPGIYDRPPEQPGAQLIPEIQVDRDRKLHVSIATSS

QAHDVTGGIALKLKSAIDIVTESNGHTCVMVCGIQSQAAVRACVEGQLPQGTGTIVQ

NISKHPDEVT.

The sequence of NAGK from *E. coli* follows:

(SEQ ID NO: 22)
MMNPLIIKLGGVLLDSEEALERLFSALVNYRESHQRPLVIVHGGGCVVDE

LMKGLNLPVKKKNGLRVTPADQIDIITGALAGTANKTLLAWAKKHQIAAV

GLFLGDGDSVKVTQLDEELGHVGLAQPGSPKLINSLLENGYLPVVSSIGV

TDEGQLMNVNADQAATALAATLGADLILLSDVSGILDGKGQRIAEMTAAK

-continued
AEQLIEQGIITDGMIVKVNAALDAARTLGRPVDIASWRHAEQLPALFNGM

PMGTRILA.

III. Alignment and Comparison of IPK Sequences

Figure 8A:
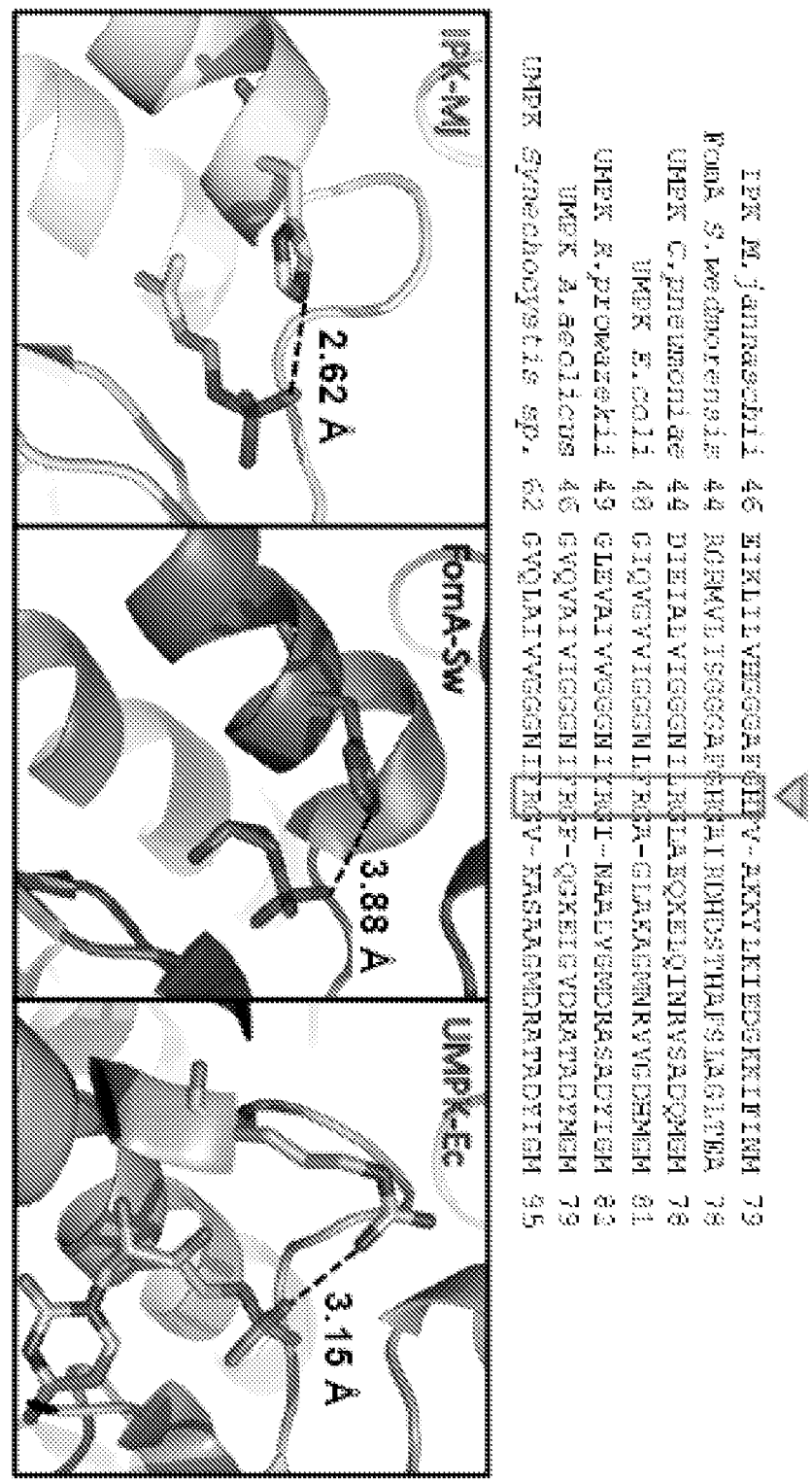
FIG. 8A: Comparison of partial primary sequences. Interestingly, there are only two other members of the exemplary FomA and UMPK proteins that contain an aligning residue at His60 of IPK. As seen from the sequence alignment, in FomA kinase, the aligning residue is histidine, while in UMP kinase, it is arginine. Active site snapshots of each kinase are also shown. In addition to IPK, FomA kinase and UMP kinase happen to be the two other members of the family that phosphorylate a substrate containing a phosphate or phosphonate functional group. Legend of partial sequences: IPK *M. jannaschii* (SEQ ID NO:1); FomA *S. wedmorensis* (SEQ ID NO:2); UMPK *C. pneumoniae* (SEQ ID NO:3); UMPK *E. coli* (SEQ ID NO:4); UMPK *R. prowazekii* (SEQ ID NO:5); UMPK *A. aeolicus* (SEQ ID NO:6); UMPK *Synechocystis* sp. (SEQ ID NO:7).

The alignment of specific regions or amino acids of homologous proteins is a useful methodology for identifying structural and functional role(s) of individual amino acids relevant to the activity of a family of related (e.g., homologous) proteins. These roles include, e.g., specificity, catalysis and the like. For example, as depicted in FIG. 8B, at least 22 single residue or multiple contiguous residue regions are identified as identical in a comparison of the primary sequences of IPK proteins described herein (SEQ ID NOS: 1, 8, 9, 10 and 11). By aligning these common (i.e., identically conserved) residues or multiple contiguous residue regions, the putative roles of other residues within the proteins, differing e.g., between species, can be elucidated. Based on sequence comparison and modeling studies, as described herein and known in the art, residues were compared and identified in the IPK family. For example, as shown in Table 1 following, each residue identified in *M. jannaschii* (SEQ ID NO:1) as having a putative role in specificity and/or catalysis has a corresponding residue in the other IPK family members. For example, mutation of V62 in SEQ ID NO:1 is mirrored in a corresponding mutation of V62 of SEQ ID NO:8, Q69 of SEQ ID NO:9, H60 of SEQ ID NO:10 or Q103 of SEQ ID NO:11. Accordingly, each residue within SEQ ID NO:1 has an equivalent amino acid in SEQ ID NOS:8-11. See Table 1. The term "equivalent amino acid" in the context of mutations as described herein refers to an amino acid at an equivalent position with respect to a reference. For example, Q69 of SEQ ID NO:9 is an equivalent amino acid with respect to V62 of SEQ ID NO:1, and the like.

TABLE 1

Aligned residues in IPK homologs.

| *M. jannaschii* SEQ ID NO: 1 | *M. maripaludis* SEQ ID NO: 8 | *T. adhaearens* SEQ ID NO: 9 | *A. thaliana* SEQ ID NO: 10 | *B. floridae* SEQ ID NO: 11 |
|---|---|---|---|---|
| V62 | V62 | Q69 | H60 | Q103 |
| A63 | A63 | A70 | A61 | A104 |
| Y66 | Y66 | H73 | Y64 | S107 |
| L67 | L67 | G74 | N65 | G108 |
| F76 | F72 | V88 | F75 | K116 |
| M79 | M75 | V91 | Q78 | V119 |
| F83 | V79 | F95 | F82 | F123 |
| I86 | I82 | T98 | T85 | T126 |
| A89 | A85 | S101 | S88 | S129 |
| M90 | M86 | V102 | V89 | V130 |
| I146 | I143 | A160 | A147 | A189 |
| I156 | I154 | I170 | I157 | I199 |
| Y154 | F152 | C168 | C155 | C197 |

IV. Mutated Isopentenyl Phosphate Kinases

In one aspect, there is provided an isolated mutated isopentenyl phosphate kinase having at least 60%, 65%, 70%, 75%, 80%, 85%, 86%, 87%, 88%, 89%, 90%, 91%, 92%, 93%, 94%, 95%, 96%, 97%, 98%, 99% or 100% sequence identity to at least a 25, 50, 100, 150, 200 or 250 contiguous amino acid sequence set forth in SEQ ID NO:1, SEQ ID NO:8, SEQ ID NO:9, SEQ ID NO:10 or SEQ ID NO:11 or the entire sequence set forth in SEQ ID NO:1, SEQ ID NO:8 SEQ ID NO:9, SEQ ID NO:10 or SEQ ID NO:11, wherein the isopentenyl phosphate kinase includes a mutation at Val62, Ala63, Tyr66, Leu67, Phe76, Met79, Phe83, Ile86, Ala89, Met90, Ile146, Ile156 and/or Tyr154 of SEQ ID NO:1 or at an equivalent amino acid of SEQ ID NO:8, SEQ ID NO:9, SEQ ID NO:10 or SEQ ID NO:11. In some embodiments, there is provided an isolated mutated isopentenyl phosphate kinase having at least 90%, 91%, 92%, 93%, 94%, 95%, 96%, 97%, 98%, 99% sequence identity to at least a 50, 100, 150, 200 contiguous amino acid sequence set forth in SEQ ID NO:1, SEQ ID NO:8, SEQ ID NO:9, SEQ ID NO:10 or SEQ ID NO:11 or the entire sequence set forth in SEQ ID NO:1, SEQ ID NO:8 SEQ ID NO:9, SEQ ID NO:10 or SEQ ID NO:11, wherein the isopentenyl phosphate kinase includes a mutation at Val62, Ala63, Tyr66, Leu67, Phe76, Met79, Phe83, Ile86, Ala89, Met90, Ile146, Ile156 or Tyr154 of SEQ ID NO:1 or at an equivalent amino acid of SEQ ID NO:8, SEQ ID NO:9, SEQ ID NO:10 or SEQ ID NO:11. In some embodiments, there is provided an isolated mutated isopentenyl phosphate kinase having at least 90%, 91%, 92%, 93%, 94%, 95%, 96%, 97%, 98%, 99% sequence identity to at least a 200 contiguous amino acid sequence set forth in SEQ ID NO:1, SEQ ID NO:8, SEQ ID NO:9, SEQ ID NO:10 or SEQ ID NO:11 or the entire sequence set forth in SEQ ID NO:1, SEQ ID NO:8 SEQ ID NO:9, SEQ ID NO:10 or SEQ ID NO:11, wherein the isopentenyl phosphate kinase includes a mutation at Val62, Ala63, Tyr66, Leu67, Phe76, Met79, Phe83, Ile86, Ala89, Met90, Ile146, Ile156 or Tyr154 of SEQ ID NO:1 or at an equivalent amino acid of SEQ ID NO:8, SEQ ID NO:9, SEQ ID NO:10 or SEQ ID NO:11. In some embodiments, there is provided an isolated mutated isopentenyl phosphate kinase having at least 90% sequence identity to at least a 200 contiguous amino acid sequence set forth in SEQ ID NO:1, SEQ ID NO:8 SEQ, ID NO:9, SEQ ID NO:10 or SEQ ID NO:11 or the entire sequence set forth in SEQ ID NO:1, SEQ ID NO:8 SEQ ID NO:9, SEQ ID NO:10 or SEQ ID NO:11, wherein the isopentenyl phosphate kinase includes a mutation at Val62, Ala63, Tyr66, Leu67, Phe76, Met79, Phe83, Ile86, Ala89, Met90, Ile146, Ile156 or Tyr154 of SEQ ID NO:1 or at an equivalent amino acid of SEQ ID NO:8, SEQ ID NO:9, SEQ ID NO:10 or SEQ ID NO:11. In some embodiments, there is provided an isolated mutated isopentenyl phosphate kinase having at least 90% sequence identity to at least a 250 contiguous amino acid sequence set forth in SEQ ID NO:1, SEQ ID NO:8, SEQ ID NO:9, SEQ ID NO:10 or SEQ ID NO:11 or the entire sequence set forth in SEQ ID NO:1, SEQ ID NO:8 SEQ ID NO:9, SEQ ID NO:10 or SEQ ID NO:11, wherein the isopentenyl phosphate kinase includes a mutation at Val62, Ala63, Tyr66, Leu67, Phe76, Met79, Phe83, Ile86, Ala89, Met90, Ile146, Ile156 or Tyr154 of SEQ ID NO:1 or at an equivalent amino acid of SEQ ID NO:8, SEQ ID NO:9, SEQ ID NO:10 or SEQ ID NO:11. In some embodiments, there is provided an isolated mutated isopentenyl phosphate kinase having at least 90% sequence identity to SEQ ID NO:1, SEQ ID NO:8, SEQ ID NO:9, SEQ ID NO:10 or SEQ ID NO:11, wherein the isopentenyl phosphate kinase includes a mutation at Val62, Ala63, Tyr66, Leu67, Phe76, Met79, Phe83, Ile86, Ala89, Met90, Ile146, Ile156 or Tyr154 of SEQ ID NO:1 or at an equivalent amino acid of SEQ ID NO:8, SEQ ID NO:9, SEQ ID NO:10 or SEQ ID NO:11. In some embodiments, there is provided an isolated mutated isopentenyl phosphate kinase having the amino acid sequence set forth in SEQ ID NO:1, SEQ ID NO:8, SEQ ID NO:9, SEQ ID NO:10 or SEQ ID NO:11, wherein the isopentenyl phosphate kinase includes a mutation at Val62, Ala63, Tyr66, Leu67, Phe76, Met79, Phe83, Ile86, Ala89, Met90, Ile146, Ile156 or Tyr154 of SEQ ID NO:1 or at an equivalent amino acid of SEQ ID NO:8, SEQ ID NO:9, SEQ ID NO:10 or SEQ ID NO:11. In some embodiments, there is provided an isolated mutated isopentenyl phosphate kinase having at least 90% sequence identity to a 200 contiguous amino acid sequence set forth in SEQ ID NO:1, SEQ ID NO:8 SEQ ID NO:9, SEQ ID NO:10 or SEQ ID NO:11, wherein the isopentenyl phosphate kinase includes a mutation at Val62, Ala63, Tyr66, Leu67, Phe76, Met79, Phe83, Ile86, Ala89, Met90, Ile146, Ile156 or Tyr154 of SEQ ID NO:1 or at an equivalent amino acid of SEQ ID NO:8, SEQ ID NO:9, SEQ ID NO:10 or SEQ ID NO:11. In some embodiments, the mutated isopentenyl phosphate kinase is at least 50, 100, 150, 200, 210, 220, 230, 240, 250, 252, 254, 256, 258, 259 or 260 amino acids in length. The mutation may be an amino acid substitution mutation, an amino acid deletion mutation or an amino acid addition mutation according to teachings and guidance provided herein.

One of skill will immediately understand the amino acids identified by the numbers in the preceding paragraph and throughout the present description references the numbering scheme as provided in the IPK sequence of *M. jannaschii* (SEQ ID NO:1). A person of ordinary skill in the art will also immediately recognize the identity of these amino acids in other isopentenyl diphosphate (IPP) sequences such as those provided in the "IPK sequences" provided (e.g. Table 1). For example, Val62, Ala63, Tyr66, Leu67, Phe76, Met79, Phe83, Ile86, Ala89, Met90, Ile146, Ile156 and Tyr154 are equivalent to Val62, Ala63, Tyr66, Leu67, Met 75, Val79, Ile82, Ala85, Met86, Ile143, Ile154 and Phe152 of SEQ ID NO:8, respectively, Gln69, Ala70, His73, Gly74, Val88, Val91, Phe95, Thr98, Ser101, Val102, Ala160, Ile170 and Cys168 of SEQ ID NO:9, respectively, His60, Ala61, Tyr64, Asn65, Phe75, Gln78, Phe82, Thr85, Ser88, Val89, Ala147, Ile157 and Cys155 of SEQ ID NO:10, respectively, or Gln103, Ala104, Ser107, Gly108, Lys116, Val119, Phe123, Thr126, Ser129, Val130, Ala189, Ile199 and Cys197 of SEQ ID NO:1 1, respectively. See Table 1 above.

In some embodiments, the mutated isopentenyl phosphate kinase includes one or more mutations of amino acids selected from mutations at Val62, Ile86, Met90, Ala63, Ala89 and/or Ile156 of SEQ ID NO:1, or an equivalent amino acid of SEQ ID NO:8, SEQ ID NO:9, SEQ ID NO:10 or SEQ ID NO:11. The mutated isopentenyl phosphate kinase may also include one or more mutations selected from mutations at Ile86, Met90 and/or Ile156 of SEQ ID NO:1, or an equivalent amino acid of SEQ ID NO:8, SEQ ID NO:9, SEQ ID NO:10 or SEQ ID NO:11. In certain embodiments, the mutated isopentenyl phosphate kinase includes one or more mutations selected from one or more mutations at Ala63 and/or Ala89 of SEQ ID NO:1, or an equivalent amino acid of SEQ ID NO:8, SEQ ID NO:9, SEQ ID NO:10 or SEQ ID NO:11 (e.g., where the added or substituted amino acid contains a greater number of atoms in the side chain than alanine). The mutated isopentenyl phosphate kinase may also include one or more mutations at Met90, Ile86, Ile156, Ile146, Phe76, Phe83, Tyr154 and/or Met79 of SEQ ID NO:1, or an equivalent amino acid of SEQ ID NO:8, SEQ ID NO:9, SEQ ID NO:10 or SEQ ID NO:11. In some embodiments, the mutated isopentenyl phosphate kinase includes one or more mutations at Met90, Ile156, Ile86 and/or Ile146 of SEQ ID NO:1, or an equivalent amino acid of SEQ ID NO:8, SEQ ID NO:9, SEQ ID NO:10 or SEQ ID NO:11. In other embodiments, the mutated isopentenyl phosphate kinase includes one or more mutations at Phe76, Phe83 and/or Met79 of SEQ ID NO:1, or an equivalent amino acid of SEQ ID NO:8, SEQ ID NO:9, SEQ ID NO:10 or SEQ ID NO:11. In certain embodiments, the mutated isopentenyl phosphate kinase includes a mutation at Tyr154 of SEQ ID NO:1, or an equivalent amino acid of SEQ ID NO:8, SEQ ID NO:9, SEQ ID NO:10 or SEQ ID NO:11. Other embodiments include mutations at any one or all of the following groups of positions: Met90; Met90, Ile86, Ile146, Ile156, Ala63, Leu67 and/or Tyr66; Met90, Ile156, Ile86 and/or Ile146; Ala63 and/ or Ala89; Leu67 and/or Tyr66; Ile146, Ile156, Ala63, Phe76 and/or Leu67; Ile146 and/or Ile156; Ala63; Leu67 and/or Phe76; Ile86, Ile146, Ile156, Ala63, Met90, Leu67 and/or Phe76; Ile86, Ile146, Ile156, Met90 and/or Ala63; Ile86, Ile146, Ile156, Met90 and/or Ala63; Phe83, Ile86, Ile146, and/or Ile156 of SEQ ID NO:1, or an equivalent amino acid of SEQ ID NO:8, SEQ ID NO:9, SEQ ID NO:10 or SEQ ID NO:11. More specifically, the mutated isopentenyl phosphate kinase may include one or more mutations selected from F83A, I86A and/or I146A; I86A, I146A and/or I156A; F83A, I86A and/or I156A; I86A and/or I146A; I146G, I86A, I86G, I146A, I156V and/or I146V; Ile86, Ile146 and/or Ile156 of SEQ ID NO:1, or an equivalent amino acid of SEQ ID NO:8, SEQ ID NO:9, SEQ ID NO:10 or SEQ ID NO:11.

In some embodiments, where the mutated isopentenyl phosphate kinase includes a substitution or addition mutation, the amino acid substituted or added contains fewer side chain atoms than the original amino acid (e.g. Val62, Ala63, Tyr66, Leu67, Phe76, Met79, Phe83, Ile86, Ala89, Met90, Ile146, Ile156 and/or Tyr154 of SEQ ID NO:1, or an equivalent amino acid of SEQ ID NO:8, SEQ ID NO:9, SEQ ID NO:10 or SEQ ID NO:11). For example, where the original amino acid is Ala89, the alanine may be substituted with glycine. Alternatively, glycine may be added at position 89. In other embodiments, where the mutated isopentenyl phosphate kinase includes a substitution or addition mutation, the amino acid substituted or added contains more side chain atoms than the original amino acid. One of skill may easily determine the desired characteristics of the amino acid substituted or added using the characteristics provided herein. In some embodiments, the substituted amino acid is a glycine or alanine (e.g. alanine).

In some embodiments, the mutated isopentenyl phosphate kinase is capable of catalyzing a reaction between an isoprenoid monophosphate and a phosphate donor to produce an isoprenoid diphosphate. Isoprenoid monophosphates, phosphate donors and isoprenoid diphosphates are described in more detail below.

In some embodiments, the mutated isopentenyl phosphate kinase includes a mutation at Val62, Ala63, Tyr66, Leu67, Phe76, Met79, Phe83, Ile86, Ala89, Met90, Ile146, Ile156 and/or Tyr154 of SEQ ID NO:1 or at an equivalent amino acid of SEQ ID NO:8, SEQ ID NO:9, SEQ ID NO:10 or SEQ ID NO:11. In some embodiments, the mutations at Val62, Tyr66, Leu67, Phe76, Met79, Phe83, Ile86, Met90, Ile146, Ile156 and Tyr154 are independently a size reducing amino acid substitution mutation. "Size reducing amino acid substitution mutation" refers to an amino acid substitution mutation in which the stated residue (e.g. Val62) has been replaced with a different amino acid (also referred to herein as a "mutant residue") resulting in a reduction of the volume occupied by the mutant residue side chain relative to the volume occupied by the stated residue side chain (e.g. Val62Ala or Val62Gly). In some embodiments, mutation at Ala63 and Ala89 are independently a size reducing amino acid substitution mutation or a size increasing amino acid substitution mutation. "Size increasing amino acid substitution mutation" refers to an amino acid substitution in which the stated residue (e.g. Ala63) has been replaced with a different amino acid (also referred to herein as a "mutant residue") resulting in an increase of the volume occupied by the mutant residue side chain relative to the volume occupied by the stated residue side chain (e.g. Ala63Val).

In some embodiments, the mutated isopentenyl phosphate kinase includes a size reducing amino acid substitution mutation at I86, F83, I146 or I156 of SEQ ID NO:1 or at an equivalent amino acid of SEQ ID NO:8, SEQ ID NO:9, SEQ ID NO:10 or SEQ ID NO:11. In some embodiments, the mutated isopentenyl phosphate kinase includes a mutation at Val62, Ile86, Met90, Ala63, Ala89 or Ile156 of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Ile86, Met90 or Ile156 of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Val62, Ala63 or Ala89 of SEQ ID NO:1 or at an equivalent amino acid of SEQ ID NO:8, SEQ ID NO:9, SEQ ID NO:10 or SEQ ID NO:11. In some embodiments, the mutated isopentenyl phosphate kinase includes a size reducing amino acid substitution mutation at Val62, Ala63 or Ala89, and a size reducing amino acid substitution mutation at Ile86, Met90 or Ile156 of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size increasing amino acid substitution mutation at Ala63 or Ala89 of SEQ ID NO:1 or at an equivalent amino acid of SEQ ID NO:8, SEQ ID NO:9, SEQ ID NO:10 or SEQ ID NO:11. In some embodiments, the mutated isopentenyl phosphate kinase includes a size increasing amino acid substitution mutation at Ala63 or Ala89, and a size reducing amino acid substitution mutation at Ile86, Met90 or Ile156 of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Met90, Ile86, Ile156, Ile146, Phe76, Phe83, Tyr154 or Met79 of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Met90, Ile156, Ile86 or Ile146 of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Phe76, Phe83 and Met79 of SEQ ID NO:1 or at an equivalent amino acid of SEQ ID NO:8, SEQ ID NO:9, SEQ ID NO:10 or SEQ ID NO:11. In some embodiments, the mutated isopentenyl phosphate kinase includes a size reducing amino acid substitution mutation at Phe76, Phe83 and Met79, and a size reducing amino acid substitution mutation at Met90, Ile156, Ile86 or Ile146 of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Tyr154 of SEQ ID NO:1 or at an equivalent amino acid of SEQ ID NO:8, SEQ ID NO:9, SEQ ID NO:10 or SEQ ID NO:11. In some embodiments, the mutated isopentenyl phosphate kinase includes a size reducing amino acid substitution mutation at Tyr154, and a size reducing amino acid substitution mutation at Met90, Ile156, Ile86 or Ile146, of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a mutation at Met90, Ile86, Ile146, Ile156, Ala63, Leu67 or Tyr66 of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Met90, Ile156, Ile86 or Ile146 of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Ala63 or a size increasing amino acid substitution mutation at Ala63 of SEQ ID NO:1 or at an equivalent amino acid of SEQ ID NO:8, SEQ ID NO:9, SEQ ID NO:10 or SEQ ID NO:11. In some embodiments, the mutated isopentenyl phosphate kinase includes a size reducing amino acid substitution mutation at Ala63 or a size increasing amino acid substitution mutation at Ala63, and a size reducing amino acid substitution mutation at Met90, Ile156, Ile86 or Ile146 of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Leu67 and Tyr66 of SEQ ID NO:1 or at an equivalent amino acid of SEQ ID NO:8, SEQ ID NO:9, SEQ ID NO:10 or SEQ ID NO:11. In some embodiments, the mutated isopentenyl phosphate kinase includes a size reducing amino acid substitution mutation at Leu67 and Tyr66, and a size reducing amino acid substitution mutation at Met90, Ile156, Ile86 or Ile146, of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a mutation at Ile146, Ile156, Ala63, Phe76 or Leu67 of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Ile146 and Ile156 of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size increasing amino acid substitution mutation at Ala63 of SEQ ID NO:1 or at an equivalent amino acid of SEQ ID NO:8, SEQ ID NO:9, SEQ ID NO:10 or SEQ ID NO:11. In some embodiments, the mutated isopentenyl phosphate kinase includes a size increasing amino acid substitution mutation at Ala63, and a size reducing amino acid substitution mutation at Ile146 and Ile156, of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Leu67 and Phe76 of SEQ ID NO:1 or at an equivalent amino acid of SEQ ID NO:8, SEQ ID NO:9, SEQ ID NO:10 or SEQ ID NO:11. In some embodiments, the mutated isopentenyl phosphate kinase includes a size reducing amino acid substitution mutation at Leu67 and Phe76, and a size reducing amino acid substitution mutation at Ile146 and Ile156, of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Ile86, Ile146, Ile156, Ala63, Met90, Leu67 and Phe76 of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Ile86, Ile146, or Ile156 of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Met90 and Ala63 of SEQ ID NO:1 or at an equivalent amino acid of SEQ ID NO:8, SEQ ID NO:9, SEQ ID NO:10 or SEQ ID NO:11. In some embodiments, the mutated isopentenyl phosphate kinase includes a size reducing amino acid substitution mutation at Met90 and Ala63, and a size reducing amino acid substitution mutation at Ile86, Ile146, or Ile156, of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Leu67 and Phe76 of SEQ ID NO:1 or at an equivalent amino acid of SEQ ID NO:8, SEQ ID NO:9, SEQ ID NO:10 or SEQ ID NO:11. In some embodiments, the mutated isopentenyl phosphate kinase includes a size reducing amino acid substitution mutation at Leu67 and Phe76, and a size reducing amino acid substitution mutation at Ile86, Ile146, or Ile156, of SEQ ID NO:1 or at an equivalent amino acid of SEQ ID NO:8, SEQ ID NO:9, SEQ ID NO:10 or SEQ ID NO:11.

In some embodiments, the amino acids His60, Val62, Ala63, Tyr66, Leu67, Phe76, Met79, Phe83, Ile86, Ala89, Met90, Ile146, Ile156 and/or Tyr154, of SEQ ID NO:1 or an equivalent amino acid of SEQ ID NO:8, SEQ ID NO:9, SEQ ID NO:10 or SEQ ID NO:11, form part of an active site of an isopentenyl phosphate kinase (also referred to herein as an isopentenyl phosphate active site). The isopentenyl phosphate active site is readily identifiable in any homolog of an isopentenyl phosphate kinase sequence listed herein. Thus, using the teachings herein and methods known in the art, one of skill may routinely identify the isopentenyl phosphate active site of any isopentenyl phosphate kinase homolog. Having identified the isopentenyl phosphate active site, using the teachings herein and methods known in the art, one of skill may routinely identify amino acids homologous to those listed above that may be mutated in order to form a mutated isopentenyl phosphate kinase for use in the methods described herein. Thus, in some embodiments, the mutated isopentenyl phosphate kinase includes one or more mutations at a position homologous to the following positions of an isopentenyl phosphate kinase sequence listed below in a homologous isopentenyl phosphate kinase: Val62, Ala63, Tyr66, Leu67, Phe76, Met79, Phe83, Ile86, Ala89, Met90, Ile146, Ile156 and/or Tyr154 of SEQ ID NO:1, or an equivalent amino acid of SEQ ID NO:8, SEQ ID NO:9, SEQ ID NO:10 or SEQ ID NO:11. In another embodiment, the mutated isopentenyl phosphate kinase includes a mutation at an amino acid position within the isopentenyl phosphate active site.

In some embodiments, the mutated isopentenyl phosphate kinase includes a size reducing amino acid substitution mutation at Ala63 (e.g. Ala63Gly). In certain embodiments, the mutated isopentenyl phosphate kinase includes a size reducing amino acid substitution mutation at Ile86 (e.g. Ile86Gly) and/or Ile146 (e.g. Ile146Gly). In certain embodiments, the mutated isopentenyl phosphate kinase includes a size reducing amino acid substitution mutation at Ile86 (e.g. Ile86Gly), Ile146 (e.g. Ile146Gly) and or Phe83 (e.g. Phe83Ala). In other embodiments, the mutated isopentenyl phosphate kinase includes a size increasing amino acid substitution mutation at Ile86 and a size reducing amino acid substitution mutation at Ile156 (e.g. Ile156Ala) and/or a size reducing amino acid substitution mutation at Phe76 (e.g. Phe76Ala).

In some embodiments, His60 is mutated such that the side chain moiety is increased in length. Thus, in some embodiments the His60 side chain is mutated such that the side chain methylene is changed to an unsubstituted $C_2$ to $C_{20}$ alkylene, an unsubstituted $C_2$ to $C_{10}$ alkylene, an unsubstituted $C_2$ to $C_8$ alkylene, an unsubstituted $C_2$ to $C_7$ alkylene, an unsubstituted $C_2$ to $C_6$ alkylene, an unsubstituted $C_2$ to $C_5$ alkylene, an unsubstituted $C_2$ to $C_4$ alkylene, or an unsubstituted $C_2$ to $C_3$ alkylene.

Also provided are nucleic acids encoding a mutated isopentenyl phosphate kinase described herein, nucleic acids that hybridize (e.g. under stringent hybridization conditions or moderately stringent hybridization conditions) to a nucleic acid encoding a mutated isopentenyl phosphate kinase described herein, and nucleic acids that have 60%, 65%, 70%, 75%, 80%, 85%, 86%, 87%, 88%, 89%, 90%, 91%, 92%, 93%, 94%, 95%, 96%, 97%, 98%, 99% or 100% sequence identity to a 25, 50, 100, 150, 200 or 250 contiguous nucleotide sequence or the entire nucleotide sequence of a nucleic acid encoding a mutated isopentenyl phosphate kinase described herein.

V. Methods of Designing Mutated Isopentenyl Phosphate Kinases

In another aspect, there is provided a method of identifying an amino acid substitution in an isopentenyl phosphate kinase that increases isoprenoid diphosphate formation rate. The method is useful, for example, in designing mutated isopentenyl phosphate kinases provided herein. The method includes determining a hypothetical binding position of an isoprenoid monophosphate within an active site of a first isopentenyl phosphate kinase using a computer modeling program. The method further includes, based on the hypothetical binding position, making a test mutated isopentenyl phosphate kinase including an amino acid substitution relative to the first isopentenyl phosphate kinase. The method further includes contacting the test mutated isopentenyl phosphate kinase with an isoprenoid monophosphate and a phosphate donor and determining a first rate of formation of an isoprenoid diphosphate. The method further includes comparing the first rate of formation of the isoprenoid diphosphate with a second rate of formation, wherein the second rate of formation is determined by contacting the first isopentenyl phosphate kinase with the isoprenoid monophosphate and the phosphate donor, wherein a higher first rate of formation relative to the second rate of formation indicates that the amino acid substitution increases isoprenoid diphosphate formation rate.

Applicable isoprenoid monophosphates are described in more detail below. For example, in some embodiments, the isoprenoid monophosphate is dimethylallyl monophosphate or an oligoprenyl monophosphate. In some embodiments, the oligoprenyl monophosphate is geranyl (C10) monophosphate, farnesyl (C15) monophosphate, geranylgeranyl (C20) monophosphate, C25 monophosphate, C30 monophosphate, C35 monophosphate, C40 monophosphate, C45 monophosphate, or C50 monophosphate.

In some embodiments, as described below, the isoprenoid monophosphate comprises one or more non-isoprenyl moieties. "Non-isoprenyl moiety" refers in the customary sense to a moiety which is not a prenyl moiety. In some embodiments, the non-isoprenyl moieties are selected from the group consisting of alkyl, alkenyl and alkynyl moieties.

In some embodiments, as described below, the isoprenoid monophosphate comprises a detectable label. In some embodiments, the detectable label is selected from the group consisting of fluorescent label, luminescent label, radioactive label, spectroscopic label, stable isotope mass tagged label, electron spin resonance label, nuclear magnetic resonance label and chelated metal label.

In some embodiments, as described below, the phosphate donor compound is a nucleotide triphosphate. In some embodiments, the phosphate donor compound is a nucleotide triphosphate which includes a detectable label. In some embodiments, the detectable label is selected from the group consisting of fluorescent label, luminescent label, radioactive label, spectroscopic label, stable isotope mass tagged label, electron spin resonance label, nuclear magnetic resonance label and chelated metal label. In some embodiments, the detectable label is a radioactive label or a fluorescent label. In some embodiments, the phosphate donor compound is ATPγS$^{35}$ or ATP$^{32}$.

VI. Methods of Synthesizing Isoprenoid Diphosphates

Provided herein are methods of synthesizing isoprenoid diphosphates or analogs thereof. In some embodiments, a method of synthesizing an isoprenoid diphosphate is provided. The method includes contacting an isoprenoid monophosphate and a phosphate donor with a mutated isopentenyl phosphate kinase (e.g. as described above such as an isolated mutated isopentenyl phosphate kinase) thereby forming an isoprenoid diphosphate. In certain embodiments, the method includes contacting an isoprenoid monophosphate or analog thereof and a phosphate or phosphate analog donor with a mutated isopentenyl phosphate kinase thereby forming an isoprenoid diphosphate or an isoprenoid diphosphate analog.

In some embodiments of the method of synthesizing isoprenoid diphosphates provided herein, the isoprenoid monophosphate is not isopentenyl monophosphate. In some embodiments, the phosphate donor is ATP or ATPγS.

In some embodiments, as described above, the mutated isopentenyl phosphate kinase has at least 90% sequence identity to a 200 contiguous amino acid sequence set forth in SEQ ID NO:1, SEQ ID NO:8, SEQ ID NO:9, SEQ ID NO:10 or SEQ ID NO:11. The mutated isopentenyl phosphate kinase includes one or more mutations according to the teachings provided herein (e.g. the description of the mutated isopentenyl phosphate kinases described above and in the Examples section below). For example, in some embodiments, the mutated isopentenyl phosphate kinase includes substitution, addition or deletion of one or more of the following amino acids: Val62, Ala63, Tyr66, Leu67, Phe76, Met79, Phe83, Ile86, Ala89, Met90, Ile146, Ile156 and/or Tyr154 of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a mutation at Val62, Ala63, Tyr66, Leu67, Phe76, Met79, Phe83, Ile86, Ala89, Met90, Ile146, Ile156 or Tyr154 of SEQ ID NO:1 or at an equivalent amino acid of SEQ ID NO:8, SEQ ID NO:9, SEQ ID NO:10 or SEQ ID NO:11. In some embodiments, the mutations at Val62, Tyr66, Leu67, Phe76, Met79, Phe83, Ile86, Met90, Ile146, Ile156 and Tyr154 are independently a size reducing amino acid substitution mutation. In some embodiments, mutation at Ala63 and Ala89 are independently a size reducing amino acid substitution mutation or a size increasing amino acid substitution mutation.

In some embodiments, the mutated isopentenyl phosphate kinase includes a size reducing amino acid substitution mutation at I86, F83, I146 or I156 of SEQ ID NO:1 or at an equivalent amino acid of SEQ ID NO:8, SEQ ID NO:9, SEQ ID NO:10 or SEQ ID NO:11. In some embodiments, the mutated isopentenyl phosphate kinase includes a mutation at Val62, Ile86, Met90, Ala63, Ala89 or Ile156 of SEQ ID NO:1 or at an equivalent amino acid of SEQ ID NO:8, SEQ ID NO:9, SEQ ID NO:10 or SEQ ID NO:1.

In some embodiments, the mutated isopentenyl phosphate kinase includes a size reducing amino acid substitution mutation at Ile86, Met90 or Ile156 of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Val62, Ala63 or Ala89 of SEQ ID NO:1 or at an equivalent amino acid of SEQ ID NO:8, SEQ ID NO:9, SEQ ID NO:10 or SEQ ID NO:11. In some embodiments, the mutated isopentenyl phosphate kinase includes a size reducing amino acid substitution mutation at Val62, Ala63 or Ala89, and a size reducing amino acid substitution mutation at Ile86, Met90 or Ile156 of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size increasing amino acid substitution mutation at Ala63 or Ala89 of SEQ ID NO:1 or at an equivalent amino acid of SEQ ID NO:8, SEQ ID NO:9, SEQ ID NO:10 or SEQ ID NO:11. In some embodiments, the mutated isopentenyl phosphate kinase includes a size increasing amino acid substitution mutation at Ala63 or Ala89, and a size reducing amino acid substitution mutation at Ile86, Met90 or Ile156 of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Met90, Ile86, Ile156, Ile146, Phe76, Phe83, Tyr154 or Met79 of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Met90, Ile156, Ile86 or Ile146 of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Phe76, Phe83 and Met79 of SEQ ID NO:1 or at an equivalent amino acid of SEQ ID NO:8, SEQ ID NO:9, SEQ ID NO:10 or SEQ ID NO:11. In some embodiments, the mutated isopentenyl phosphate kinase includes a size reducing amino acid substitution mutation at Phe76, Phe83 and Met79, and a size reducing amino acid substitution mutation at Met90, Ile156, Ile86 or Ile146 of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Tyr154 of SEQ ID NO:1 or at an equivalent amino acid of SEQ ID NO:8, SEQ ID NO:9, SEQ ID NO:10 or SEQ ID NO:11. In some embodiments, the mutated isopentenyl phosphate kinase includes a size reducing amino acid substitution mutation at Tyr154, and a size reducing amino acid substitution mutation at Met90, Ile156, Ile86 or Ile146, of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a mutation at Met90, Ile86, Ile146, Ile156, Ala63, Leu67 or Tyr66 of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Met90, Ile156, Ile86 or Ile146 of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Ala63 or a size increasing amino acid substitution mutation at Ala63 of SEQ ID NO:1 or at an equivalent amino acid of SEQ ID NO:8, SEQ ID NO:9, SEQ ID NO:10 or SEQ ID NO:11. In some embodiments, the mutated isopentenyl phosphate kinase includes a size reducing amino acid substitution mutation at Ala63 or a size increasing amino acid substitution mutation at Ala63, and a size reducing amino acid substitution mutation at Met90, Ile156, Ile86 or Ile146, of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Leu67 and Tyr66 of SEQ ID NO:1 or at an equivalent amino acid of SEQ ID NO:8, SEQ ID NO:9, SEQ ID NO:10 or SEQ ID NO:11. In some embodiments, the mutated isopentenyl phosphate kinase includes a size reducing amino acid substitution mutation at Leu67 and Tyr66, and a size reducing amino acid substitution mutation at Met90, Ile156, Ile86 or Ile146, of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a mutation at Ile146, Ile156, Ala63, Phe76 or Leu67 of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Ile146 and Ile156 of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size increasing amino acid substitution mutation at Ala63 of SEQ ID NO:1 or at an equivalent amino acid of SEQ ID NO:8, SEQ ID NO:9, SEQ ID NO:10 or SEQ ID NO:11. In some embodiments, the mutated isopentenyl phosphate kinase includes a size increasing amino acid substitution mutation at Ala63, and a size reducing amino acid substitution mutation at Ile146 and Ile156, of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Leu67 and Phe76 of SEQ ID NO:1 or at an equivalent amino acid of SEQ ID NO:8, SEQ ID NO:9, SEQ ID NO:10 or SEQ ID NO:11. In some embodiments, the mutated isopentenyl phosphate kinase includes a size reducing amino acid substitution mutation at Leu67 and Phe76, and a size reducing amino acid substitution mutation at Ile146 and Ile156, of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Ile86, Ile146, Ile156, Ala63, Met90, Leu67 and Phe76 of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Ile86, Ile146, or Ile156 of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Met90 and Ala63 of SEQ ID NO:1 or at an equivalent amino acid of SEQ ID NO:8, SEQ ID NO:9, SEQ ID NO:10 or SEQ ID NO:11. In some embodiments, the mutated isopentenyl phosphate kinase includes a size reducing amino acid substitution mutation at Met90 and Ala63, and a size reducing amino acid substitution mutation at Ile86, Ile146, or Ile156, of SEQ ID NO:1 or at an equivalent amino acid of SEQ ID NO:8, SEQ ID NO:9, SEQ ID NO:10 or SEQ ID NO:11.

In some embodiments, the mutated isopentenyl phosphate kinase includes a size reducing amino acid substitution mutation at Leu67 and Phe76 of SEQ ID NO:1 or at an equivalent amino acid of SEQ ID NO:8, SEQ ID NO:9, SEQ ID NO:10 or SEQ ID NO:11. In some embodiments, the mutated isopentenyl phosphate kinase includes a size reducing amino acid substitution mutation at Leu67 and Phe76, and a size reducing amino acid substitution mutation at Ile86, Ile146, or Ile156, of SEQ ID NO:1 or at an equivalent amino acid of SEQ ID NO:8, SEQ ID NO:9, SEQ ID NO:10 or SEQ ID NO:11.

In some embodiments, where the mutations in the preceding paragraphs are employed, the isoprenoid monophosphate is farnesyl ($C_{15}$) monophosphate.

In some embodiments, the mutated isopentenyl phosphate kinase includes a size reducing amino acid substitution mutation at Ala63 (e.g. Ala63Gly). In certain embodiments, the mutated isopentenyl phosphate kinase includes a size reducing amino acid substitution mutation at Ile86 (e.g. Ile86Gly) and/or Ile146 (e.g. Ile146Gly). In certain embodiments, the mutated isopentenyl phosphate kinase includes a size reducing amino acid substitution mutation at Ile86 (e.g. Ile86Gly), Ile146 (e.g. Ile146Gly) and or Phe83 (e.g. Phe83Ala). In other embodiments, the mutated isopentenyl phosphate kinase includes a size increasing amino acid substitution mutation at Ile86 and a size reducing amino acid substitution mutation at Ile156 (e.g. Ile156Ala) and/or a size reducing amino acid substitution mutation at Phe76 (e.g. Phe76Ala). In some embodiments, His60 is mutated such that the side chain moiety is increased in length. Thus, in some embodiments the His60 side chain is mutated such that the side chain methylene is changed to an unsubstituted $C_2$ to $C_{20}$ alkylene, an unsubstituted $C_2$ to $C_{10}$ alkylene, an unsubstituted $C_2$ to $C_8$ alkylene, an unsubstituted $C_2$ to $C_7$ alkylene, an unsubstituted $C_2$ to $C_6$ alkylene, an unsubstituted $C_2$ to $C_s$ alkylene, an unsubstituted $C_2$ to $C_4$ alkylene, or an unsubstituted $C_2$ to $C_3$ alkylene. In some embodiments, where the mutations in the this paragraph are employed, the isoprenoid monophosphate is geranyl ($C_{10}$) monophosphate.

In some embodiments, the isoprenoid monophosphate is dimethylallyl monophosphate, isopentenyl monophosphate or an extended prenyl monophosphate. The term "extended prenyl monophosphate," used herein, is a compound having the following formula:

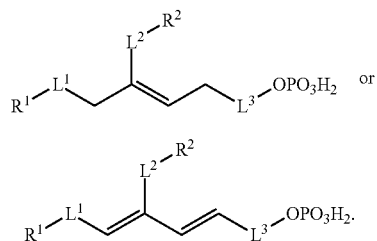

A person having ordinary skill in the art will immediately recognize that the phosphate moiety in Formulae I and II may equally exist in base form (or salt thereof). In Formula I and II, $R^1$ and $R^2$ are independently a hydrogen, detectable label, —CN, —OH, —COOH, halogen, —NH$_2$, —SH, substituted or unsubstituted alkyl (e.g. substituted or unsubstituted $C_1$ to $C_{50}$ alkyl), substituted or unsubstituted heteroalkyl (e.g. substituted or unsubstituted 2 to 50 membered heteroalkyl), substituted or unsubstituted cycloalkyl (e.g. substituted or unsubstituted $C_3$ to $C_8$ cycloalkyl), substituted or unsubstituted heterocycloalkyl (e.g. substituted or unsubstituted 3 to 8 membered heterocycloalkyl), substituted or unsubstituted aryl (e.g. substituted or unsubstituted $C_6$ aryl), or substituted or unsubstituted heteroaryl (e.g. substituted or unsubstituted 6 membered heteroaryl). Exemplary detectable labels include, but are limited to, fluorescent labels, luminescent labels, spectroscopic labels, stable isotope mass tagged labels, electron spin resonance labels, nuclear magnetic resonance labels and chelated metal labels.

$L^1$, $L^2$ and $L^3$ are independently a bond, substituted or unsubstituted alkylene (e.g. substituted or unsubstituted $C_1$ to $C_{50}$ alkylene), substituted or unsubstituted heteroalkylene (e.g. substituted or unsubstituted 2 to 50 membered heteroalkylene), substituted or unsubstituted cycloalkylene (e.g. substituted or unsubstituted $C_3$ to $C_8$ cycloalkylene), substituted or unsubstituted heterocycloalkylene (e.g. substituted or unsubstituted 3 to 8 membered heterocycloalkylene), substituted or unsubstituted arylene (e.g. substituted or unsubstituted $C_6$ arylene), or substituted or unsubstituted heteroarylene (e.g. substituted or unsubstituted 6 membered heteroarylene). In some embodiments, in Formula I and II, at least one of $R^1$ and $R^2$ is not hydrogen, or at least one of $L^1$, $L^2$ or $L^3$ is not a bond.

In some embodiments, $R^1$ and $R^2$ are independently a hydrogen, a detectable label, —CN, —OH, —COOH, halogen, —NH$_2$, —SH, $R^4$-substituted or unsubstituted alkyl, $R^4$-substituted or unsubstituted heteroalkyl, $R^4$-substituted or unsubstituted cycloalkyl, $R^4$-substituted or unsubstituted aryl or $R^4$-substituted or unsubstituted heteroaryl. $R^4$ is independently a detectable label, —CN, —OH, —COOH, halogen, —NH$_2$, —SH, $R^5$-substituted or unsubstituted alkyl (e.g. $R^5$-substituted or unsubstituted $C_1$ to $C_{50}$ alkyl), $R^5$-substituted or unsubstituted heteroalkyl (e.g. $R^5$-substituted or unsubstituted 2 to 50 membered heteroalkyl), $R^5$-substituted or unsubstituted cycloalkyl (e.g. $R^5$-substituted or unsubstituted $C_3$ to $C_8$ cycloalkyl), $R^5$-substituted or unsubstituted aryl (e.g. $R^5$-substituted or unsubstituted $C_6$ aryl) or $R^5$-substituted or unsubstituted heteroaryl (e.g. $R^5$-substituted or unsubstituted 6 membered heteroaryl). $R^5$ is independently a detectable label, —CN, —OH, —COOH, halogen, —NH$_2$, —SH, unsubstituted alkyl (e.g. unsubstituted $C_1$ to $C_{50}$ alkyl), unsubstituted heteroalkyl (e.g. unsubstituted 2 to 50 membered heteroalkyl), unsubstituted cycloalkyl (e.g. unsubstituted $C_3$ to $C_8$ cycloalkyl), unsubstituted heterocycloalkyl (e.g. unsubstituted 3 to 8 membered heterocycloalkyl), unsubstituted aryl (e.g. unsubstituted $C_6$ aryl) or unsubstituted heteroaryl (e.g. unsubstituted 6 membered heteroaryl).

In certain embodiments, $R^1$ and $R^2$ are independently hydrogen, a detectable label or $R^4$-substituted or unsubstituted alkyl. $R^4$ may independently be a detectable label or $R^5$-substituted or unsubstituted alkyl. $R^5$ may independently be unsubstituted alkyl or a detectable label.

In certain embodiments, $R^2$ is hydrogen. In certain embodiments, $R^2$ is hydrogen and $L^2$ is a bond. $L^3$ may also be a bond. $L^1$, $L^2$ and $L^3$ may independently be a bond, $R^3$-substituted or unsubstituted alkylene (e.g. $R^3$-substituted or unsubstituted $C_1$ to $C_{50}$ alkylene), $R^3$-substituted or unsubstituted heteroalkylene (e.g. $R^3$-substituted or unsubstituted 2 to 50 membered heteroalkylene), $R^3$-substituted or unsubstituted cycloalkylene (e.g. $R^3$-substituted or unsubstituted $C_3$ to $C_8$ cycloalkylene), $R^3$-substituted or unsubstituted heterocycloalkyl (e.g. $R^3$-substituted or unsubstituted 3 to 8 membered heterocycloalkylene), $R^3$-substituted or unsubstituted aryl (e.g. $R^3$-substituted or unsubstituted $C_6$ arylene) or $R^3$-substituted or unsubstituted heteroaryl (e.g. $R^3$-substituted or unsubstituted 6 membered heteroarylene). $R^3$ may independently be a detectable label, —CN, —OH, —COOH, halogen, —NH$_2$, —SH, $R^4$-substituted or unsubstituted alkyl (e.g. $R^4$-substituted or unsubstituted $C_1$ to $C_{50}$ alkyl), $R^4$-substituted or unsubstituted heteroalkyl (e.g. $R^4$-substituted or unsubstituted 2 to 50 membered heteroalkyl), $R^4$-substituted or unsubstituted cycloalkyl (e.g. $R^4$-substituted or unsubstituted $C_3$ to $C_8$ cycloalkyl), $R^4$-substituted or unsubstituted aryl (e.g. $R^4$-substituted or unsubstituted $C_6$ aryl) or $R^4$-substituted or unsubstituted heteroaryl (e.g. $R^4$-substituted or unsubstituted 6 membered heteroaryl).

In certain embodiments, $L^1$, $L^2$ and $L^3$ are independently a bond or detectable label or $R^3$-substituted or unsubstituted alkylene. $R^3$ may independently be a detectable label or $R^4$-substituted or unsubstituted alkyl. $R^4$ may independently be unsubstituted alkyl (e.g. unsubstituted $C_1$ to $C_{50}$ alkyl) or a detectable label.

Where $L^1$, $L^2$, $L^3$, $R^1$, $R^2$, $R^3$, $R^4$, and/or $R^5$ are alkyl, the alkyl may include at least one prenyl subunit. A prenyl subunit has the formula below and follows the normal rules of valency when incorporated into $L^1$, $L^2$, $L^3$, $R^1$, $R^2$, $R^3$, $R^4$, and/or $R^5$:

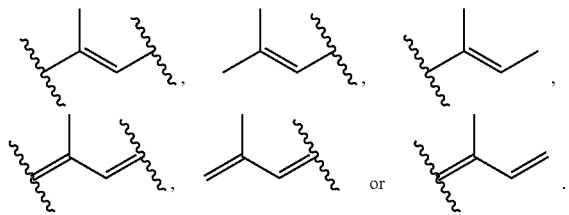

In some embodiments, the extended prenyl monophosphate is a substituted or unsubstituted oligoprenyl monophosphate. A substituted or unsubstituted oligopenyl monophosphate includes a substituted or unsubstituted oligoprenyl chain covalently bound to a phosphate. A substituted oligoprenyl chain two or more substituted prenyl subunits covalently bound together in a linear fashion where at least one of the prenyl subunits is substituted. A substituted oligoprenyl chain includes two or more unsubstituted prenyl subunits (shown above) covalently bound together in a linear fashion.

In some embodiments, the unsubstituted oligoprenyl monophosphate is geranyl ($C_{10}$) monophosphate, farnesyl ($C_{15}$) monophosphate, geranylgeranyl ($C_{20}$) monophosphate, or higher order oligomers each differing by 5-carbons, for example, $C_{25}$ monophosphate, $C_{30}$ monophosphate, $C_{35}$ monophosphate, $C_{40}$ monophosphate, $C_{45}$ monophosphate or $C_{50}$ monophosphate. In certain embodiments, the unsubstituted oligoprenyl monophosphate is geranyl ($C_{10}$) monophosphate. The unsubstituted oligoprenyl monophosphate may also be farnesyl ($C_{15}$) monophosphate.

In some embodiments, the isoprenoid monophosphate includes one or more non-isoprenyl moieties. "Non-isoprenyl moiety" refers in the customary sense to a moiety which is not a prenyl moiety. In some embodiments, the non-isoprenyl moieties are selected from the group consisting of alkyl, alkenyl and alkynyl moieties. In some embodiments, the isoprenoid monophosphate includes a detectable label as described herein. In some embodiments, the detectable label is selected from the group consisting of fluorescent label, luminescent label, radioactive label, spectroscopic label, stable isotope mass tagged label, electron spin resonance label, nuclear magnetic resonance label and chelated metal label.

In some embodiments, the extended prenyl monophosphate is a substituted oligoprenyl monophosphate. In some embodiments, the substituted oligoprenyl monophosphate is $R^3$-substituted oligoprenyl monophosphate (i.e. an oligoprenyl monophosphate substituted with one or more optionally different $R^3$ moieties). It is understood that a large number of possible unlabeled and labeled oligoprenyl chains can be accessed by the artisan skilled in the art of organic chemical synthesis. In some embodiment, $R^3$ is detectable label or an unsubstituted alkyl (either fully or partially saturated). In some embodiment, $R^3$ is detectable label or an unsubstituted alkyl including one or more double or triple bonds.

An isoprenoid diphosphate is an isoprenoid monophosphate in which the monophosphate of the isoprenoid monophosphate is replaced with a diphosphate. Therefore, the description above regarding isoprenoid monophosphates is equally applicable to the isoprenoid diphosphates referred to herein.

The phosphate donor compound is typically a nucleotide triphosphate. Nucleotide triphosphate compounds may include a detectable label. In some embodiments, the phosphate donor compound is a nucleotide triphosphate analog comprising a detectable label. Useful detectable labels include fluorescent labels, luminescent labels, radioactive labels, spectroscopic labels, stable isotope mass tagged labels, electron spin resonance labels, nuclear magnetic resonance labels and chelated metal labels. In some embodiments, the detectable label is a radioactive label or a fluorescent label. For example, the nucleotide triphosphate may be ATPγS$^{35}$ or ATP$^{32}$. One of skill will recognize that a labeled phosphate donor compound results in a labeled isoprenoid diphosphate.

In some embodiments, each substituted group described above for the compounds of the present invention is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described above is substituted with at least one substituent group. In other embodiments, at least one or all of these groups are substituted with at least one size-limited substituent group. Alternatively, at least one or all of these groups are substituted with at least one lower substituent group.

In other embodiments of the compounds described above, each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, each substituted or unsubstituted heterocycloalkyl is a substituted or unsubstituted 4 to 8 membered heterocycloalkyl, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_4$-$C_8$ cycloalkylene, and each substituted or unsubstituted heterocycloalkylene is a substituted or unsubstituted 4 to 8 membered heterocycloalkylene.

Alternatively, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, each substituted or unsubstituted heterocycloalkyl is a substituted or unsubstituted 5 to 7 membered heterocycloalkyl, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_5$-$C_7$ cycloalkylene, and each substituted or unsubstituted heterocycloalkylene is a substituted or unsubstituted 5 to 7 membered heterocycloalkylene.

EXAMPLES

The following examples illustrate certain specific embodiments of the invention and are not meant to limit the scope of the invention.

Example 1

X-Ray Crystallographic Analysis of IPK

Introduction

Disclosed herein, the crystal structure of IPK from *M. jannaschii* (SEQ ID NO:1) was solved to 2.0 Å resolution. An active site histidine residue (His60) was found to stabilize the terminal phosphate of both substrate and product complexes. This residue structurally aligns with members of the family that phosphorylate a phosphate or phosphonate functional group; other members of the family show no residue at this position. See FIG. 8. Through structural observation, mutation, and kinetic analysis, IPK His60 was found to serve a critical role in substrate, product, and transition state stabilization. We report not only the newest structural member to the amino acid kinase superfamily, but also demonstrate the first clear functional and structural division between family members.

Materials and Methods

Cloning of IPK Gene and Construction of Mutants

The IPK gene MJ0044 (Grochowski, et al., 2006, Id.) was amplified from *Methanocaldococcus jannaschii* genomic DNA (ATCC® 43067D-5™) by PCR. An IPK homolog from *Methanococcus maripaludis* was also amplified from genomic DNA (ATCC® BAA-1333D-5™) by PCR. Both genes were amplified using Phusion™ High-Fidelity DNA polymerase (New England Biolabs, Inc) with a 60° C. annealing temperature and a 30 second PCR extension time. The primer pairs for these reactions are listed in Table 2 following. The PCR products were digested with NcoI and XhoI (New England Biolabs, Inc), purified, and ligated into an NcoI/XhoI digested PHis8 vector (a modified version of pet28a containing an N-terminal 8-histidine tag) using T4 DNA ligase (New England Biolabs, Inc).

TABLE 2

Primer Pairs for PCR reactions

| Protein Name | Forward primer | Reverse Primer |
|---|---|---|
| IPK-Mjannaschii | 5'-cccatggcggatccatgctaaccatattaaaattaggagg-3' (SEQ ID NO: 12) | 5'-tggtggtgctcgagttattctgaaaaatcaatttctgttc-3' (SEQ ID NO: 13) |
| IPK-Mmaripaludis | 5'-gagggcggatcaaaattctaacgtttgtaaggtacccttggt-3' (SEQ ID NO: 14) | 5'-gtggtgctcgagttaatttattaatgttccttttacatttttt-3' (SEQ ID NO: 15) |
| IPK-Mjannaschii H60A | 5'-cgtccatggaggaggagcttttggtgctccagtagctaaa-3' (SEQ ID NO: 16) | 5'-tttagctactggagcaccaaaagctcctcctccatggacg-3' (SEQ ID NO: 17) |
| IPK-Mjannaschii H60N | 5'-atggaggaggagcttttggtaatccagtagctaaaaaatac-3 (SEQ ID NO: 18) | 5'-gtattttttagctactggattaccaaaagctcctcctccat-3' (SEQ ID NO: 19) |
| IPK-Mjannaschii H60Q | 5'-catggaggaggagcttttggtcagccagtagctaaa-3' (SEQ ID NO: 20) | 5'-tttagctactggctgaccaaaagctcctcctccatg-3 (SEQ ID NO: 21) |

The mutations at His60 of IPK from *M. jannaschii* were made using the Quikchange protocol with PfuTurbo® DNA Polymerase (Stratagene) and a 6.5 min PCR extension time. The primer pairs used to generate the mutants H60A, H60N, and H60Q are listed in Table 2.

Protein Expression and Purification

The plasmid containing the IPK gene (IPK-PHis8) was transformed into *E. coli* B121(DE3) competent cells (Novagen). One colony was grown up in LB media (75 ml) overnight at 37° C. After shaking for approximately 18 hours, 25 ml of the overnight culture was transferred into one liter of TB media and was grown at 37° C. until an $OD_{600}$ of 1.2 was reached. Isopropyl-β-D-thiogalactoside (0.2 mM) was then added and the cells were shaken overnight at 37° C. (approximately 12-14 hours post-induction). The cells were harvested by centrifugation and lysed using lysis buffer (50 mM TRIS HCl pH 8.0, 500 mM NaCl, 20 mM imidazole, 1% (v/v) TWEEN20, 10% (v/v) glycerol, 10 mM 2-mercaptoethanol) containing lysozyme (1 mg/ml). The lysate was stirred at 4° C. for one hour, sonicated 4 to 5 times (30 seconds total, 0.5 sec on, 1.0 sec off at 70% amplitude), and centrifuged at 21,000 RPM for 45min at 4° C. The supernatant was loaded onto a column containing Ni-NTA agarose resin (Qiagen), washed with lysis buffer and wash buffer (lysis buffer without TWEEN20), and then eluted with elution buffer (wash buffer containing 250 mM imidazole). The protein was digested with thrombin overnight in dialysis buffer (50 mM TRIS HCl pH 8.0, 100 mM NaCl) containing 10 mM 2-mercaptoethanol. The following day, the dialysate was run through a second column containing Benzamidine Sepharose™ 4 Fast Flow (high sub) (GE healthcare) and Ni-NTA agarose. The protein was heated at 80° C. for 10 minutes to precipitate most contaminating proteins and the supernatant was passed through a HiLoad™ 16/16 Superdex™ 200 prepgrade (GE healthcare) gel filtration column using dialysis buffer containing 2 mM DTT. Fractions were combined, concentrated to approximately 15 mg/ml, and frozen at −80° C. for future use.

Kinetic Analysis

All specific activity and kinetic measurements were performed using the pyruvate kinase-lactate dehydrogenase coupled assay with reference to a previously established protocol (Lindsley, 2001, *Methods Mol. Biol.* 95:57-64.). The reaction includes the following components in a 200 ul volume: 7 U pyruvate kinase, 10 U lactate dehydrogenase, 2 mM phosphoenolpyruvate, 0.16 mM NADH, 50 mM TRIS HCl pH 8.0, 100 mM KCl, 8 mM MgCl2, 4 mM ATP, and variable concentrations of IP (purchased from Larodan Fine Chemicals). The reaction was initiated by the addition of IPK (0.15 ug) and was followed by observing the depletion of NADH at 340 nm over time, expressed as $\Delta(AU_{340})/\Delta t$, which was converted to $\Delta(ADP)/\Delta t$. These values were then plotted against substrate concentration in GraphPad Prism® (Version 5.01 for Windows) to compute the kinetic parameters $k_{cat}$ and $K_m$ using the "nonlinear regression enzyme kinetic analysis" option.

Crystallization and Data Collection

Crystals of IPK were grown using the hanging-drop vapor-diffusion method with a 2 ul drop containing 1 ul of protein (15 mg/ml) and 1 ul of reservoir. Several hits were obtained in Hampton Crystal Screen I (Hampton Research) and were screened around to improve crystal morphology. Under optimized conditions, IPK crystals formed large plates in a reservoir condition containing 1.5-1.6M ammonium sulfate at 298 K. The plates were visible after 1-2 days and reached full size after 1 week. Crystal soaks were set up with heavy atoms (0.1-0.5 mM ethyl mercuric phosphate) or ligands (1 mM IP, 5 mM IPP, or 1 mM IP/5 mM ATPγS) by transferring a crystal into a new drop containing both the ligand and the original reservoir condition. After a soak time of 1-2 days, crystals were placed in a cryo-protectant (containing 2.0M ammonium sulfate and 20% ethylene glycol) for 10-30 sec and then flash frozen in liquid nitrogen.

X-ray data was collected at ALS beamlines 8.2.1 and 8.2.2 (Lawrence Berkeley National Laboratory, Berkeley, Calif.) using an ADSC Q315 CCD detector at 110K. All x-ray diffraction data (include SAD data) was collected at λ=1.0 Å.

Structure Solution and Refinement

All data was processed and scaled with XDS (Kabsch, 1993, *Journal of Applied Crystallography.* 26:795-800). The initial structure of IPK was solved using the SAD data collected from the IPK crystal soaked with ethyl mercuric phosphate. The programs SOLVE and RESOLVE (Terwilliger, 2004, *J. Synchrotron Radiat.* 11:49-52) were used to calculate heavy atom positions, compute phases, and perform auto-building and refinement cycles using REFMAC (Murshudov et al., 1997, *Acta Crystallogr. D Biol. Crystallogr.* 53:240-255; Collaborative Computational Project, Number 4., 1994, The CCP4 Suite: Programs for Protein Crystallography. *Acta Crystallogr. D Biol. Crystallogr.* 50:760-763). Additional model building and density improvement was accomplished through ARP/wARP (Perrakis et al., 1999, *Nat. Struct. Biol.* 6:458-463; Collaborative Computational Project, Number 4., 1994, Id.) The refined model was then used as the starting model in the refinement of all other x-ray data sets including the IP-bound structure, IPP-bound structure, and thio-IPP-bound structure. All of these structures were refined using both CNS and CCP4 program suites (Collaborative Computational Project, Number 4., 1994, Id.; Brunger et al., 1998, *Acta Crystallogr. D Biol. Crystallogr.* 54:905-921; Brunger, 2007, *Nat. Protoc.* 2:2728-2733). The program COOT was used for all map/model visualization and manual building (Emsley & Cowtan, 2004, *Acta Crystallogr. D Biol. Crystallogr.* 60:2126-2132). The data refinement statistics can be found in Table 3.

TABLE 3

| X-ray Diffraction Data Processing and Refinement Statistics | | | | |
|---|---|---|---|---|
| | IPK apo | IPK-IP complex | IPK-IPP complex | IPK-IPPβS complex |
| Data Collection and Processing | | | | |
| Space group | $P2_12_12$ | $P2_12_12$ | $P2_12_12$ | $P2_12_12$ |
| Resolution (Å) | 2.0 | 2.7 | 2.55 | 2.35 |
| Cell dimensions | | | | |
| a (Å) | 76.05 | 77.86 | 78.11 | 77.78 |
| b (Å) | 99.61 | 100.71 | 99.88 | 100.38 |

TABLE 3-continued

X-ray Diffraction Data Processing and Refinement Statistics

|  | IPK apo | IPK-IP complex | IPK-IPP complex | IPK-IPPβS complex |
|---|---|---|---|---|
| c (Å) | 87.60 | 87.21 | 87.58 | 88.10 |
| α = β = γ (°) | 90 | 90 | 90 | 90 |
| Molecules in asymmetric unit | 2 | 2 | 2 | 2 |
| # measured reflections | 280086 (41535) | 109680 (15190) | 128795 (17570) | 195455 (25991) |
| # unique reflections | 43888 (6469) | 18614 (2598) | 21910 (3104) | 27728 (3786) |
| Redundancy | 6.38 (6.42) | 5.89 (5.85) | 5.87 (5.66) | 7.05 (6.87) |
| Merging R-factor (%) | 6.9 (32.9) | 8.4 (38.5) | 7.9 (33.99) | 7.5 (39.8) |
| Completeness (%) | 95.6 (88.6) | 95.5 (84.5) | 95.5 (85.2) | 93.9 (80.9) |
| I/σ(I) | 16.23 (4.58) | 16.79 (3.70) | 16.52 (4.34) | 15.54 (3.84) |
| Refinement |  |  |  |  |
| Resolution range (Å) | 50.0-2.0 | 50.0-2.7 | 50.0-2.55 | 50.0-2.35 |
| # of reflections: |  |  |  |  |
| Total used | 42577 | 19306 | 22646 | 29186 |
| Working set | 40472 | 18323 | 21505 | 27724 |
| Test set | 2105 | 983 | 1141 | 1462 |
| # of atoms |  |  |  |  |
| R-factor | 0.2310 | 0.20820 | 0.21574 | 0.23340 |
| Free R-factor | 0.2493 | 0.26793 | 0.29601 | 0.28620 |
| # amino acid residues |  |  |  |  |
| # water molecules |  |  |  |  |
| Ramachandran plot: |  |  |  |  |
| Allowed (%) |  |  |  |  |
| Generously allowed (%) |  |  |  |  |
| Disallowed (%) |  |  |  |  |
| Refinement program | CNS, Refmac | CNS, Refmac | CNS, Refmac | CNS, Refmac |

Additional programs used to view, analyze, and manipulate structural data include the following: 1) SSM Superpose, a program within COOT that superimposes the Cα atoms of one structure onto another, generating an RMSD value between the two (Krissinel & Henrick, 2004, *Acta Crystallogr. D Biol. Crystallogr.* 60:2256-2268); 2) PyMOL, a molecular graphics program used to create images of the protein structure (DeLano, 2002, *The PyMOL Molecular Graphics System*, DeLano Scientific, Palo Alto, Calif., USA.); 3) Adobe Illustrator, used to label and manipulate images created with PyMOL.

IPK Mutant Reactions

IPK mutants (at a final concentration of 10 μM) were incubated in a 50 μl reaction with 150 μM farnesyl monophosphate (FP), 7 mM MgCl2, 4 mM ATP, and 50 mM TRIS.HCl pH 8.0 for 20 minutes at 55° C. 10 μl of this reaction was then added to a 500 μl reaction containing 45 ug of the terpene cyclase 5-epi-aristolochene synthase (TEAS) and 10 mM MgCl2 in a 3-component buffer system (25 mM MES, 50 mM TRIS.HCl, 25 mM CAPS) at pH 7.0. A method known as the "vial assay" (O'Maille et al., 2004, *Anal. Biochem.* 335:210-217) was employed by overlaying this aqueous layer with 500 μl of ethyl acetate, incubating overnight at 25° C., and vortexing to extract the terpene product into the organic layer prior to quantitative GC-MS analysis. Both negative and positive control reactions were conducted as follows. For the negative control, no IPK was added to the first reaction. For the positive control, 3 μM of FPP (equivalent to the amount that would be present assuming complete FP to FPP turnover) was added to the TEAS reaction.

Results and Discussion

Overall Fold

Isopentenyl phosphate kinase (IPK) represents the newest structural member to the amino acid kinase (AAK) superfamily (protein family Pf00696). It shares the fold that is commonly referred to as the open αβα sandwich, which was first discovered in carbamate kinase from *E. faecalis* (Marina et al., 1999, *Protein Sci.* 8:934-940). Among the structures representing this family, IPK is most structurally similar to FomA kinase from *S. wedmorensis* (rmsd of 2.0Å for superposition of Cα's, sequence identity of 22%), although it shares the highest sequence identity with uridylate kinase (UMPK) from *A. fulgidus* (25%). See FIG. 8. All three of these proteins utilize a substrate that is phosphorylated at a phosphate or phosphonate functional group; all other members of the family including carbamate kinase, acetylglutamate kinase, aspartokinase, and glutamate-5-kinase, are phosphorylated at the carbamate or carboxylate functional group of their respective substrate.

Figure 1C:
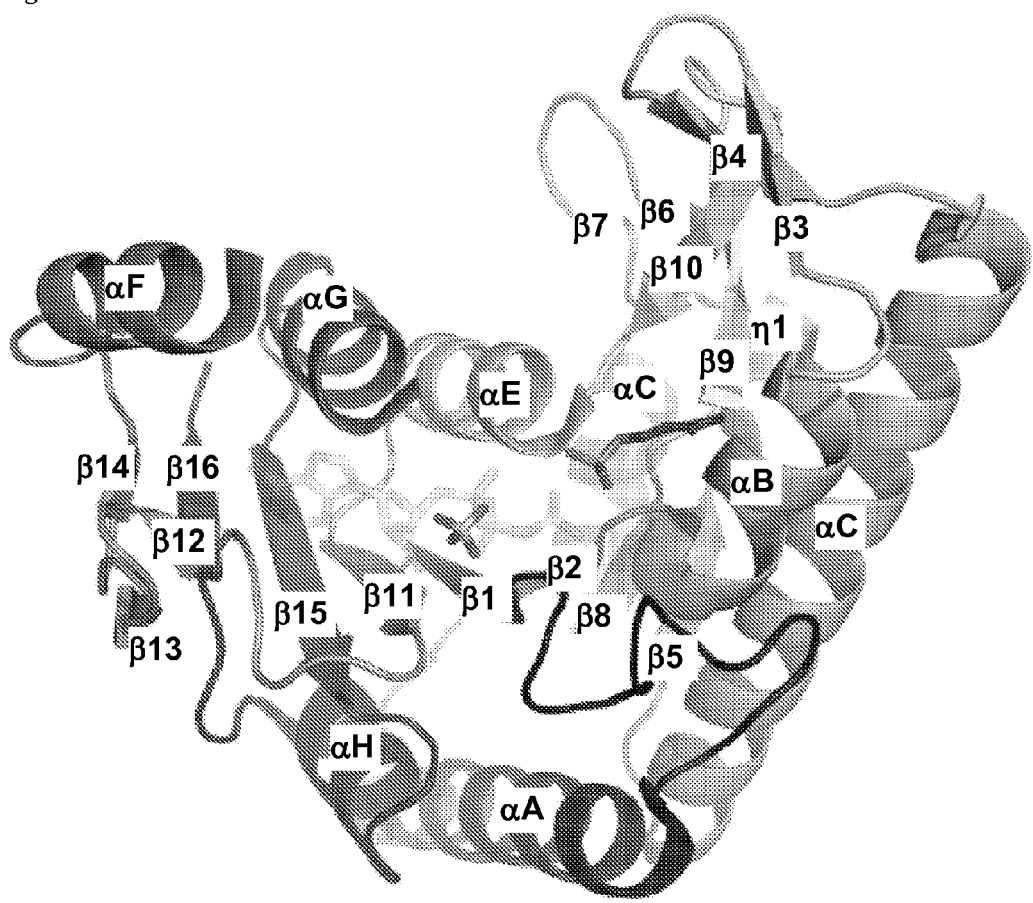
FIG. 1C: Ribbon diagram of the IPK monomer is depicted. The C-terminal ATP-binding domain contains a β-sulfate residing in a location coinciding with the β-phosphate of ATP. The ATP analog AMPPNP is visible (non-ribbon depiction) being modeled from Protein Database entry PDBID:1gs5, and serves as a reference for the putative location of ATP in IPK. The crystallographically observed isopentenyl phosphate (IP) substrate is shown bound within the N-terminal domain.
Figure 1D:
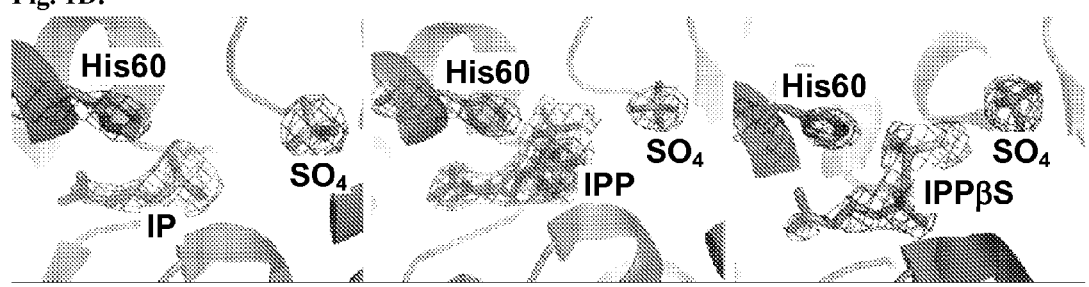
FIG. 1D: The active sites of IPK are depicted complexed with IP (left), IPP (middle), and IPPβS (right). Electron density surrounding each ligand (dark and light are contoured to 1σ and 0.6σ, respectively) shown as 2Fo-Fc omit electron density maps, where the ligands were removed before a round of refinement and subsequent phase and map calculations.
Figure 2A:
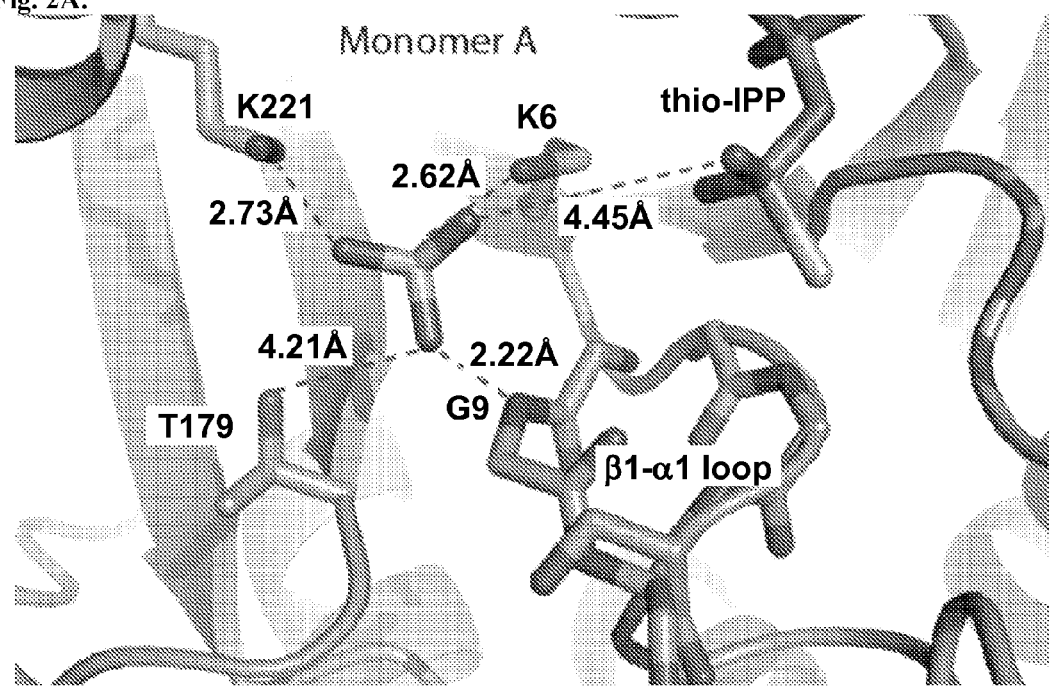
FIGS. 2A-2B: Shown in FIGS. 2A-2B is the sulfate ion in the active site of both monomers A (FIG. 2A) and B (FIG. 2B) of IPK complexed with thio-IPP (IPPβS). The position of this sulfate ion is conserved among all structures of IPK that are presented here, and is thought to represent the location of the β-phosphate from ATP. This sulfate ion is therefore referred to as the "β-sulfate ion." The O atoms of the β-sulfate ion are in close proximity to a number of different residues. These interacting residues vary between monomer A (FIG. 2A) and monomer B (FIG. 2B) and reflect subtle differences in the general active site architecture. There are large differences between monomers A and B in terms of the distance between the sulfate ion and a non-bridging O atom from IPPβS. This distance is much shorter in monomer B, although the trade-off appears to be weaker interactions between the β-sulfate ion and surrounding residues.
Figure 2B:
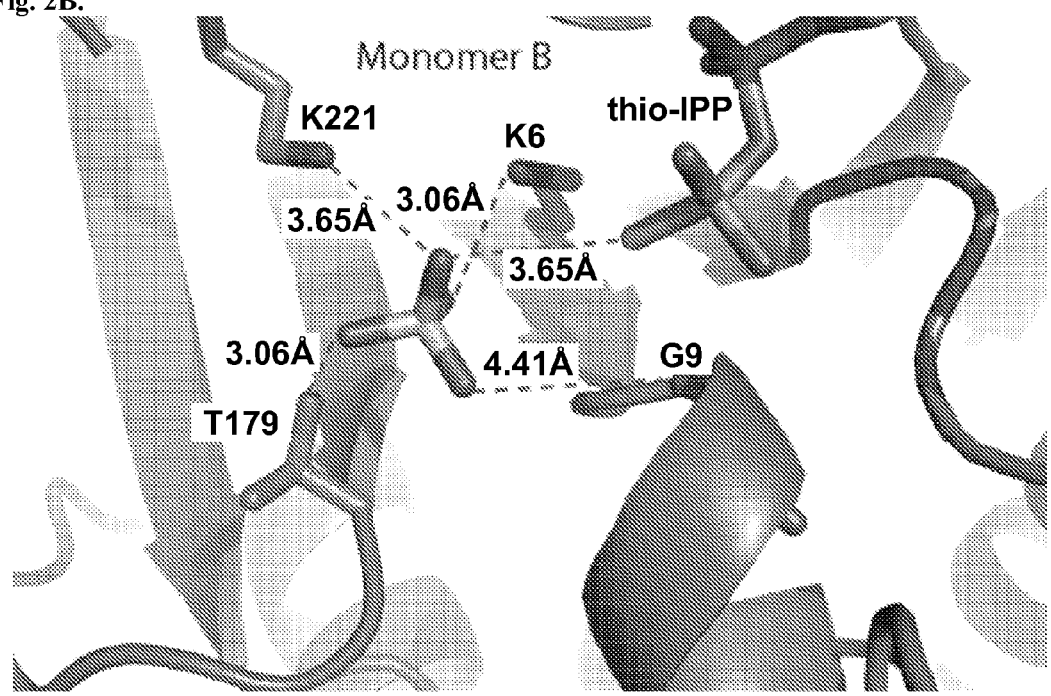
Figure 2C:
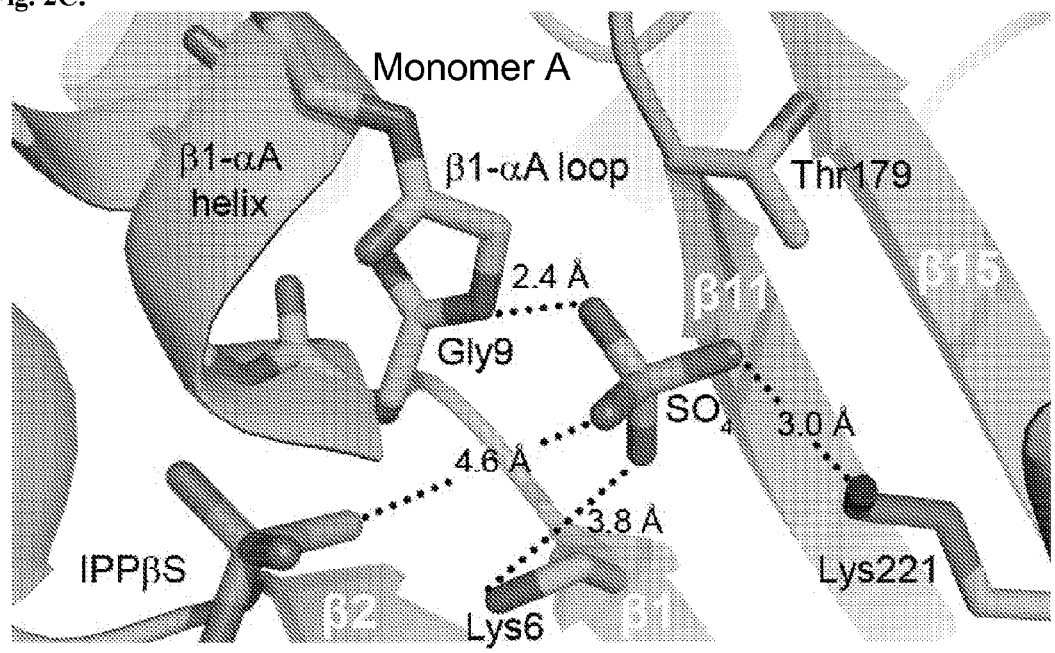
FIGS. 2C-2D depict further comparative close-up views of the nucleotide phosphate-binding region of IPK.
Figure 2D:
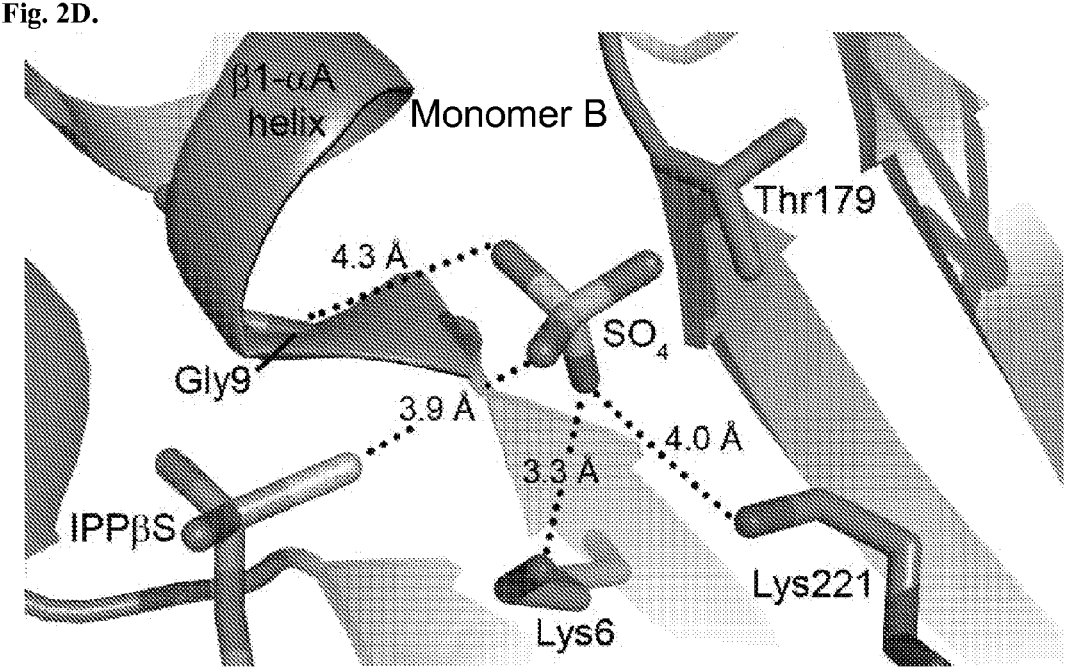

Like all other family members, IPK contains both an N-terminal and C-terminal domain. The N-terminal domain binds the phosphate acceptor (isopentenyl monophosphate in IPK), and extends from residue 1-171. The C-teiminal domain includes residues 171-260 and binds the phosphate donor (ATP) and magnesium. Although a structure of IPK with an ATP analog bound has not been solved, the location of the nucleotide binding site is conserved among all family members, and therefore it can be expected that ATP will bind similarly in IPK. Each monomer of IPK contains sixteen β-strands, eight α-helices, and one $3_{10}$-helix. The open αβα sandwich architecture is represented by 8 β-strands (β14, β16, β15, β11, β1, β2, β8, β5) which are sandwiched between four α-helices on one side (αF, αG, αE, αD) and three on the other (αH, αA, αC). As known in the art, helices αA, αB, αC, αD, αE, αF, αG and αH described herein can be referenced as α1, α2, α3, α4, α5, α6, α7 and α8, respectively. See FIG. 1C. In addition to the sandwich, there are four other β-hairpins and one additional α-helix. Three of the hairpins (β3-β4, β6-β7, and β9-β10) are part of the N-terminal domain and surround the back and one side of the isopentenyl monophosphate (IP) binding pocket; the remaining α-helix (αB) covers the other side. The last β-hairpin (β12-β13) is located within the C-terminal domain in close proximity to the expected location for the adenine ring of ATP. Additionally, there is one $3_{10}$-helix between one end of the central sheet (β5) and the β6-β7 hairpin. See FIG. 1C.

IPK crystallizes as a dimer in space group $P2_12_12$. The dimer consists of two monomers oriented around a non-crystallographic two-fold axis. This non-crystallographic dyadic axis is perpendicular to the central β-sheet (16 strands with 8 per monomer) that spans the length of the dimer. Although each family member has adopted a unique dimer interface (Marco-Marin et al., 2007, *J. Mol. Biol.* 367:1431-1446), the IPK interface is most similar to that of FomA kinase (Pakhomova et al., 2008, *J. Biol. Chem.* 283:28518-28526). In IPK, this interface is comprised of 10 electrostatic interactions, 12 hydrogen bonds, and 14 residues participating in hydrophobic interactions. Most of the hydrogen bond and electrostatic interactions are between the following motifs: 1) the αC helices of each monomer; 2) the αD helix of one monomer and the β9-β10 hairpin of the other monomer; 3) the $3_{10}$-helix of one monomer and the β5 sheet of the other. Hydrophobic interactions between the two molecules include residues from the αC and αD helices, the β4, β5,β6, β8, β9, β10 sheets, and the $3_{10}$-helix.

The main difference between the two monomers is that monomer B does not show any electron density for the αF-αG loop (residues 207-218). In monomer A, the loop is ordered, although it is in an orientation that would clash with the putative location of ATP. The ordering or re-ordering of this loop to accommodate ATP occurs in some family members, such as FomA kinase from *S. wedmorensis* (Pakhomova et al., 2008, Id.), UMPK from *P. furiosus* (Marco-Marin et al., 2005, *J. Mol. Biol.* 352:438-454), and one of the six subunits of UMPK from *S. solfataricus* (Jensen et al., 2007, *Biochemistry.* 46:2745-2757). In other family members, the loop either remains disordered upon nucleotide binding (Jensen et al., 2007, Id.), or was never disordered to begin with. For example, all bacterial UMPKs have a very short, ordered loop at this position in comparison to archaeal UMPKs (Jensen et al., 2007, Id.).

Here, we report four crystal structures of IPK: apo, IP-bound, IPP-bound, and IPPβS-bound. Multiple conformations of certain loops and ligands can be observed in the active sites of these structures. Based on structural observations, His60 is thought to play an essential role in binding, and its catalytic importance was assessed through mutation and kinetic analysis. All structural and kinetic observations combined with reports of similar (or dissimilar) trends within the rest of the AAK family have directed us towards predictions on how this enzyme performs its reaction.

Two Sulfate Molecules in the Active Site

The apo structure contains two sulfate molecules in the active site. One of them superimposes to the position of the monophosphate in the IP-bound structure, and is therefore only present in the apo structure. The other sulfate is present in all structures and resembles the approximate location of the β-phosphate of ATP. This approximation is based on a superposition of IPK onto ATP-analog bound structures from other family members (Marco-Marin et al., 2005, Id.), (Ramon-Maiques et al., 2002, *Structure* 10:329-342), (Pakhomova et al., 2008, Id.) Among the structures of IPK, this sulfate ion is usually hydrogen-bonded to several of the four following residues: Gly9, Lys6, Lys221, and Thr179. See FIG. 2. These residues correlate with those stabilizing the β-phosphate of ADP or ATP-analogues in other structures of the AAK superfamily (PDBIDs: 2hmf (Faehnle et al., 2006, *Acta Crystallogr. Sect. F. Struct. Biol. Cryst. Commun.* 62:962-966), 1ohb (Gil-Ortiz et al., 2003, *J. Mol. Biol.* 331:231-244), 2j0w (Kotaka et al., 2006, *J. Biol. Chem.* 281:31544-31552), 2bri (Marco-Marin et al., 2005, Id.), 3c1m (Liu et al., 2008, *J. Biol. Chem.* 283:16216-16225), 3d41 (Pakhomova et al., 2008, Id.), 1gs5 (Ramon-Maiques et al., 2002, Id.)). Therefore, this sulfate ion mimics the β-phosphate of ATP in terms of both position and nature of stabilization, and will herein be referred to as the β-sulfate ion.

The IP-Binding Pocket

Figure 3A:
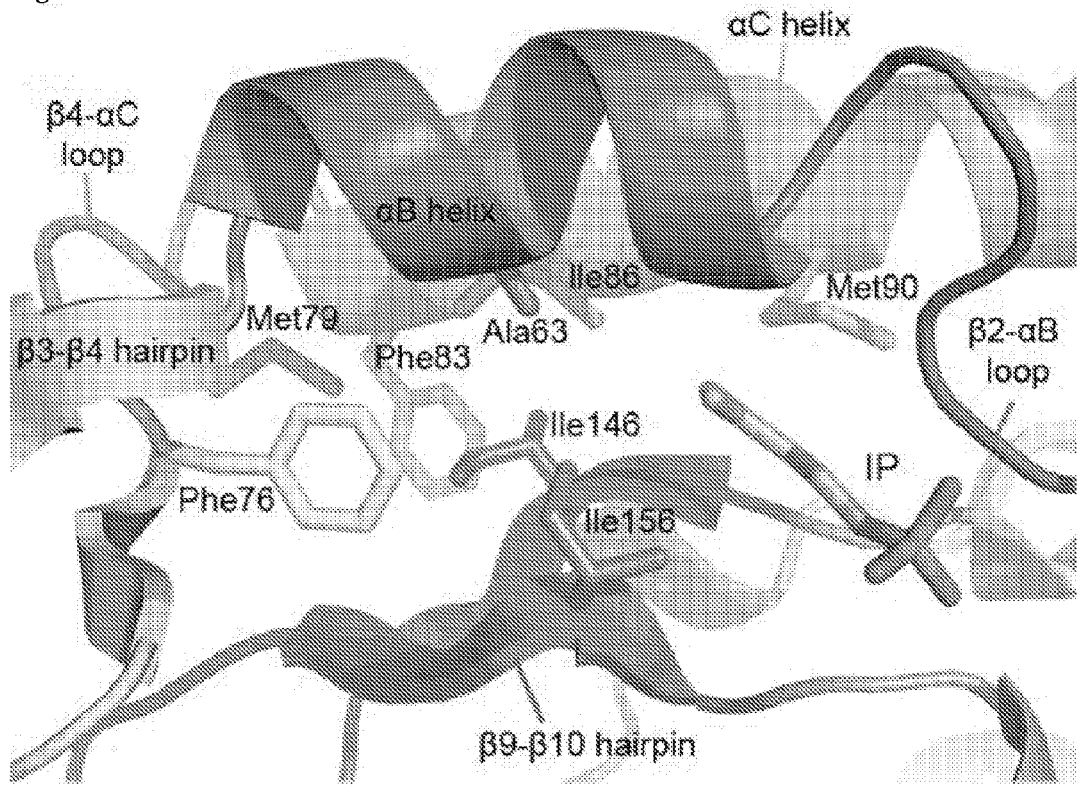
FIG. 3A.
Figure 3B:
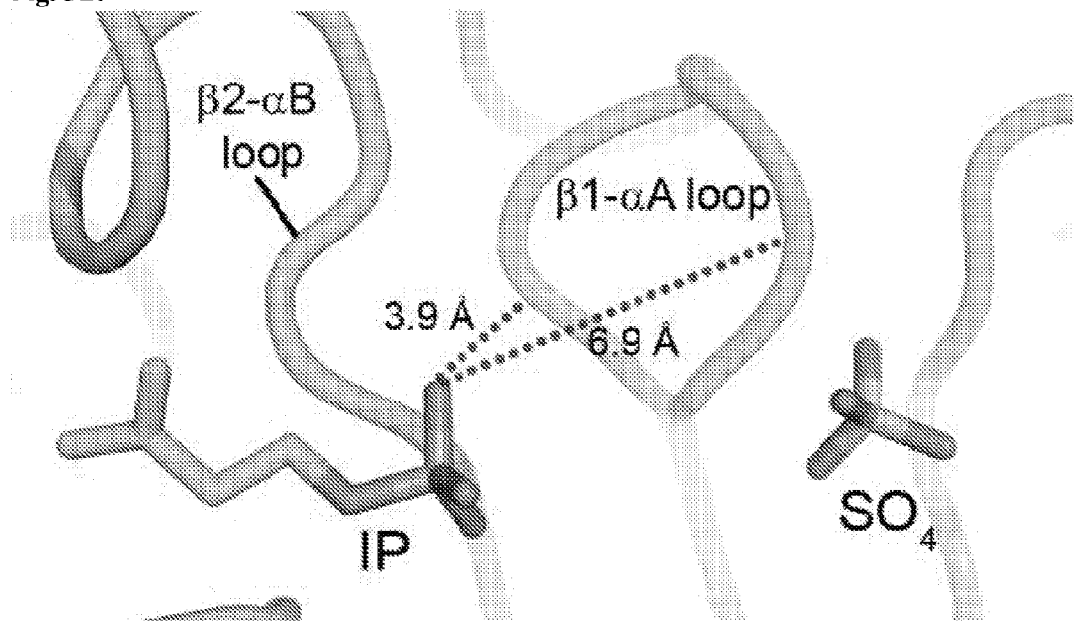
FIG. 3B.
Figure 4A:
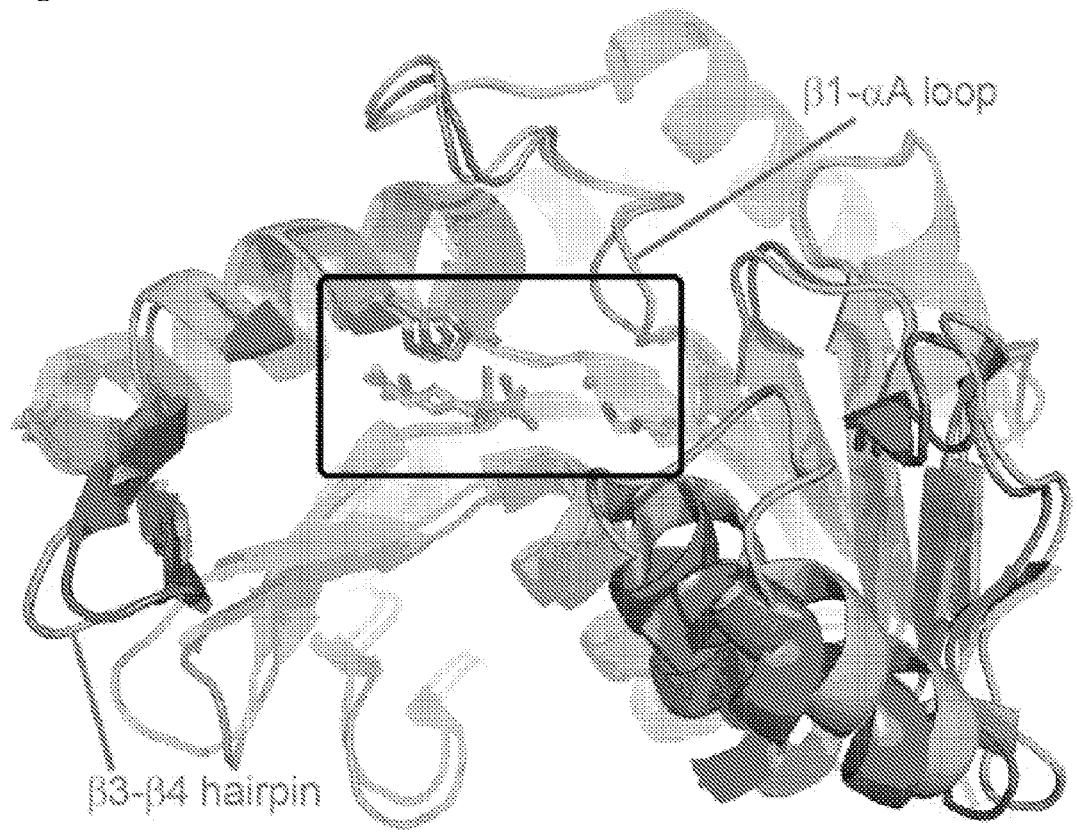
FIG. 4A.
Figure 4B:
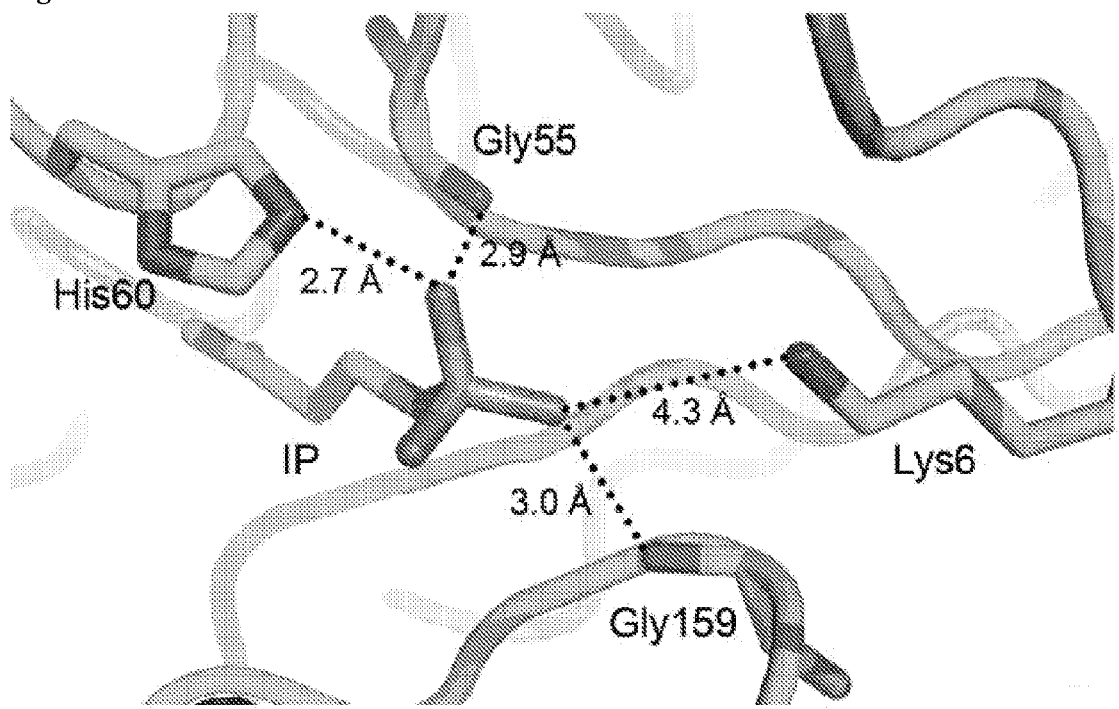
FIGS. 4B-4C.
Figure 4C:
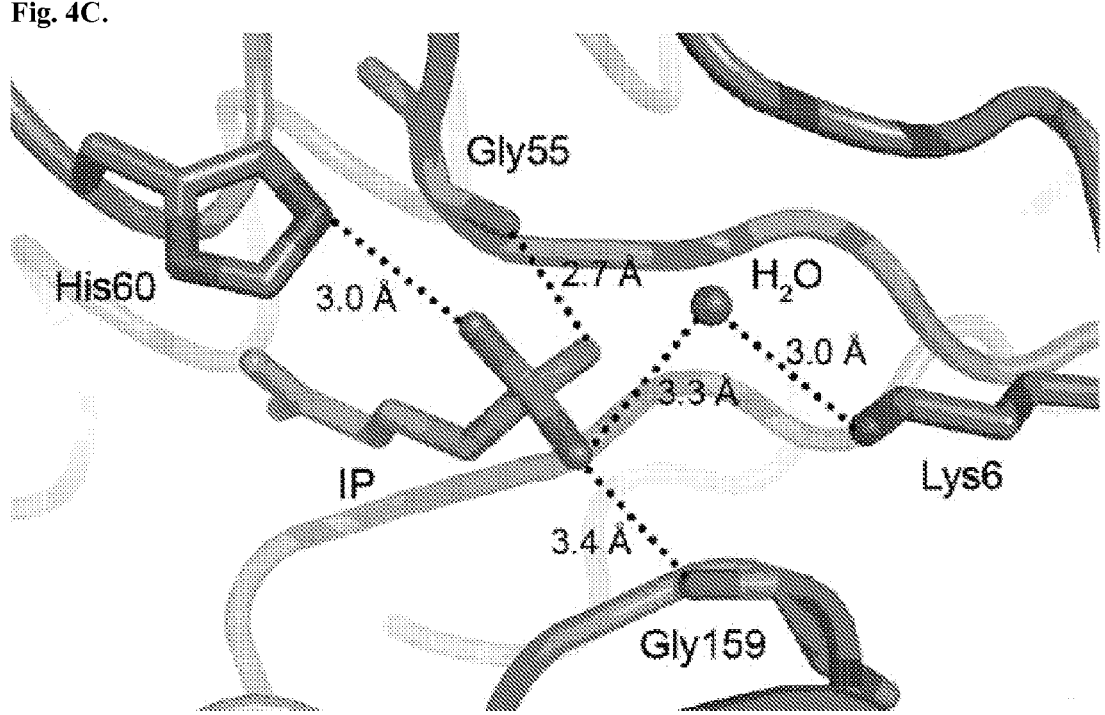
Figure 4D:
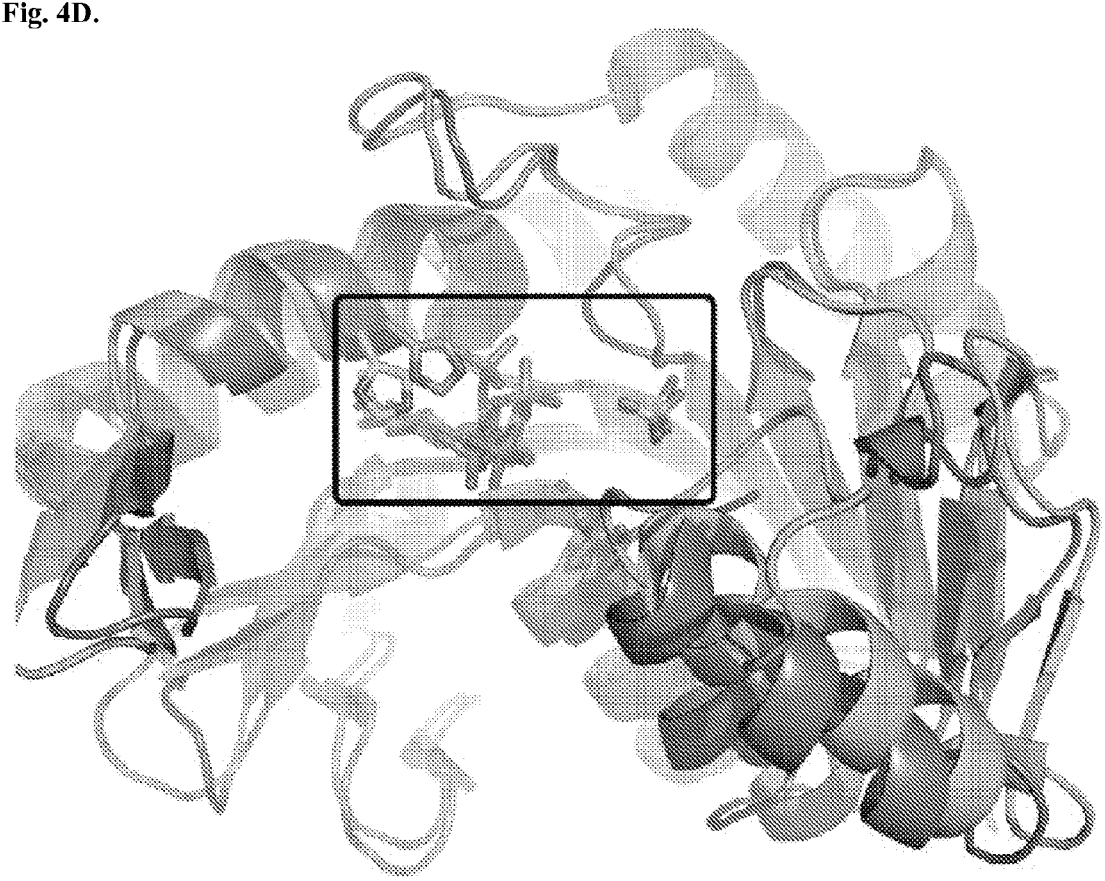
FIG. 4D.
Figure 4E:
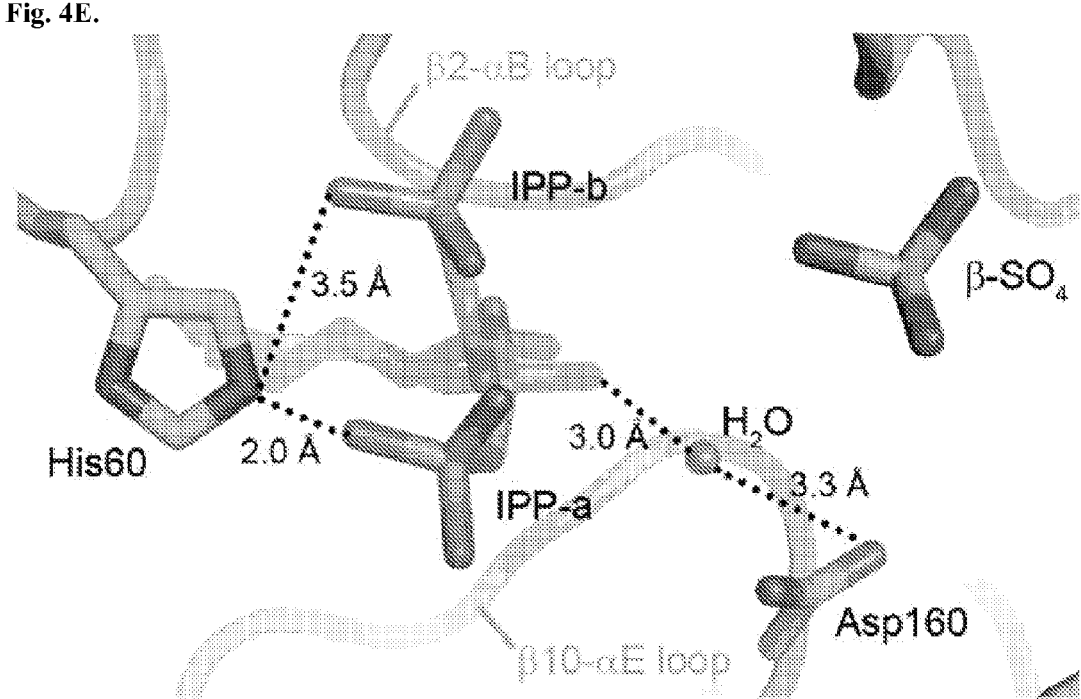
FIGS. 4E-4F.
Figure 4F:
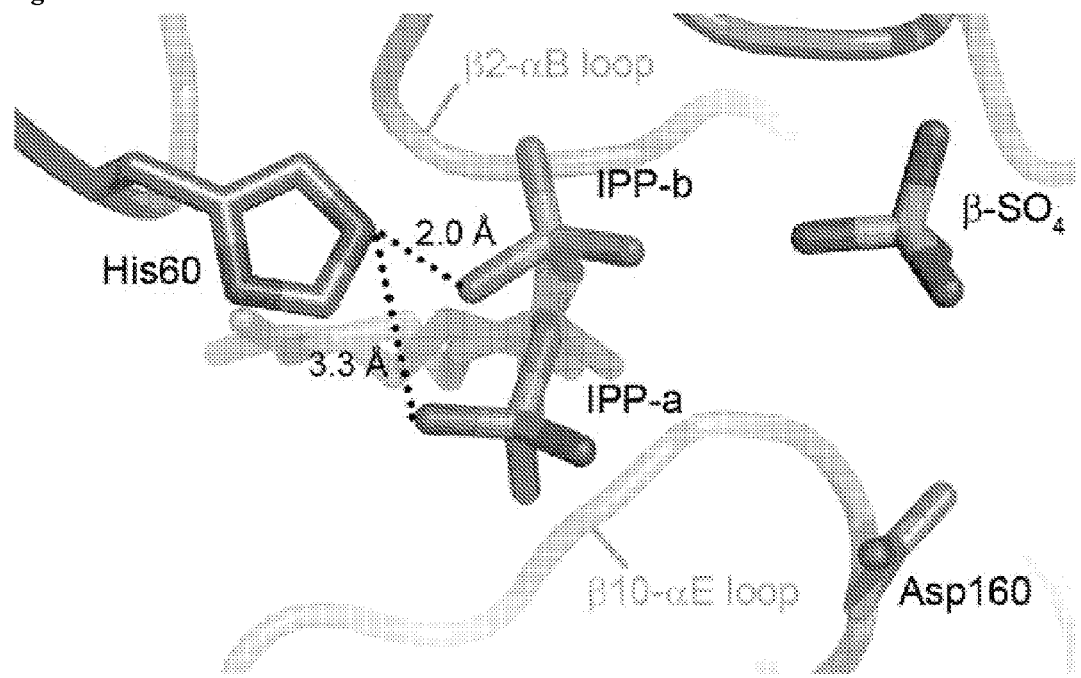

The crystal structure of substrate-bound IPK was the first visual assertion of the enzyme's ability to bind its substrate, isopentenyl monophosphate (IP). The secondary structural elements comprising the IP-binding pocket include the β2-αB glycine-rich loop, αB helix, β3-β4 hairpin, β4-αC loop, N-terminal part of the αC helix, and the β9-β10 hairpin. See FIG. 3. The β2-αB loop is one of the two conserved glycine-rich loops present throughout the AAK family, and is thought to be responsible for charge neutralization and product stabilization during and after phosphoryl transfer (Gil-Ortiz et al., 2003, Id.; Pakhomova et al., 2008, Id.) The αB helix is only conserved in members of the family that bind substrates with phosphate or phosphonate functional groups (e.g., IPK, UMPK, FomA). In FomA, the αB helix is only ordered when substrate is present, and is otherwise a disordered loop (Pakhomova et al., 2008, Id.) This is not the case in IPK, as this helix is relatively ordered in both apo and IP-bound structures. The β3-β4 hairpin is a motif that is present only in IPK and NAGK. In NAG-bound NAGK structures, the hairpin is often found in a closed position (Ramon-Maiques et al., 2002, Id.; Ramon-Maiques et al., 2006, *J. Mol. Biol.* 356:695-713); in contrast, all structures of IPK show the motif in an open position. Nevertheless, the hairpin may have some involvement in shielding the substrate binding pocket from solvent in both proteins.

The substrate (IP) contains two moieties: a non-polar tail and a polar phosphate head group. The non-polar, 5-carbon tail of the substrate is surrounded by a deep pocket of hydrophobic residues, including Ala63, Ile86, Ile146, Ile156, Phe76, Phe83, Met79, and Met90. See FIG. 3. The phosphate moiety of the substrate is positioned between three motifs: His60, the β2-αB loop (residues 54-56), and the β10-αE loop (residues 157-159). In both monomers, the $N\epsilon_2$ atom of His60 hydrogen bonds to a non-bridging O atom on the phosphate on IP. In monomer B, Gly55 of the β2-αB loop hydrogen bonds to a non-bridging O atom of IP, while a similar interaction occurs in monomer A between Gly159 of the β10-αE loop and IP. A superposition of the two monomers demonstrates that differences in the hydrogen bonding residues arise from slight changes in the conformations of both His60 and the IP molecule within each monomer, and not from reorientation of these two loops.

In monomer A, there is another loop at the β1-αA junction (gly8-leu12) that is near the active site and can adopt two distinct binding modes. In one binding mode, the loop sits near the active site β-sulfate ion, while the other binding mode places the loop in closer proximity to the β2-αB loop. None of the residues in this loop participate in hydrogen bonding interactions with the substrate; however, the dual binding mode is not observed for the apo structure, suggesting that loop movement is partially dependent on the presence of substrate. In monomer B, the loop does not have two binding modes, but instead adopts a conformation that is roughly between the two modes present in monomer A.

Multiple Conformations of IPP in One Active Site

Figure 5:
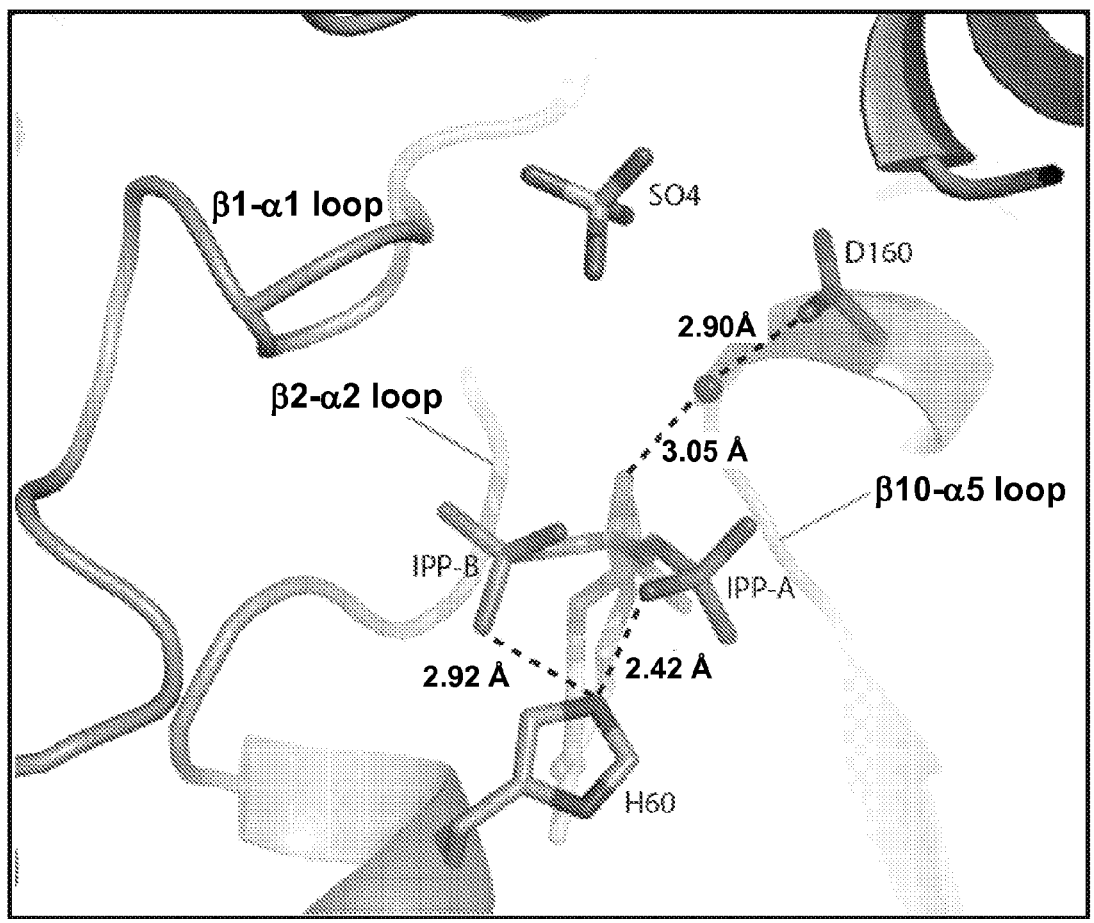
FIG. 5: Multiple conformations of IPP in the active site. When IPP is soaked into IPK crystals and the protein X-ray crystal structure solved and refined, the product is seen to adopt two distinct conformations. Shown in FIG. 5 are the two conformers of IPP (IPP-A and IPP-B), surrounding loops, and the β-sulfate ion present in the active site of Monomer A. Both monomers show two IPP conformers that are in the same position, although monomer B only shows one conformation for the β1-αA loop and does not contain the water molecule that is hydrogen bonded between D160 and a non-bridging O atom of the IPP α-phosphate in monomer A.
Figure 6:
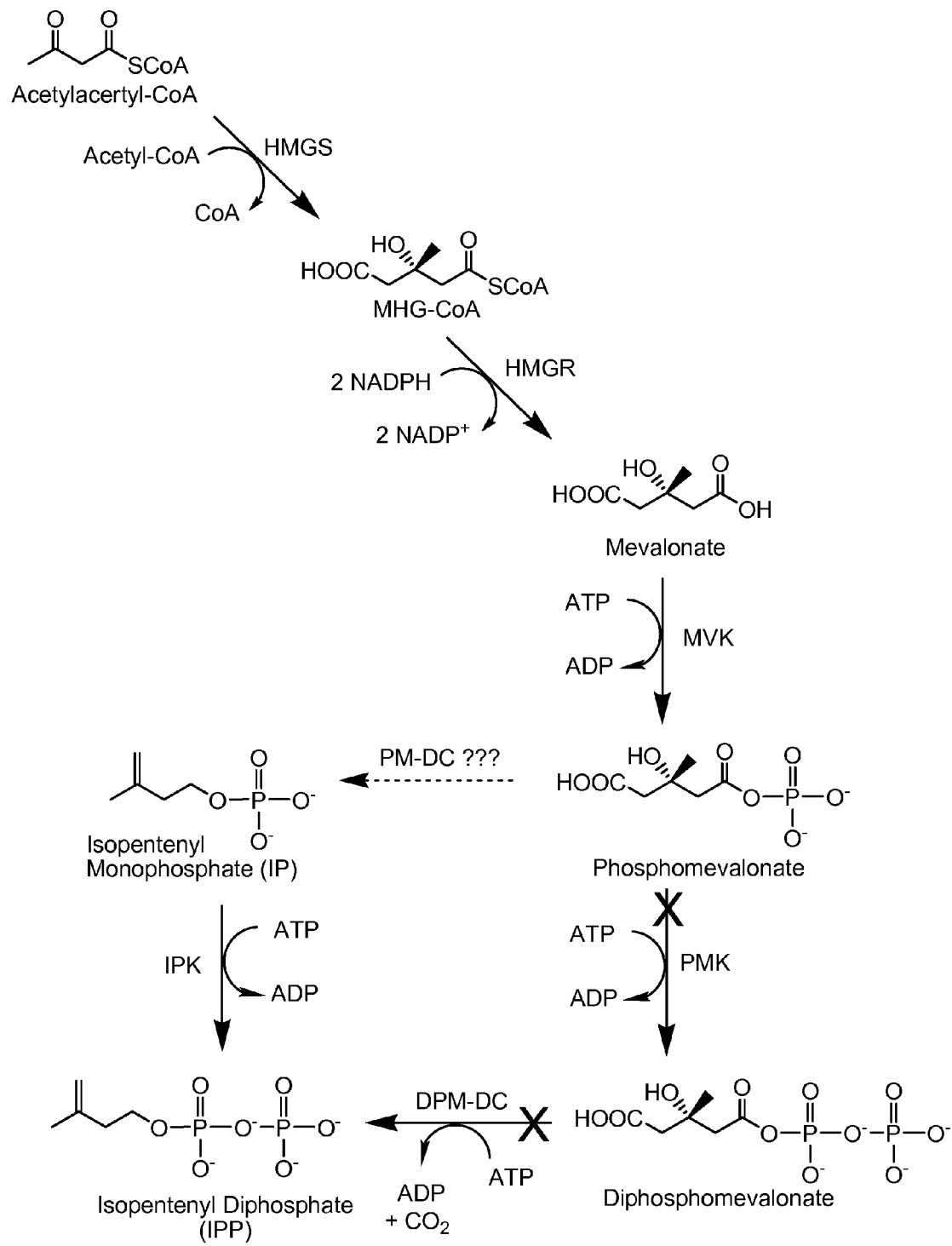
FIG. 6: The Lost Pathway In Archaea. Shown are molecules that are part of the mevalonate pathway. In archaea, the two last genes of this pathway leading up to IPP biosynthesis are missing (designated by X's). For this reason, the isoprenoid pathway in archaea has been referred to as "The Lost Pathway". See Smit & Mushegian, 2000, Id. In 2006, a group discovered an enzyme present in the archaeon *Methanocaldococcus jannaschii* that was able to phosphorylate isopentenyl monophosphate, thereby producing IPP. See Grochowski et al., 2006, Id. This protein is called isopentenyl monophosphate kinase (IPK).
Figure 7:
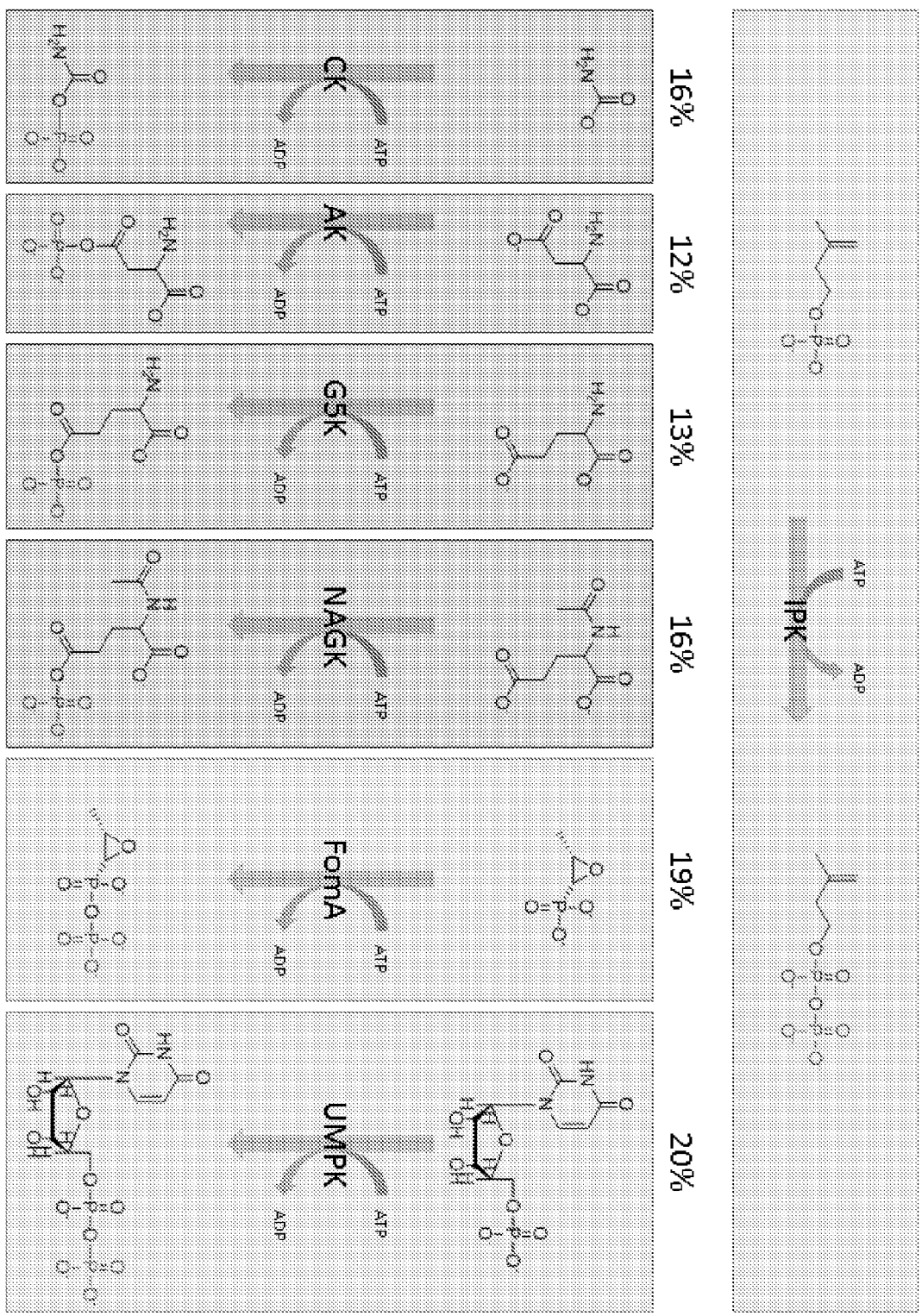
FIG. 7: PF000696: Amino Acid Kinase (AAK) superfamily. Isopentenyl phosphate kinase (IPK) reaction is depicted across the top of FIG. 7. Representative family members displayed from left to right: carbamate kinase (CK), aspartokinase (AK), glutamate-5-kinase (G5K), N-acetyl-1-glutamate kinase (NAGK), fosfomycin resistance kinase (FomA), and uridine monophosphate kinase (UMPK). The percent sequence identities relative to IPK are listed above each enzyme. Reactions with FomA and UMPK utilize a phosphate or phosphonate phosphoryl acceptor, while the reactions of CK, AK, G5K and NAGK utilize carbamate or carboxylate groups as phosphate acceptors.

The crystal structure of IPK with its product bound reveals that IPP adopts two distinct conformers: conformer A and conformer B. These conformers are similar except in the orientation of the terminal β-phosphate group and the bridging O atom between the two phosphate groups. In conformer A, these two moieties are closer to the β10-αE loop, while in conformer B, they are closer to the β2-αB loop and one binding mode of the αA-β1 loop. See FIG. 5. In conformer A, the β-phosphate group is secured by only one hydrogen bond interaction between a non-bridging O atom from the β-phosphate and the N$\epsilon_2$ atom of His60. In conformer B, the β-phosphate is perpendicular to this orientation, and its conformation allows for two hydrogen bonding interactions with non-bridging O atoms: one with the N$\epsilon_2$ atom of His60 and another with the N atom of Gly55 from the β2-αB loop. The rest of the IPP molecule is oriented similarly in both conformers; the hydrophobic tails are in the same general location and the a-phosphate group is positioned between the β2-αB loop and the β10-αE loop, stabilized by the N atoms of Gly55 and Gly159, respectively.

In monomer A only, a water molecule is secured between a non-bridging O atom from the α-phosphate of IPP and Asp160 through hydrogen bonding interactions. See FIG. 5. This water molecule is also found in substrate-bound structures of FomA kinase (PDBID 3d41) (Pakhomova et al., 2008, Id.), E. coli NAGK (PDBID 1gs5) (Ramon-Maiques et al., 2002, Id.), P. furiosus UMPK (PDBID 2bmu) (Marco-Marin et al., 2005, Id.), and E. coli UMPK (PDBID 2bne) (Briozzo et al., 2005, J. Biol. Chem. 280:25533-25540), and it is stabilized in a similar fashion for each of these structures. Asp160 of IPK is highly conserved among the family, and has been suggested to function as an active site base and a key organizing residue (Pakhomova et al., 2008, Id.; Marco-Marin et al., 2003, J. Mol. Biol. 334, 459-476). As mentioned previously, the β1-αA loop again occupies two distinct binding modes in monomer A: one of the binding modes places it within 4 Å of the β-phosphate of conformer B, and the other binding mode interacts with the β-sulfate ion. The β1-αA loop is often reported to interact with the β- and γ-phosphate groups from ATP analogs, however there are also examples of this loop interacting with the β-phosphate of the product (in UMPK from E. coli) (Gil-Ortiz et al., 2003, Id.; Briozzo et al., 2005, Id.)

The catalytically relevant conformer for IPP is most likely conformer B. This can be supported by three pieces of information: 1) one of the binding modes for the β1-αA loop, which is thought to play a key role during phosphoryl transfer, is in close proximity to the β-phosphate of conformer B (Gil-Ortiz et al., 2003, Id.); 2) a superposition of UDP-bound UMPK from E coli and IPP-bound IPK shows that the phosphate moiety of UDP superimposes with conformer B of IPP (Briozzo et al., 2005, Id.); 3) the ATPgS/IP/Mg structure (discussed below) has a thio analog of IPP, IPPβS, bound in a single conformation that superimposes with conformer B of IPP from the IPP-bound structure. Conformer A of IPP may therefore represent a post-reaction EP complex.

A Post-Reaction Active Site Containing IPPγS

When a crystal of IPK is soaked with IP, magnesium, and ATPγS, IPPβS is observed in the active site. This product looks similar to IPP except one of the non-bridging O atoms on the β-phosphate is replaced with an S atom. There is no electron density for the ADP molecule. This is the only structure where both substrates were soaked into the preformed crystal leading to products through the catalytic action of IPK in the crystal lattice with an ATP analog, and it most closely represents a post-reaction snapshot of the active site. Interestingly, this structure reveals only one binding mode for IPPβS which is consistent with the orientation of conformer B in the IPP-bound structure. The interactions between the active site residues and ligands are also conserved between the IPP-bound and IPPβS-bound structures: the β-thiophosphate group of IPPβS remains in close proximity to His60 and the β2-αB loop while the α-phosphate is stabilized by Gly159 from the β10-αE loop.

Monomer A and B again differ with regard to the precise location of IPPβS within the active site. In monomer A, IPPβS and the sulfate ion are 4.45 Å apart, while in monomer B they are only 3.66 Å apart. The distance is shorter in monomer B because the IPPβS molecule has shifted towards the sulfate ion, and as a direct consequence, some of the hydrogen bonding interactions between the product and the surrounding residues are weaker or are lost. For example, in monomer B, the distance between His60 and a non-bridging O atom of the β-phosphate group is larger than in monomer A. Although the active sites in both monomers are product-bound and therefore represent late phases in the IPK reaction, the intermediate location of the β-phosphate group in monomer B coupled with the heightened dynamics of certain loops within this monomer may suggest that it represents a slightly earlier phase of the reaction compared to monomer A.

His60 has a Key Function in Binding and Catalysis

From the results discussed above, it is evident that His60 from IPK plays an important role in both substrate and product binding. This is accomplished through a hydrogen bonding interaction between the N$\epsilon_2$ atom of His60 and a non-bridging O atom from the terminal phosphate group on either the substrate (IP) or the product (IPP). From all crystal structure data, it is apparent that the N$\epsilon_2$ group of His60 (and not the N$\delta_1$ group) is relevant for binding and may therefore be reasonably assumed by one skilled in the art to be relevant for IPK-mediated catalysis. To confirm this hypothesis, His60 was mutated to Ala, Asn, and Gln. The Asn and Gln mutations were made based on the rationale that their side chains contain N atoms that are isosteric with the N$\delta_1$ and N$\epsilon_2$ groups on His, respectively. The three mutants were assayed at 25° C. using the pyruvate kinase/lactate dehydrogenase coupled reaction to detect kinase activity, and it was found that the rates of H60A and H60N were immeasurable at relevant concentrations of IP and enzyme. The H60Q mutant (whose N atom in the side chain mimics the N$\epsilon_2$ nitrogen of histidine) was able to turn over a measurable amount of IP, and a kinetic analysis of this mutant was performed. The $K_m$ for IP was 8-fold larger than wild type at 34.5 µM, while the $k_{cat}$ was nearly 40-fold slower at 0.04 s$^{-1}$, yielding a $k_{cat}/K_m$ value 300 times higher for wild type (Table 4).

TABLE 4

Kinetic Data for IPK-Mm, IPK-Mj, and IPK-Mj mutants at 25° C.

| Protein Name | $K_{m, ATP}$ | $K_{m, IP}$ (µM) | $k_{cat}$ (s$^{-1}$) | $k_{cat}/K_{m, IP}$ (s$^{-1}$µM$^{-1}$) |
|---|---|---|---|---|
| IPK-Mjannaschii (IPK-Mj) | 198.2 ± 32.7 | 4.30 ± 0.58 | 1.46 ± 0.03 | 0.34 |

TABLE 4-continued

Kinetic Data for IPK-Mm, IPK-Mj, and IPK-Mj mutants at 25° C.

| Protein Name | $K_{m, ATP}$ | $K_{m, IP}$ (µM) | $k_{cat}$ (s$^{-1}$) | $k_{cat}/K_{m,IP}$ (s$^{-1}$µM$^{-1}$) |
|---|---|---|---|---|
| IPK-Mmaripaludis (IPK-Mm) | | 21.4 ± 4.2 | 13.1 ± 0.5 | 0.61 |
| IPK-Mjannaschii H60A | — | — | — | — |
| IPK-Mjannaschii H60N | — | — | — | — |
| IPK-Mjannaschii H60Q | 559.3 ± 116.9 | 34.5 ± 7.2 | 0.040 ± 0.002 | 0.001 |

These results suggest several conclusions: 1) since the H60A and H60N mutants have no measurable activity, binding and/or catalysis is dependent on the presence of a proton bearing nitrogen atom that is isosteric with the Nε$_2$ nitrogen of His60; 2) given that the H60Q mutant has a significantly higher $K_m$ than wild type, His60 is important for substrate binding; additional flexibility in the Gln side chain may hinder the H60Q mutant IPK ability to bind substrate as effectively as wild type; and 3) the fact that the $k_{cat}/K_m$ value is almost 300 times higher in wild type compared to the H60Q mutant IPK suggests that His60 plays a role in transition state stabilization. Although glutamine is a good substitution for a hydrogen bonding residue, it is a weaker hydrogen bond donor due to its neutrality while a protonated His60 may carry an additional positive charge. Therefore, a glutamine residue may be less efficient than histidine at stabilizing the negatively charged intermediate.

Upon comparing the IPK structures, it is evident that His60 shifts from stabilizing the α-phosphate on IP to stabilizing the β-phosphate on IPP. A similar observation was reported in *E. coli* UMPK, where Arg62 (aligns with H60 of IPK) hydrogen bonds to the α-phosphate of UMP in the substrate-bound structure and the n-phosphate of UDP in the product-bound structure (Briozzo et al., 2005, Id.) Arg62 is thought to be involved in charge neutralization and orientation of the γ-phosphoryl group from ATP for nucleophilic attack by the phosphate moiety of the substrate (Briozzo et al., 2005, Id.), and His60 may serve a parallel role in IPK. In FomA, His58 (the residue in alignment with His60 of IPK) is too far away to directly interact with the fosfomycin substrate, although it may indirectly stabilize the substrate through a water molecule that is within hydrogen bonding distance to both His58 and fosfomycin (Pakhomova et al., 2008, Id.) Another key difference between IPK and FomA is that His58 of FomA is located in a region of the protein that becomes ordered into an extended αB helix upon binding of substrate and AMPPNP, while this same helix in IPK is ordered in all structures presented here.

It is interesting to note that the only AAK family members that have a residue aligning with His60 of IPK are those that phosphorylate a phosphate or phosphonate functional group (IPK, UMPK, FomA). FomA from *S. wedmorensis* has a histidine at this position (His58), while a structural alignment of all UMPKs shows a conserved arginine at the same location. The other four family members that phosphorylate a carboxylate or carbamate functional group do not have a residue or a motif that aligns with this region of IPK. This residue is therefore a distinguishing feature for members of the AAK family that catalyze transphosphorylation of a phosphate or phosphonate functional group. As discussed above, it most likely serves an important role in binding and catalysis for IPK, UMPK, and FomA, although a different residue (Arg in UMPK) or a structural change (ordering of αB helix in FomA) implies that the precise function of this residue is somewhat unique for each of these catalytically distinct enzymes.

Difficulty Obtaining ATP-analog Bound Structure

Many different combinations of ATP, ADP or ATP-analogs with Mg$^{2+}$ and IP (or IPP) were soaked into crystals or co-crystallized with the protein in attempt to obtain a crystal structure of an ATP-analog in the active site of IPK. Thus far, we have not been successful in this regard, though there are several possible explanations. One explanation is that the high concentration of sulfate in the crystallization solution causes it to saturate the site where the β-phosphate of ATP would normally bind, thereby outcompeting the ATP-analog for its preferred binding site. However, when adenosine was soaked into the crystals, still no electron density was observed, suggesting that it is not only the triphosphate moiety of ATP that is responsible for lack of ATP or ATP-analog electron density in the solved protein x-ray crystal structures. A second explanation is that in IPK, ATP binds more weakly than IP. In IPK from *M. jannaschii*, the $K_{m,IP}$ at 25° C. is 4.3±0.6 µM while the $K_{m,ATP}$ is 198±33 µM. These values are similar to another IPK that was cloned and purified from the mesophilic archaeon *M. maripaludis* ($K_{m,IP}$=16.1 uM, $K_{m,ATP}$=96±6 uM at 25° C.). Weak $K_m$ values cannot however be the only factor affecting ATP binding in IPKs because these values are comparable to those observed for UMPK from *Sulfolobus solfataricus* ($K_m$ values for UMP and ATP of 14 µM and 81 µM, respectively) and they have reported a crystal structure that includes an ATP analog (Jensen et al., 2007, Id.). A high $K_m$ value for ATP could suggest that this protein lacks important ATP-binding residues. However, this does not appear to be the case, as IPK has been reported to prefer ATP over GTP (Grochowski, et al., 2006, Id.) and contains many of the residues that are thought to be important for ATP-binding in other family members. One of the only significant exceptions is that IPK lacks a tryptophan residue that is observed to participate in stacking interactions with the adenine base of ATP in the active site of FomA, although this residue is not conserved among the family(Pakhomova et al., 2008, Id.) Our inability to obtain a crystal structure with an ATP-analog is most likely a combination of these problems discussed above.

Conclusion

Isopentenyl monophosphate kinase from *Methanocaldococcus jannaschii* is the newest structural member to the amino acid kinase family. Although the family was originally comprised mostly of amino acid or amino acid derived kinases (with the exception of carbamate kinase), more recently discovered members utilize other kinds of substrates such as nucleotides (UMPK), or antibiotics (FomA kinase). IPK is a part of the latter category, as it uses a substrate that is putatively derived from the archaeal mevalonate pathway, and most certainly has significance in the downstream production of essential isoprenoid products. Interestingly, the members of the latter category (UMPK, FomA, IPK) utilize substrates that contain a phosphate or phosphonate functional group. This observation coincides with the fact that these three proteins exclusively align with one another along their αB helices and contain a residue at position 60 (in IPK) that indirectly or directly stabilizes the terminal phosphate group of the substrate or product. Therefore, a clear division exists between members of the family that utilize a phosphate or phosphonate functional group and members that utilize a carbamate or carboxylate functional group. This division involves a functional distinction pinpointed to His60 in IPK, which aligns with an Arg in UMPK and a His in FomA. The structural, mutational and kinetic experiments presented here have confirmed the importance of His60 as a catalytic residue. From these results, it is evident that His60 aids in the stabilization of the substrate and product and also participates in transition state stabilization.

Example 2

Rational Mutation of IPK

Active Site Models of IPK

Figure 9:
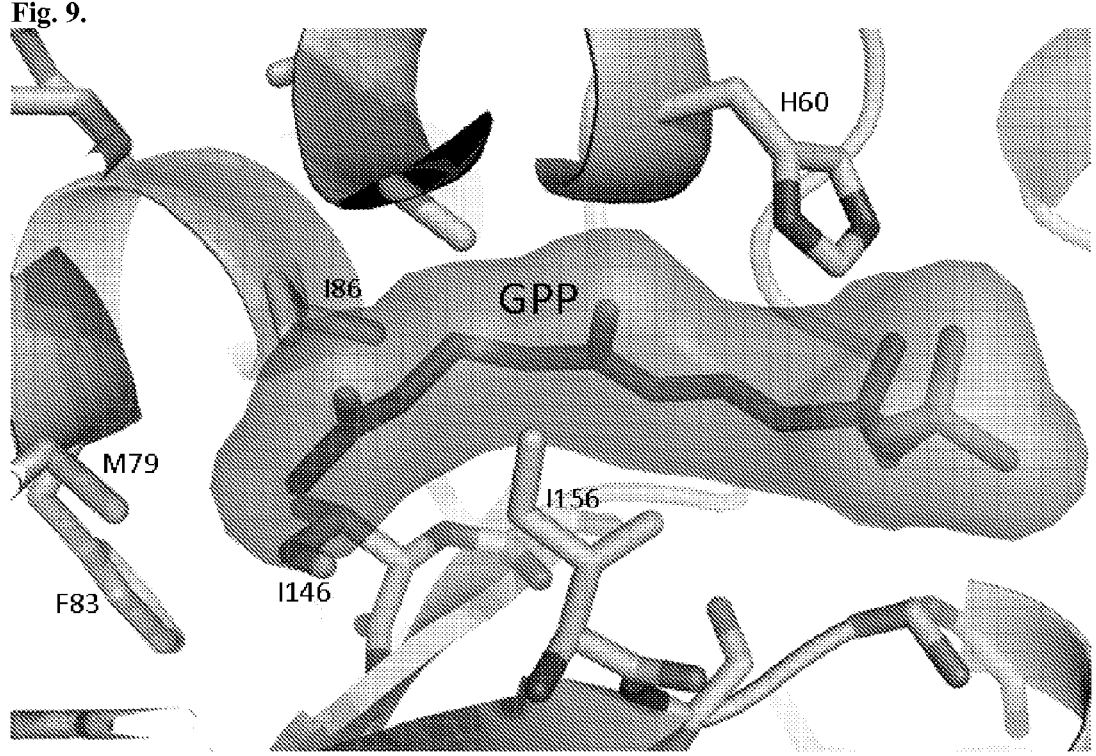
FIG. 9: Engineering IPK to accept longer chained isoprenyl monophosphates. Shown here is a snapshot of the IP binding pocket including residues that comprise the hydrophobic cavity. Geranyl diphosphate (GPP) was modeled into this cavity to determine how to rationally engineer IPK to accommodate longer chain isoprenoid monophosphate substrates. In this particular chain orientation, the side chains of Ile86 and Ile146 clash with the isoprenyl tail of GPP. Therefore, these two residues were mutated to alanine in an initial attempt to increase the cavity depth.

Based on the X-ray crystallographic studies described herein, molecular models of IPK, with and without substrate and/or product, were constructed by computational methods known in the art. For example, FIG. 9 depicts the IP binding pocket and hydrophobic cavity of IPK with GPP modeled into the cavity. The terms "cavity," "hydrophobic cavity" and the like in the context of IPK enzymatic activity refer to the volume wherein substrate may reside. In the particular chain orientation provided in FIG. 9, the side chains of Ile86 and Ile146 clash with the isoprenyl tail of GPP. The terms "clash," "steric hindrance" and the like refer in the customary sense to interatomic distances which would likely be prohibited due to energy considerations, for example, van der Waals repulsion between overlapping atoms. Therefore, the development of reasonable configurations and associated binding models of substrate within the IPK active site as determined by the methods described herein, and the determination of the associated energetic penalty associated with such binding modes, form at least one rational basis for the design of IPK mutations to achieve specific synthetic goals. In this case, residues Ile86 and Ile146 were mutated to alanine (I86A and I146A, respectively) in order to increase the cavity depth and thereby remove the energetic penalty to binding and/or reaction afforded by the native IPK structure. As is customary in the art, the term "XNNNZ" refers to mutation of the amino acid at position "NNN" from "X" to "Z" (standard one-letter amino acid code). For example, I86A refers to mutation of residue 86 from Ile to Ala. Similarly, "XXXNNNZZZ" refers to mutation of the amino acid at position "NNN" from "XXX" to "ZZZ" (standard three-letter amino acid code). For example, Ile86Ala refers to mutation of residue 86 from Ile to Ala.

Figure 10:
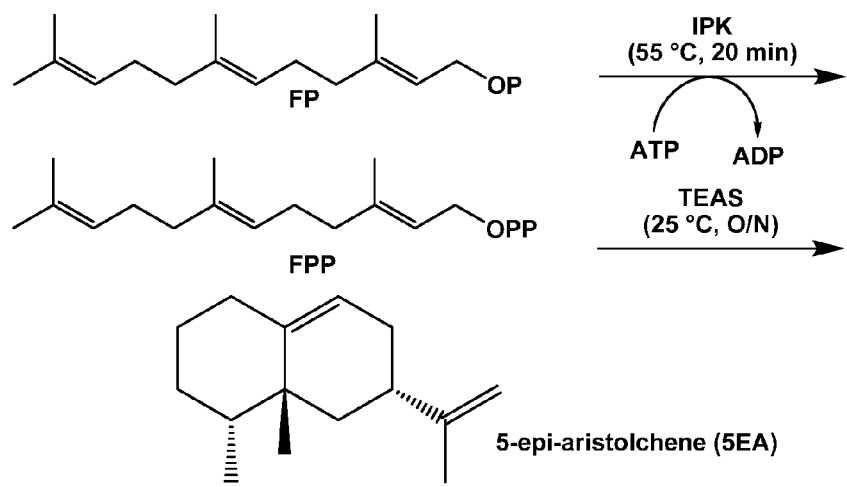
FIG. 10: Assays of IPK and mutants. The single mutants of IPK, I86A and I146A, and the double mutant I86A/I146A, were tested with the C15-substrate farnesyl monophosphate (FP) using a coupled assay with a terpene cyclase (TEAS). In the first step of the reaction, IPK was incubated with magnesium, ATP, and FP at pH 8.0 for 20 minutes at 55° C. (assuming sufficient time for conversion of FP to FPP). In the second step of the reaction, a small sample of the first reaction was added to a glass vial containing magnesium and a sesquiterpene cyclase known as tobacco 5-epi-aristolochene synthase (TEAS), and this reaction was incubated overnight at 25° C. Assuming complete conversion of FPP to 5-epi-aristolochene, the reaction was extracted with ethyl acetate and the amount of 5-epi-aristolochene was quantified by GC-MS analysis. Both single mutants and the double mutant were able to turn over a significant percentage of substrate within 20 minutes (shown in table in FIG. 10).

Similar studies were conducted using FPP modeled into the active site of IPK. The reaction of IPK on FP to form FPP is depicted in FIG. 10. The I146A I86A single-residue mutations, and the I146A/I146A double mutation were tested with the C15-substrate farnesyl monophosphate (FP) using a coupled assay with a terpene cyclase (TEAS). In the first step of the reaction, IPK was incubated with magnesium, ATP, and FP at pH 8.0 for 20 minutes at 55° C., which was judged as sufficient time for conversion of FP to FPP. In the second step of the reaction, a small sample of the first reaction was added to a glass vial containing magnesium and a sesquiterpene cyclase known as tobacco 5-epi-aristolochene synthase (TEAS), and this reaction was incubated overnight at 25° C. Assuming complete conversion of FPP to 5-epi-aristolochene, the reaction was extracted with ethyl acetate and the amount of 5-epi-aristolochene was quantitated by GC-MS analysis. As shown in the table in FIG. 10, both single mutants and the double mutant were able to phosphorylate a significant percentage of FP within 20 minutes. In contrast, the wild type IPK provided significantly less phosphorylation.

Figure 11A:
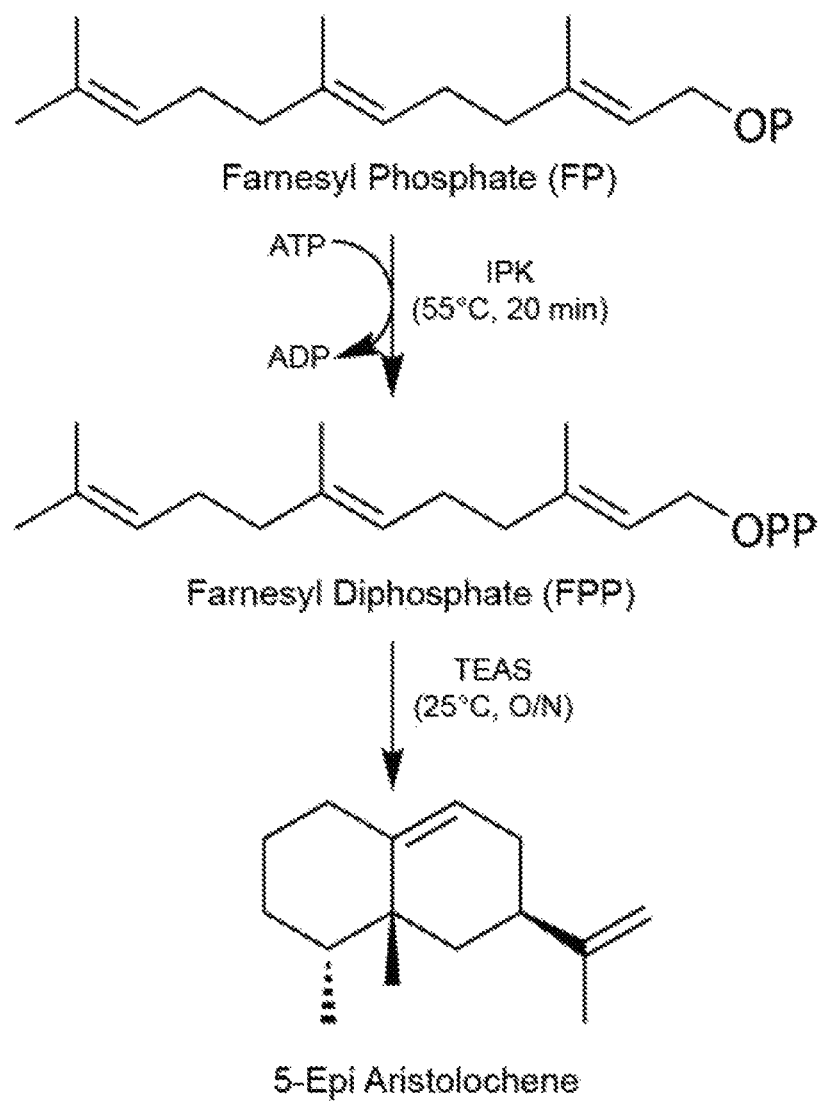
FIG. 11A.
Figure 11B:
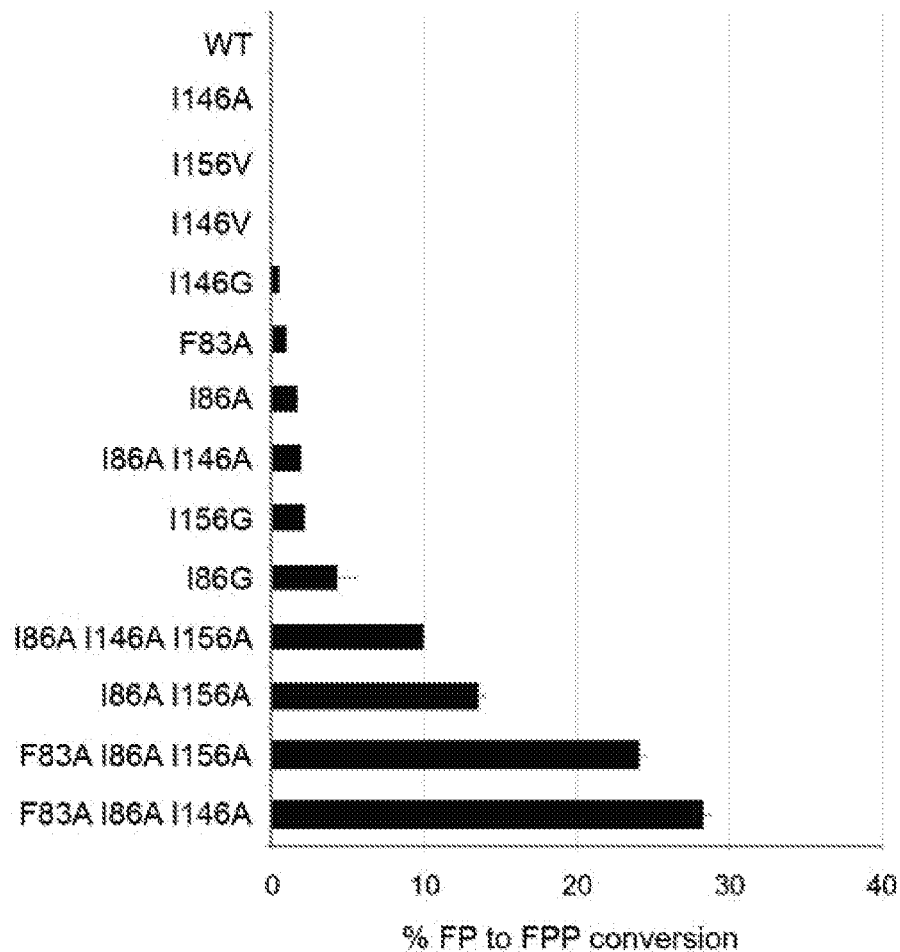
FIG. 11B.

In view of the initial model for FPP binding in the active site of IPK, four residues (I86, F83, I146 and I156) were identified as candidate targets for mutation. As shown in the graph of FIG. 11, significant conversion of FP to FPP is observed in a variety of single, double and even triple mutants of residues I86, F83, I146 and I156 of IPK. Indeed, the greatest turnover is observed for the F83A/I86A/I156A triple mutant. Interestingly, the I146V and I156V mutants have decreased activity. Without wishing to be bound by any theory, these observations suggest that potential repositioning of an amino acid can be detrimental towards accommodating a longer isoprenyl chain, and that mutations at the active site of IPK can increase the depth of the cavity allowing longer isoprenyl chains to bind and react more readily than in the wild type.

Figure 12:
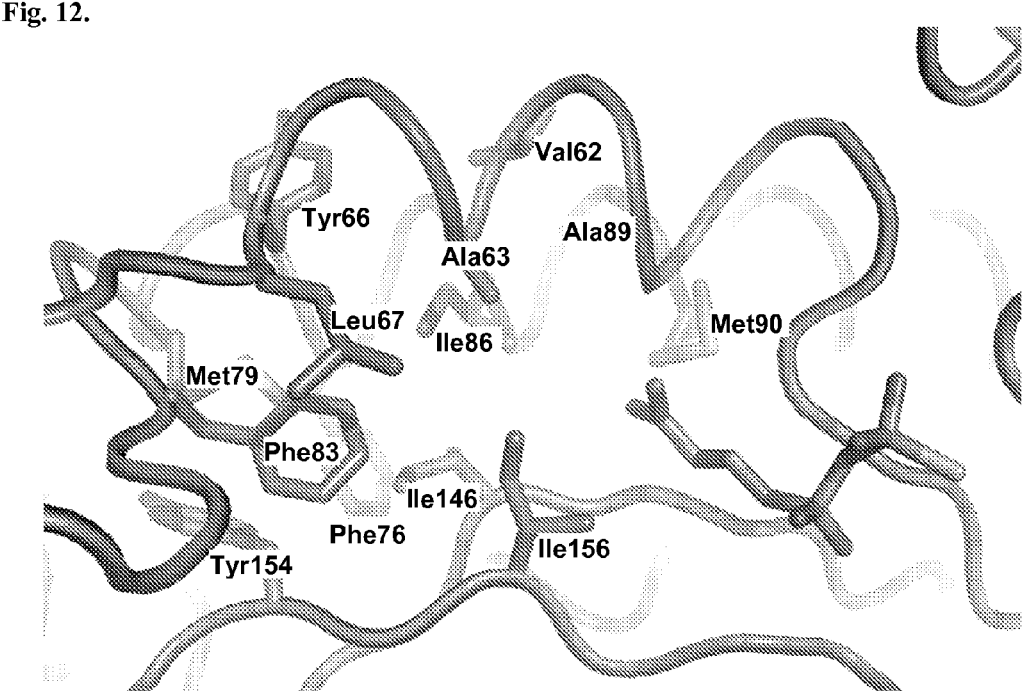
FIG. 12: Structural considerations for IPK active site mutations. A computationally generated graphic molecular model of a portion of the active site of IPK, built from the X-ray crystallographic structure described herein, is depicted in FIG. 12. Based on proximity, the following amino acids are identified as candidates to be mutated for modulation of the specificity and catalytic activity of IPK: Met90, Ala89, Val62, Ile86, Ile146, Ile156, Ala63, Phe83, Leu67, Tyr66, Tyr154, Phe76 and Met79.

An overall census of the active site of IPK, based on the X-ray crystallographic studies described herein, identifies at least 13 residues which are candidates to be mutated for the modulation of the substrate specificity and catalytic activity of IPK. As shown in FIG. 12, these residues are Met90, Ala89, Val62, Ile86, Ile146, Ile156, Ala63, Phe83, Leu67, Tyr66, Tyr154, Phe76 and Met79.

IPK Active Site Substrate Binding Modes

Figure 13:
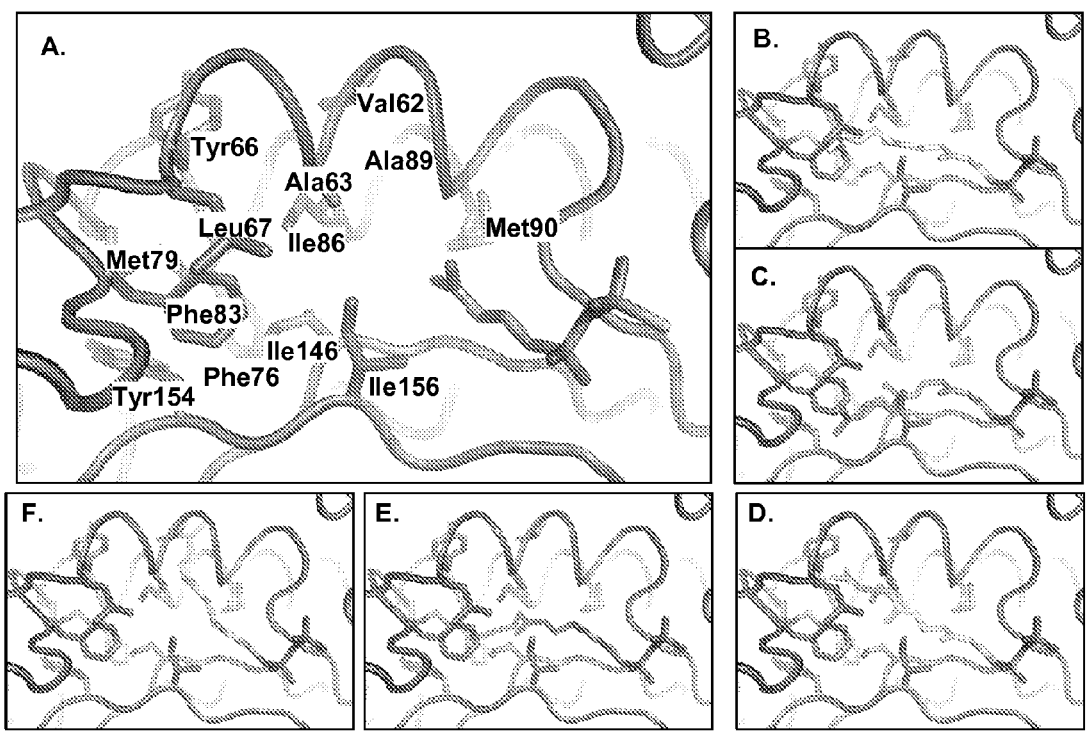
FIG. 13: FPP binding modes based on molecular modeling. Into the structural representations described in FIG. 12 was modeled FPP in five distinct conformations and associated binding modes. Panels: a) The perspective view of this panel is maintained in panels b-f and shows the active site of IPK with native enzyme substrate isopentenyl monophosphate (IP); b)-f) Five distinct orientations of FPP modeled within the IPK active site.

Further molecular modeling studies were conducted with substrate FPP modeled into the active site of the IPK X-ray crystallographic structure described herein. As shown in FIG. 13, wherein the point of view with respect to the IPK active site is maintained across all of the panels, FPP is in principle capable of binding in a variety of modes to IPK. In this case, five distinct configurations and binding modes of FPP were identified, each having at most a small number of potentially unfavorable steric interactions with the active site of IPK. Accordingly, each binding mode of FPP identifies a set of residues of IPK which could be mutated to achieve more energetically favorable binding.

Figure 14A:
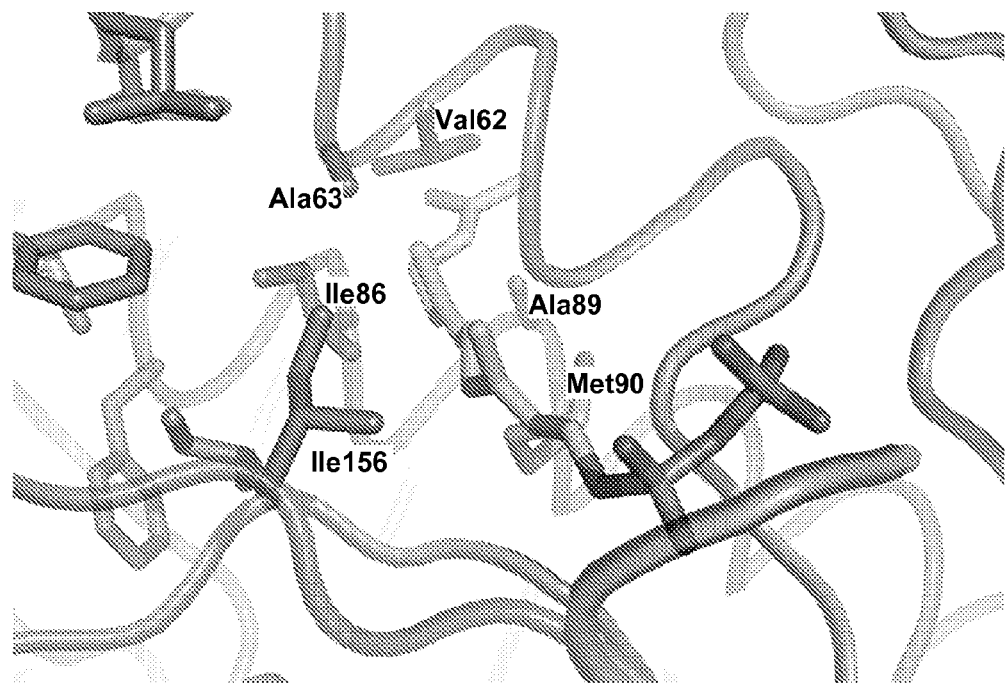
FIG. 14A: This figure depicts a computer graphic molecular model of a possible configuration and binding mode of FPP within the active site of IPK, showing the interaction of FPP with amino acid residues Val62, Ile86, Met90, Ala63, Ala89 and Ile156.

As shown in FIG. 14A, in one binding mode, FPP has potential steric interaction with amino acid residues Val62, Ile86, Met90, Ala63, Ala89 and Ile156, mutation of which could facilitate better binding of FPP. In a first strategy, residues Met90, Ile 156 and/or Ile86 could be mutated to smaller residues (e.g., Ala, Gly, and the like). The terms "smaller," "larger" and the like in the context of amino acid residue size refer, in the customary sense, to the volume occupied by the side chain of the residue. For example, a V62A mutant represents mutation to a smaller residue, whereas a A89V mutant represents mutation to a larger residue. Separately, or in concert, residues Val 62, Ala63 and Ala89 could similarly be mutated to smaller residues. Alternatively, the isoprenyl chain could be redirected by mutation of Ala89 and/or Ala63 to a larger residue, thereby facilitating a change in FPP configuration and binding mode.

Figure 14B:
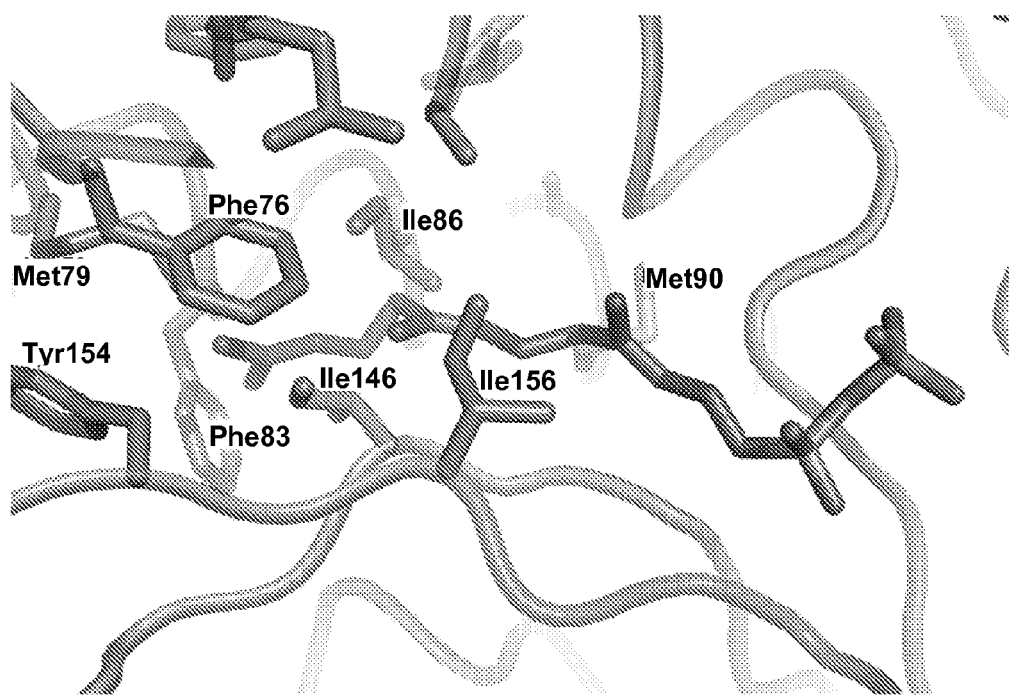
FIG. 14B depicts a computer graphic molecular model of a possible configuration and binding mode of FPP within the active site of IPK, showing the interaction of FPP with amino acid residues Met90, Ile86, Ile156, Ile146, Phe76, Phe83, Tyr154 and Met79.

In another binding mode, residues Met90, Ile86, Ile 156, Ile146, Phe76, Phe83, Tyr154 and Met79 are implicated in steric interaction. See FIG. 14B. This binding mode of FPP suggests a different mutation strategy. Specifically, in a first step residues Met90, Ile156, Ile86 and/or Ile146 could be mutated to a smaller residue. These residues are located proximal to the pyrophosphate "head" of FPP, as opposed to the isoprenyl "tail" thereof. In a second step, residues Phe76, Phe83 and Met79, which are residues more distal to the FPP head pyrophosphate, could be mutated to smaller residues. An additional mutation strategy is suggested in this binding mode, wherein Tyr154 is mutated to a small residue in order to accommodate even longer chain substrate, detectable label (e.g., fluorophoric or spectroscopic label, and the like) or extended isoprenyl tails.

Figure 14C:
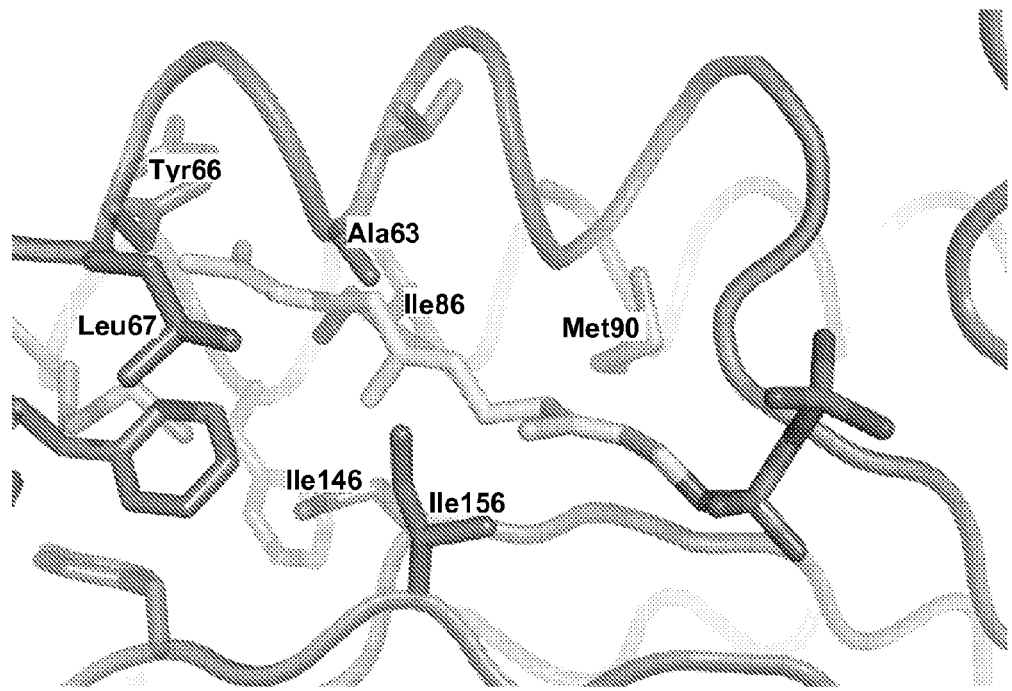
FIG. 14C depicts a computer graphic molecular model of a possible configuration and binding mode of FPP within the active site of IPK, showing the interaction of FPP with amino acid residues Met90, Ile86, Ile146, Ile156, Ala63, Leu67 and Tyr66.

In yet another binding mode, as shown in FIG. 14C, residues Met90, Ile86, Ile146, Ile156, Ala63, Leu67 and Tyr66 potentially interact sterically with FPP. Accordingly, in a incremental mutation strategy, residues Met90, Ile156, Ile86 and Ile146 could be mutated to smaller residues. In another step, residue Ala63 could be mutated to Gly, or alternatively Ala63 could be mutated to a larger residue to facilitate redirection of the substrate chain. Finally, residues Leu67 and Tyr66 could be mutated to smaller residues to facilitate a longer chain substrate within the active site.

Figure 14D:
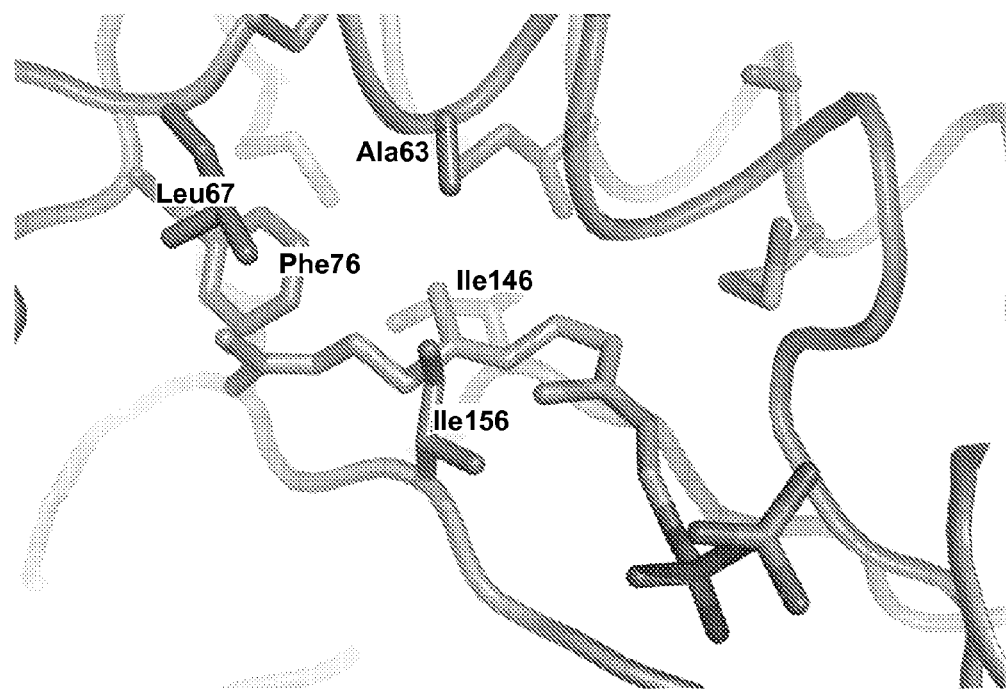
FIG. 14D depicts a computer graphic molecular model of a possible configuration and binding mode of FPP within the active site of IPK, showing the interaction of FPP with amino acid residues Ile146, Ile156, Ala63, Phe76 and Leu67.

In another binding mode, as shown in FIG. 14D, residues Ile146, Ile156, Ala63, Phe76 and Leu67 of IPK are identified as candidates for mutation. In this case, residues Ile146 and Ile156 could be mutated to smaller residues, optionally in concert with mutation of Ala63 to a larger residue to facilitate chain redirection. Again, this binding mode suggests that residues Leu67 and Phe76 could be mutated to facilitate binding of larger substrates within the IPK active site.

Figure 14E:
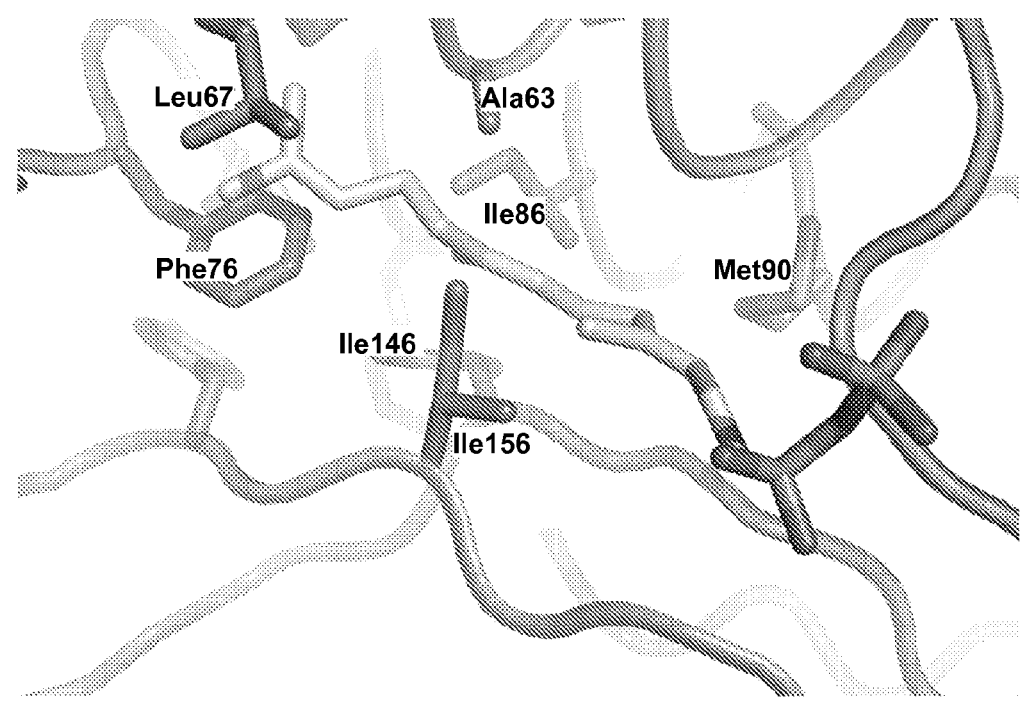
FIG. 14E depicts a computer graphic molecular model of a possible configuration and binding mode of FPP within the active site of IPK, showing the interaction of FPP with amino acid residues Ile86, Ile146, Ile156, Ala63, Met90, Leu67 and Phe76.

In the fifth binding mode of FPP, as shown in FIG. 14E, residues Ile86, Ile146, Ile156, Ala63, Met90, Leu67 and Phe76 are implicated for mutation. In a first step, residues Ile86, Ile146, Ile156, and optionally residues Met90 and Ala63, could be mutated to small residues to facilitate larger substrate binding. This binding mode further suggests that residues Leu67 and Phe76 could be mutated to facilitate binding of larger substrates within the IPK active site.

In view of the plurality of possible configurations and binding modes for FPP within the X-ray crystallographic model of IPK, several generalizations regarding mutation strategy can be made, as examples only which do not limit the design options available to the skilled artisan. First, residues Ile86, Ile146 and Ile156 can be mutated to smaller residues in order to facilitate the binding of larger substrate at the active site of IPK. Second, while Met90 is often observed in these FPP binding models to be somewhat removed from the FPP chain, mutation at Met90 may allow the isoprenyl element of the substrate to access otherwise inaccessible binding modes, and thereby facilitate enzymatic activity. Third, Ala63 and Ala89 may be mutated to smaller residues, or alternatively may be mutated to larger residues. In the latter case, a larger residue at position 63 and/or 89 may facilitate substrate chain redirection and in some cases access to different substrate binding modes. Furthermore, mutation to a larger residue at these positions may impart greater substrate specificity, due for example to the restriction on the possible binding modes available to substrate. Finally, mutation of residues distal from His 60, for example, Phe83, Leu67, Tyr66, Tyr154, Phe76 and/or Met79, to smaller residues can facilitate the binding of longer chain substrate. Without wishing to be bound by any theory, it is believed that mutation of such distal residues would be expected to demonstrate a large effect on IPK activity only if associated with mutations in residues more proximal to the substrate head.

Example 3

Altering Active Site Pocket of IPK

Modeling studies conducted on IPK structures provided herein are useful for the design of mutants having altered properties (e.g., active sites, binding sites, and the like) relative to wild type IPK. For example, methods available for alteration of the active site pocket of IPK, and additional sites relevant for enzymatic activity of IPK, include avoiding steric clash, widening the binding channel, redirecting the chain of substrate and/or product, and bringing the catalytic residue to the phosphate group.

Figure 15:
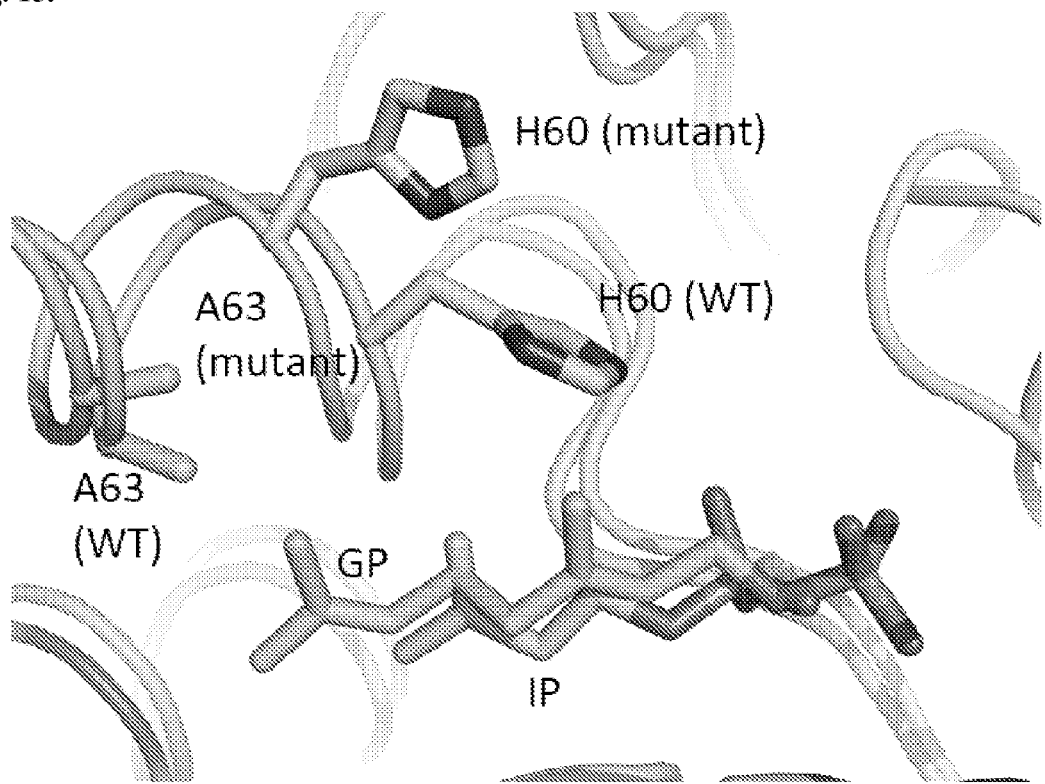
FIG. 15: Avoiding Steric Clashes in the Active Site.

Avoiding Steric Clashes. As depicted in FIG. 15, the tail of the GP molecule has "pushed" A63 upwards in the mutant structure from this perspective, causing the αB helix to reorient and H60 (the catalytic residue) to be further away from the polar phosphate of GP. Mutation to A63G reduce the clash between the GP tail and this residue, thereby reestablishing the relative orientation observed in the wild type IPK model.

Figure 16:
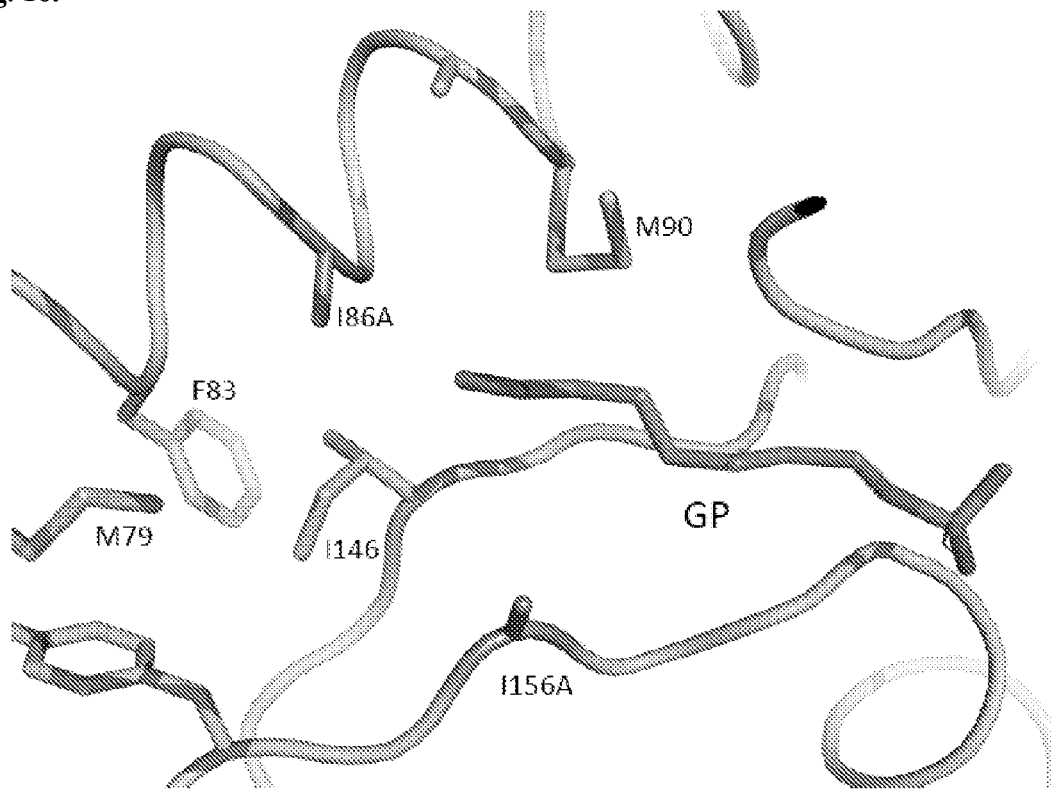
FIG. 16. Widening the Binding Channel in the Active Site.

Widening the Cavity. As depicted in FIG. 16, the distance between I86A and I146 in the IPK I86A/I156A mutant is too narrow for the GP chain to pass between the residues without steric clash. Without wishing to be bound by any theory, it is believed that this observation may explain why the phosphate of GP does not align with the phosphate of IP in the structural alignments. See FIG. 15. Accordingly, the GP chain can fit through I86 and I146 if I86 is mutated even further to a smaller residue (e.g., glycine) and/or if I146 is mutated to a smaller residue (e.g., glycine). Without wishing to be bound by any theory, it is believed that following these two mutations, F83A allows for even longer chains to bind (e.g., FP).

Figure 17:
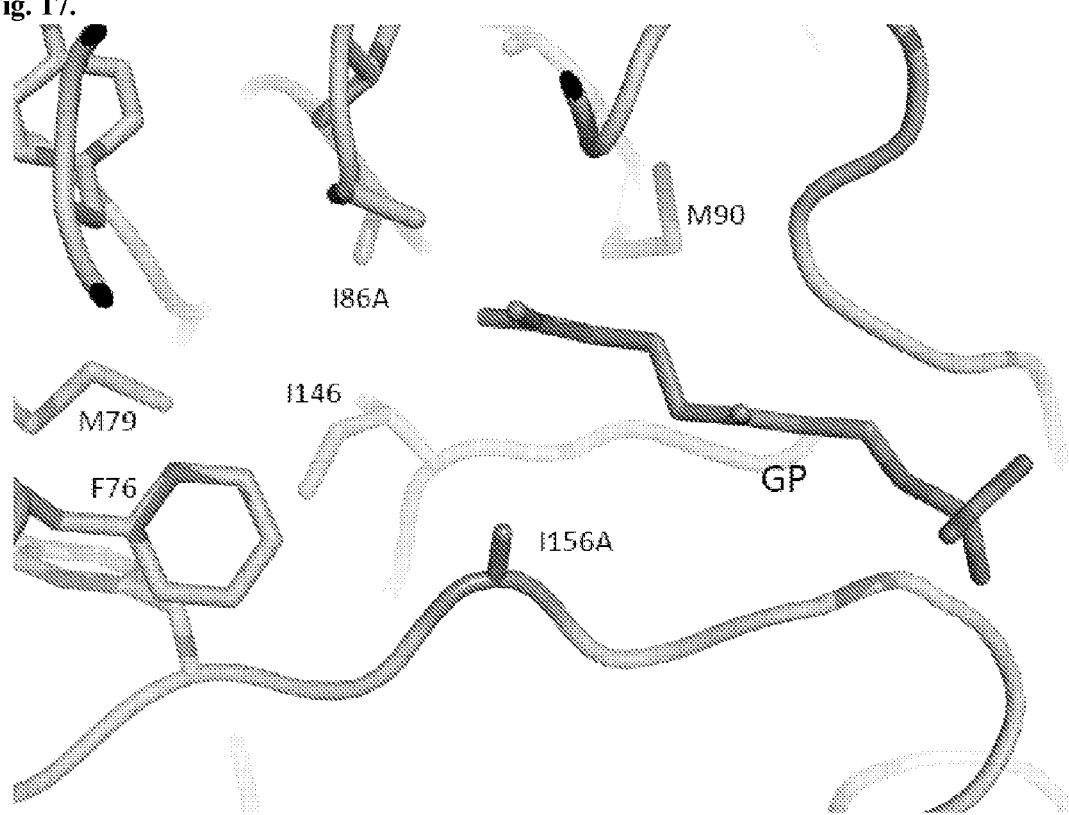
FIG. 17. Redirecting the Chain in the Active Site.

Redirecting the Chain. As depicted in FIG. 17, the chain is redirected in response to a variety of single and multiple mutations. For example, the mutation I86A of a residue larger than Ala (e.g., Ile, Leu and the like) forced the chain downward in the perspective of FIG. 17. The result of this mutation is further facilitated by mutation of I156A to a smaller residues (e.g., Gly) and/or mutation of F76 to a smaller residue (e.g., Ala).

Figure 18:
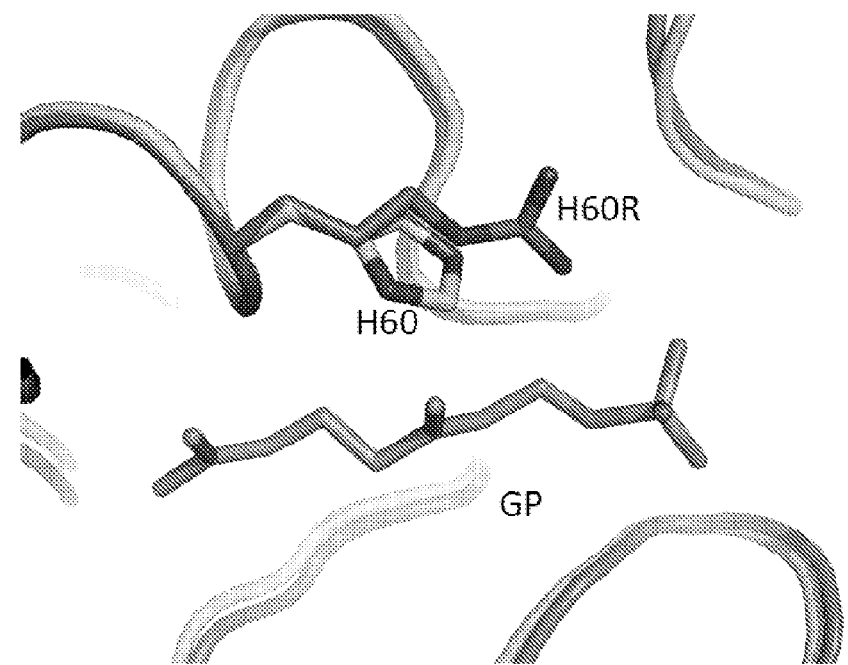
FIG. 18. Bringing the Catalytic Residue to the Phosphate Group in the Active Site.

Bringing the Catalytic Residue to the Phosphate Group. As depicted in FIG. 18, mutation of His60 to a longer side chain (e.g., H60R) encourages the side chain to interact with the phosphate group of GP. Without wishing to be bound by any theory, it is believed that enhanced interaction of the side chain of H60 or larger side chain analog facilitates interaction with substrate and subsequent reaction.

What is claimed is:

1. An isolated protein comprising an amino acid sequence that is at least 90% identical to at least 200 contiguous amino acids of SEQ ID NO: 1;
   wherein the amino acid sequence has a substitution at the position corresponding to Ala63 of SEQ ID NO: 1; and
   wherein said amino acid sequence is capable of catalyzing a reaction between an isoprenoid monophosphate and a phosphate donor to produce an isoprenoid diphosphate.

2. The isolated protein of claim 1, wherein the substitution at Ala63 is a size reducing amino acid substitution or a size increasing amino acid substitution mutation.

3. The isolated protein of claim 1, wherein said amino acid sequence comprises a mutation at the amino acid corresponding to Tyr66, Leu67, Phe76, Ile86, Ala89, Met90, Ile146, Ile156, or of SEQ ID NO: 1.

4. The isolated protein of claim 1, wherein said amino acid sequence comprises a mutation at the amino acid corresponding to Leu67, Phe76, Ile146, or Ile156, of SEQ ID NO: 1.

* * * * *

UNITED STATES PATENT AND TRADEMARK OFFICE
CERTIFICATE OF CORRECTION

PATENT NO.        : 9,051,555 B2
APPLICATION NO.   : 13/384534
DATED             : June 9, 2015
INVENTOR(S)       : Joseph P. Noel et al.

It is certified that error appears in the above-identified patent and that said Letters Patent is hereby corrected as shown below:

In the claims

In claim 3, column 72, line 45 and 46 please insert --or-- between Ile 146, Ile 156 and delete "or" before of SEQ ID No:1.

should read as follows:

3. The isolated protein of claim 1, wherein said amino acid sequence comprises a mutation at the amino acid corresponding to Tyr66, Leu67, Phe76, Ile86, Ala89, Met90, Ile146 or Ile156 of SEQ ID NO: 1.

Signed and Sealed this
Fifteenth Day of December, 2015

Michelle K. Lee
*Director of the United States Patent and Trademark Office*

SEQUENCE LISTING

<160> NUMBER OF SEQ ID NOS: 22

<210> SEQ ID NO 1
<211> LENGTH: 260
<212> TYPE: PRT
<213> ORGANISM: Methanocaldococcus jannaschii

<400> SEQUENCE: 1

Met Leu Thr Ile Leu Lys Leu Gly Gly Ser Ile Leu Ser Asp Lys Asn

```
              1               5                  10                 15
          Val Pro Tyr Ser Ile Lys Trp Asp Asn Leu Glu Arg Ile Ala Met Glu
                          20                 25                 30

Ile Lys Asn Ala Leu Asp Tyr Tyr Lys Asn Gln Asn Lys Glu Ile Lys
                          35                 40                 45

Leu Ile Leu Val His Gly Gly Gly Ala Phe Gly His Pro Val Ala Lys
                   50                 55                 60

Lys Tyr Leu Lys Ile Glu Asp Gly Lys Lys Ile Phe Ile Asn Met Glu
          65                 70                 75                 80

Lys Gly Phe Trp Glu Ile Gln Arg Ala Met Arg Arg Phe Asn Asn Ile
                             85                 90                 95

Ile Ile Asp Thr Leu Gln Ser Tyr Asp Ile Pro Ala Val Ser Ile Gln
                          100                105                110

Pro Ser Ser Phe Val Val Phe Gly Asp Lys Leu Ile Phe Asp Thr Ser
                          115                120                125

Ala Ile Lys Glu Met Leu Lys Arg Asn Leu Val Pro Val Ile His Gly
                   130                135                140

Asp Ile Val Ile Asp Asp Lys Asn Gly Tyr Arg Ile Ile Ser Gly Asp
          145                150                155                160

Asp Ile Val Pro Tyr Leu Ala Asn Glu Leu Lys Ala Asp Leu Ile Leu
                             165                170                175

Tyr Ala Thr Asp Val Asp Gly Val Leu Ile Asp Asn Lys Pro Ile Lys
                          180                185                190

Arg Ile Asp Lys Asn Asn Ile Tyr Lys Ile Leu Asn Tyr Leu Ser Gly
                          195                200                205

Ser Asn Ser Ile Asp Val Thr Gly Gly Met Lys Tyr Lys Ile Glu Met
                   210                215                220

Ile Arg Lys Asn Lys Cys Arg Gly Phe Val Phe Asn Gly Asn Lys Ala
          225                230                235                240

Asn Asn Ile Tyr Lys Ala Leu Leu Gly Glu Val Glu Gly Thr Glu Ile
                             245                250                255

Asp Phe Ser Glu
                     260

<210> SEQ ID NO 2
<211> LENGTH: 266
<212> TYPE: PRT
<213> ORGANISM: Streptomyces wedmorensis

<400> SEQUENCE: 2

Met Thr Pro Asp Phe Leu Ala Ile Lys Val Gly Gly Ser Leu Phe Ser
1               5                  10                 15

Arg Lys Asp Glu Pro Gly Ser Leu Asp Asp Ala Val Thr Arg Phe
                20                 25                 30

Ala Arg Asn Phe Ala Arg Leu Ala Glu Thr Tyr Arg Gly Arg Met Val
                35                 40                 45

Leu Ile Ser Gly Gly Gly Ala Phe Gly His Gly Ala Ile Arg Asp His
         50                 55                 60

Asp Ser Thr His Ala Phe Ser Leu Ala Gly Leu Thr Glu Ala Thr Phe
65                 70                 75                 80

Glu Val Lys Lys Arg Trp Ala Glu Lys Leu Arg Gly Ile Gly Val Asp
                   85                 90                 95

Ala Phe Pro Leu Gln Leu Ala Ala Met Cys Thr Leu Arg Asn Gly Ile
                100                105                110
```

```
Pro Gln Leu Arg Ser Glu Val Leu Arg Asp Val Leu Asp His Gly Ala
            115                 120                 125
Leu Pro Val Leu Ala Gly Asp Ala Leu Phe Asp Glu His Gly Lys Leu
        130                 135                 140
Trp Ala Phe Ser Ser Asp Arg Val Pro Glu Val Leu Leu Pro Met Val
145                 150                 155                 160
Glu Gly Arg Leu Arg Val Val Thr Leu Thr Asp Val Asp Gly Ile Val
                165                 170                 175
Thr Asp Gly Ala Gly Gly Asp Thr Ile Leu Pro Glu Val Asp Ala Arg
            180                 185                 190
Ser Pro Glu Gln Ala Tyr Ala Ala Leu Trp Gly Ser Ser Glu Trp Asp
        195                 200                 205
Ala Thr Gly Ala Met His Thr Lys Leu Asp Ala Leu Val Thr Cys Ala
    210                 215                 220
Arg Arg Gly Ala Glu Cys Phe Ile Met Arg Gly Asp Pro Gly Ser Asp
225                 230                 235                 240
Leu Glu Phe Leu Thr Ala Pro Phe Ser Ser Trp Pro Ala His Val Arg
                245                 250                 255
Ser Thr Arg Ile Thr Thr Thr Ala Ser Ala
            260                 265

<210> SEQ ID NO 3
<211> LENGTH: 248
<212> TYPE: PRT
<213> ORGANISM: Chlamydophila pneumoniae

<400> SEQUENCE: 3

Met Ala Lys Gln Thr Arg Arg Val Leu Phe Lys Ile Ser Gly Glu Ala
1               5                   10                  15
Leu Ser Lys Asp Ser Ser Asn Arg Ile Asp Glu Met Arg Leu Ser Arg
            20                  25                  30
Leu Val Ser Glu Leu Arg Ala Val Arg Asn Asn Asp Ile Glu Ile Ala
        35                  40                  45
Leu Val Ile Gly Gly Gly Asn Ile Leu Arg Gly Leu Ala Glu Gln Lys
    50                  55                  60
Glu Leu Gln Ile Asn Arg Val Ser Ala Asp Gln Met Gly Met Leu Ala
65                  70                  75                  80
Thr Leu Ile Asn Gly Met Ala Val Ala Asp Ala Leu Lys Ala Glu Asp
                85                  90                  95
Ile Pro Cys Leu Leu Thr Ser Thr Leu Ser Cys Pro Gln Leu Ala Asp
            100                 105                 110
Leu Tyr Thr Pro Gln Lys Ser Ile Glu Ala Leu Asp Gln Gly Lys Ile
        115                 120                 125
Leu Ile Cys Thr Thr Gly Ala Gly Ser Pro Tyr Leu Thr Thr Asp Thr
    130                 135                 140
Gly Ala Ala Leu Arg Ala Cys Glu Leu Asn Val Asp Val Leu Ile Lys
145                 150                 155                 160
Ala Thr Met His Val Asp Gly Val Tyr Asp Lys Asp Pro Arg Leu Phe
                165                 170                 175
Pro Asp Ala Val Lys Tyr Asp Phe Val Ser Tyr Lys Asp Phe Leu Ser
            180                 185                 190
Asn Gln Leu Gly Val Met Asp Ala Ser Ala Ile Ser Leu Cys Met Asp
        195                 200                 205
Ser His Ile Pro Ile Arg Val Phe Ser Phe Leu Gln Ser Leu Glu
    210                 215                 220
```

```
Lys Ala Leu Phe Asp Pro Thr Ile Gly Thr Leu Val Ser Glu Asp Val
225                 230                 235                 240

Asn His Val Cys Ser Pro Arg His
                245
```

<210> SEQ ID NO 4
<211> LENGTH: 241
<212> TYPE: PRT
<213> ORGANISM: Escherichia coli

<400> SEQUENCE: 4

```
Met Ala Thr Asn Ala Lys Pro Val Tyr Lys Arg Ile Leu Leu Lys Leu
1               5                   10                  15

Ser Gly Glu Ala Leu Gln Gly Thr Glu Gly Phe Gly Ile Asp Ala Ser
                20                  25                  30

Ile Leu Asp Arg Met Ala Gln Glu Ile Lys Glu Leu Val Glu Leu Gly
            35                  40                  45

Ile Gln Val Gly Val Val Ile Gly Gly Gly Asn Leu Phe Arg Gly Ala
        50                  55                  60

Gly Leu Ala Lys Ala Gly Met Asn Arg Val Val Gly Asp His Met Gly
65                  70                  75                  80

Met Leu Ala Thr Val Met Asn Gly Leu Ala Met Arg Asp Ala Leu His
                85                  90                  95

Arg Ala Tyr Val Asn Ala Arg Leu Met Ser Ala Ile Pro Leu Asn Gly
            100                 105                 110

Val Cys Asp Ser Tyr Ser Trp Ala Glu Ala Ile Ser Leu Leu Arg Asn
        115                 120                 125

Asn Arg Val Val Ile Leu Ser Ala Gly Thr Gly Asn Pro Phe Phe Thr
130                 135                 140

Thr Asp Ser Ala Ala Cys Leu Arg Gly Ile Glu Ile Glu Ala Asp Val
145                 150                 155                 160

Val Leu Lys Ala Thr Lys Val Asp Gly Val Phe Thr Ala Asp Pro Ala
                165                 170                 175

Lys Asp Pro Thr Ala Thr Met Tyr Glu Gln Leu Thr Tyr Ser Glu Val
            180                 185                 190

Leu Glu Lys Glu Leu Lys Val Met Asp Leu Ala Ala Phe Thr Leu Ala
        195                 200                 205

Arg Asp His Lys Leu Pro Ile Arg Val Phe Asn Met Asn Lys Pro Gly
210                 215                 220

Ala Leu Arg Arg Val Val Met Gly Glu Lys Glu Gly Thr Leu Ile Thr
225                 230                 235                 240

Glu
```

<210> SEQ ID NO 5
<211> LENGTH: 242
<212> TYPE: PRT
<213> ORGANISM: Rickettsia prowazekii

<400> SEQUENCE: 5

```
Met Ala Ser Asp Ile Asn Ala Leu Lys Tyr Lys Lys Val Leu Leu Lys
1               5                   10                  15

Val Ser Gly Glu Ala Leu Met Gly Asn Lys Gln Phe Gly His Glu Tyr
                20                  25                  30

Glu Val Ile Lys Lys Ile Ala Glu Asp Ile Lys Glu Val Ile Asp Leu
            35                  40                  45
```

```
Gly Leu Glu Val Ala Ile Val Val Gly Gly Asn Ile Tyr Arg Gly
     50                  55                  60

Ile Asn Ala Ala Leu Val Gly Met Asp Arg Ala Ser Ala Asp Tyr Ile
 65                  70                  75                  80

Gly Met Leu Ala Thr Val Met Asn Ala Leu Thr Leu Gln Asn Val Met
                 85                  90                  95

Glu Ser Leu Gly Ile Tyr Thr Arg Val Leu Ser Ala Ile Pro Met Met
                100                 105                 110

Ser Val Cys Glu Pro Tyr Ile Arg Arg Lys Ala Lys Arg His Met Glu
            115                 120                 125

Lys Lys Arg Val Val Ile Phe Ala Gly Gly Thr Gly Asn Pro Phe Cys
130                 135                 140

Thr Thr Asp Ser Ala Ala Val Leu Arg Ala Ile Glu Met Asn Cys Asp
145                 150                 155                 160

Ile Leu Leu Lys Ala Thr Gln Val Asp Gly Val Tyr Asp Ser Asp Pro
                165                 170                 175

Lys Lys Asn Pro Asn Ala Lys Lys Tyr Phe Thr Ile Ser Tyr Lys Asp
            180                 185                 190

Val Ile Asn Asn His Leu Gln Val Met Asp Thr Ala Ala Ile Ala Val
                195                 200                 205

Ala Arg Glu Asn Lys Leu Pro Ile Arg Val Phe Ser Ile Lys Glu His
210                 215                 220

Gly Asn Phe Ala Arg Val Ile Gln Asp Lys Gly Gln Tyr Thr Thr Ile
225                 230                 235                 240

Gly Glu

<210> SEQ ID NO 6
<211> LENGTH: 240
<212> TYPE: PRT
<213> ORGANISM: Aquifex aeolicus

<400> SEQUENCE: 6

Met Glu Glu Lys Pro Lys Tyr Lys Arg Ile Leu Leu Lys Leu Ser Gly
 1               5                  10                  15

Glu Ala Phe Ala Gly Glu Gln Gly Tyr Gly Ile Asp Pro Ala Phe Leu
                20                  25                  30

Glu Tyr Ile Ser His Glu Ile Lys Asn Val Tyr Asp Leu Gly Val Gln
            35                  40                  45

Val Ala Ile Val Ile Gly Gly Asn Ile Phe Arg Gly Phe Gln Gly
     50                  55                  60

Lys Glu Ile Gly Val Asp Arg Ala Thr Ala Asp Tyr Met Gly Met Leu
 65                  70                  75                  80

Ala Thr Val Ile Asn Ala Leu Ala Leu Gln Ser Ala Leu Glu Asn His
                 85                  90                  95

Val Asn Ile Pro Thr Arg Val Leu Ser Ala Ile Glu Met Arg Gln Val
                100                 105                 110

Ala Glu Pro Tyr Ile Arg Arg Ala Ile Arg His Leu Glu Lys Gly
            115                 120                 125

Arg Ile Val Ile Phe Ala Gly Gly Thr Gly Asn Pro Phe Phe Ser Thr
130                 135                 140

Asp Thr Ala Ala Ala Leu Arg Ala Ala Glu Ile Gly Ala Glu Val Leu
145                 150                 155                 160

Ile Lys Ala Thr Lys Val Gly Gly Ile Tyr Asp Lys Asp Pro Glu Lys
                165                 170                 175
```

```
Tyr Pro Asp Ala Val Leu Ile Lys Glu Ile Ser Tyr Leu Glu Val Ile
            180                 185                 190

Asn Met Gly Leu Lys Val Met Asp His Thr Ala Leu Thr Leu Cys Lys
        195                 200                 205

Glu Asn Glu Ile Pro Ile Ile Val Leu Asn Val Lys Glu Lys Gly Asn
    210                 215                 220

Leu Arg Arg Ala Val Leu Gly Glu Val Gly Ser Val Val Arg Gly
225                 230                 235                 240

<210> SEQ ID NO 7
<211> LENGTH: 260
<212> TYPE: PRT
<213> ORGANISM: Unknown
<220> FEATURE:
<223> OTHER INFORMATION: Synechocystis species

<400> SEQUENCE: 7

Met Gly Gly Ile Leu Arg Leu Thr Leu Ile Pro Cys Leu Tyr Ile Asn
1               5                   10                  15

Gly Asp Gly Gly Met Ser Tyr Gln Arg Val Leu Leu Lys Leu Ser Gly
            20                  25                  30

Glu Ala Leu Met Gly Asp Leu Gly Tyr Gly Ile Asp Pro Ala Val Val
        35                  40                  45

Gly Thr Ile Ala Gln Glu Ile Lys Asp Val Leu Gln Ala Gly Val Gln
    50                  55                  60

Leu Ala Ile Val Val Gly Gly Gly Asn Ile Phe Arg Gly Val Lys Ala
65                  70                  75                  80

Ser Ala Ala Gly Met Asp Arg Ala Thr Ala Asp Tyr Ile Gly Met Ile
                85                  90                  95

Ala Thr Val Met Asn Ala Met Thr Leu Gln Asp Ala Leu Glu Gln Met
            100                 105                 110

Asp Ile Pro Thr Arg Val Leu Thr Ala Ile Ala Met Gln Glu Val Ala
        115                 120                 125

Glu Pro Tyr Ile Arg Arg Arg Ala Ile Arg His Leu Glu Lys Gly Arg
    130                 135                 140

Val Val Ile Phe Gly Ala Gly Ser Gly Asn Pro Phe Phe Thr Thr Asp
145                 150                 155                 160

Thr Thr Ala Ala Leu Arg Ala Ala Glu Ile Asp Ala Glu Val Val Phe
                165                 170                 175

Lys Ala Thr Lys Val Asp Gly Val Tyr Asp Ser Asp Pro Lys Thr Asn
            180                 185                 190

Pro Asn Ala Arg Arg Phe Thr Thr Leu Thr Tyr Ser His Val Leu Ala
        195                 200                 205

Glu Asp Leu Lys Val Met Asp Ser Thr Ala Ile Ala Leu Cys Lys Asp
    210                 215                 220

Asn Asn Ile Pro Ile Met Ile Phe Asp Leu Gly Val Pro Gly Asn Ile
225                 230                 235                 240

Val Arg Ala Ile Lys Gly Glu Ala Val Gly Thr Leu Val Gly Glu Asn
                245                 250                 255

Cys Glu Val Ser
            260

<210> SEQ ID NO 8
<211> LENGTH: 256
<212> TYPE: PRT
<213> ORGANISM: Methanococcus maripaludis
```

```
<400> SEQUENCE: 8

Met Phe Ala Ile Leu Lys Leu Gly Gly Ser Ile Leu Cys Asp Lys Asn
1               5                   10                  15

Val Pro Tyr Ser Ile Asn Trp Glu Asn Leu Glu Asn Ile Ala Ile Glu
            20                  25                  30

Ile Lys Glu Ala Ile Glu Tyr Tyr Ser Ser Lys Asn Glu Asp Phe Lys
        35                  40                  45

Leu Ile Ile Val His Gly Gly Ser Phe Gly His Pro Val Ala Lys
    50                  55                  60

Lys Tyr Leu Lys Asn Glu Lys Phe Glu Asp Met Gly Lys Gly Tyr Trp
65              70                  75                  80

Glu Ile Gln Lys Ala Met Arg Lys Phe Asn Asn Ile Val Ile Glu Glu
                85                  90                  95

Leu Gln Asn Phe Glu Pro Ala Val Ser Ile Gln Ala Ser Ser Phe Ile
            100                 105                 110

Thr Phe Asn His Lys Ser Asn Leu His Phe Asp Thr Asn Ala Ile Glu
        115                 120                 125

Lys Met Leu Asp Lys Gly Leu Ile Pro Val Ile His Gly Asp Ile Val
130                 135                 140

Ile Asp Glu Lys Thr Asp Asn Phe Lys Ile Phe Ser Gly Asp His Ala
145                 150                 155                 160

Leu Pro Phe Leu Ser Lys Lys Leu Asn Pro Asp Leu Ser Leu His Ala
                165                 170                 175

Ser Asp Val Asp Gly Val Trp Asp Ser Glu Phe Lys Ile Ile Glu Asn
            180                 185                 190

Ile Asn Ser Lys Asn Ile Glu Asp Val Leu Lys Ser Leu Lys Pro Ser
        195                 200                 205

Asn Lys Glu Asp Val Thr Gly Gly Met His Leu Lys Val Met Glu Cys
210                 215                 220

Tyr Asn Leu Gly Ile Glu Thr Ile Ile Phe Asn Gly Asn Lys Lys Arg
225                 230                 235                 240

Asn Ile Tyr Asn Ala Leu Leu Lys Asn Val Lys Gly Thr Leu Ile Asn
                245                 250                 255

<210> SEQ ID NO 9
<211> LENGTH: 281
<212> TYPE: PRT
<213> ORGANISM: Trichoplax adhaearens

<400> SEQUENCE: 9

Met Ala Leu Glu Asn Arg His Val Asp Cys Ile Ile Lys Leu Gly Gly
1               5                   10                  15

Ser Ala Ile Thr Ser Lys Gln His Leu Glu Lys Ala Asn Thr Gln Ala
            20                  25                  30

Ile Asn Ile Ala Ala Ser His Val His Glu Met Thr Arg Lys Cys Val
        35                  40                  45

Ile Val His Gly Ala Gly Ser Phe Gly His Phe Ala Lys Lys Tyr
    50                  55                  60

Asn Ile Ala Thr Gly Phe Asn Asp Thr Asp Phe Glu Gln Gln Arg Ile
65              70                  75                  80

Gly Phe Ser Gln Thr Arg Leu Ser Val Thr Lys Leu Asn His Ile Ile
                85                  90                  95

Val Gln Ala Leu Ile Glu Lys Asp Val Pro Ala Val Ser Ile Ser Pro
            100                 105                 110
```

```
Cys Gly Leu Trp Lys Thr Thr Asp Arg Ser Val Thr Ser Thr Phe Leu
            115                 120                 125
Gln Pro Ile Asn Asp Leu Leu Arg Ala Gly Phe Val Pro Val His
        130                 135                 140
Gly Asp Ala Val Ile Asp Thr Ser Leu Gly Cys Thr Ile Leu Ser Gly
145                 150                 155                 160
Asp Thr Ile Ile Gln Ile Leu Ala Glu Asn Leu Cys Pro Lys Arg Ile
                165                 170                 175
Ile Phe Ile Thr Asp Thr Asn Gly Ile Tyr Asp Arg Pro His Asn
                180                 185                 190
Asp Asp Ala Lys Leu Leu Arg Tyr Ile Ser Val Thr Lys Asp Gly Lys
        195                 200                 205
Val Thr Asn Glu Ile Glu Thr Ser Gln Leu Glu His Asp Val Thr Gly
    210                 215                 220
Gly Val Gln Thr Lys Ile Ala Ser Ala Ala His Ile Val Ser Lys Cys
225                 230                 235                 240
Asn Ile Pro Val His Val Val Lys Leu Gly Ser Ala Ala Ala Trp Lys
                245                 250                 255
Leu Leu Asp Lys Gly Glu Leu Glu Ser Asp Ile Ala Thr Thr Ile
            260                 265                 270
Thr Leu Gln Glu Ser Glu Tyr Pro Lys
        275                 280

<210> SEQ ID NO 10
<211> LENGTH: 332
<212> TYPE: PRT
<213> ORGANISM: Arabidopsis thaliana

<400> SEQUENCE: 10

Met Glu Leu Asn Ile Ser Glu Ser Arg Ser Arg Ser Ile Arg Cys Ile
1               5                   10                  15
Val Lys Leu Gly Gly Ala Ala Ile Thr Cys Lys Asn Glu Leu Glu Lys
            20                  25                  30
Ile His Asp Glu Asn Leu Glu Val Val Ala Cys Gln Leu Arg Gln Ala
        35                  40                  45
Met Leu Glu Gly Ser Ala Pro Ser Lys Val Ile Gly Met Asp Trp Ser
    50                  55                  60
Lys Arg Pro Gly Ser Ser Glu Ile Ser Cys Asp Val Asp Ile Gly
65                  70                  75                  80
Asp Gln Lys Ser Ser Glu Phe Ser Lys Phe Val Val His Gly Ala
                85                  90                  95
Gly Ser Phe Gly His Phe Gln Ala Ser Arg Ser Gly Val His Lys Gly
                100                 105                 110
Gly Leu Glu Lys Pro Ile Val Lys Ala Gly Phe Val Ala Thr Arg Ile
            115                 120                 125
Ser Val Thr Asn Leu Asn Leu Glu Ile Val Arg Ala Leu Ala Arg Glu
        130                 135                 140
Gly Ile Pro Thr Ile Gly Met Ser Pro Phe Ser Cys Gly Trp Ser Thr
145                 150                 155                 160
Ser Lys Arg Asp Val Ala Ser Ala Asp Leu Ala Thr Val Ala Lys Thr
                165                 170                 175
Ile Asp Ser Gly Phe Val Pro Val Leu His Gly Asp Ala Val Leu Asp
                180                 185                 190
Asn Ile Leu Gly Cys Thr Ile Leu Ser Gly Asp Val Ile Ile Arg His
            195                 200                 205
```

```
Leu Ala Asp His Leu Lys Pro Glu Tyr Val Phe Leu Thr Asp Val
        210                 215                 220

Leu Gly Val Tyr Asp Arg Pro Ser Pro Ser Glu Pro Asp Ala Val
225                 230                 235                 240

Leu Leu Lys Glu Ile Ala Val Gly Glu Asp Gly Ser Trp Lys Val Val
            245                 250                 255

Asn Pro Leu Leu Glu His Thr Asp Lys Lys Val Asp Tyr Ser Val Ala
            260                 265                 270

Ala His Asp Thr Thr Gly Gly Met Glu Thr Lys Ile Ser Glu Ala Ala
            275                 280                 285

Met Ile Ala Lys Leu Gly Val Asp Val Tyr Ile Val Lys Ala Ala Thr
        290                 295                 300

Thr His Ser Gln Arg Ala Leu Asn Gly Asp Leu Arg Asp Ser Val Pro
305                 310                 315                 320

Glu Asp Trp Leu Gly Thr Ile Ile Arg Phe Ser Lys
                325                 330

<210> SEQ ID NO 11
<211> LENGTH: 297
<212> TYPE: PRT
<213> ORGANISM: Branchiostoma floridae

<400> SEQUENCE: 11

Met Val His Lys Cys Cys Leu Cys Gln Cys Thr Asp Val Leu Ser Gly
1               5                   10                  15

Leu Glu Cys Ile Val Lys Leu Gly Gly Ser Ala Val Thr Asp Lys Ser
            20                  25                  30

Thr Leu Glu Thr Pro Arg Leu Asp Ala Ile Arg Ala Ala Asp Ile
        35                  40                  45

Ile Ser Gln Val Arg Gly Arg Cys Ile Val Val His Gly Ala Gly Ser
    50                  55                  60

Phe Gly His Phe Gln Ala Arg Glu His Gly Val Val Trp Gly Tyr Arg
65                  70                  75                  80

Asp Lys Glu Thr Asp Thr Glu Val Gln Thr Val Lys Leu Gly Phe Cys
                85                  90                  95

Arg Thr Arg Gln Ser Val Thr Lys Leu Leu His Ile Ile Thr Glu Glu
            100                 105                 110

Phe Val Arg Leu Gly Ile Pro Ala Val Gly Val Ser Pro Leu Ser Ser
        115                 120                 125

Trp Val Thr Asp Asp Ala Ser Val Val Lys Ala Asp Thr Asp Asn Ile
130                 135                 140

Arg Asp Met Leu Leu Glu Gly Phe Leu Pro Val Met His Gly Asp Ala
145                 150                 155                 160

Val Leu Asp Arg Lys Arg Gly Cys Thr Ile Leu Ser Gly Asp Thr Ile
                165                 170                 175

Ile Lys His Leu Cys Ser Val Phe Arg Pro Arg Val Phe Leu
            180                 185                 190

Thr Asp Val Pro Gly Ile Tyr Asp Arg Pro Pro Glu Gln Pro Gly Ala
        195                 200                 205

Gln Leu Ile Pro Glu Ile Gln Val Asp Arg Asp Arg Lys Leu His Val
    210                 215                 220

Ser Ile Ala Thr Ser Ser Gln Ala His Asp Val Thr Gly Gly Ile Ala
225                 230                 235                 240

Leu Lys Leu Lys Ser Ala Ile Asp Ile Val Thr Glu Ser Asn Gly His
```

```
                    245                 250                 255
Thr Cys Val Met Val Cys Gly Ile Gln Ser Gln Ala Ala Val Arg Ala
                260                 265                 270

Cys Val Glu Gly Gln Leu Pro Gln Gly Thr Gly Thr Ile Val Gln Asn
            275                 280                 285

Ile Ser Lys His Pro Asp Glu Val Thr
        290                 295

<210> SEQ ID NO 12
<211> LENGTH: 40
<212> TYPE: DNA
<213> ORGANISM: Artificial Sequence
<220> FEATURE:
<223> OTHER INFORMATION: Synthetic polynucleotide DNA for forward primer
      for IPK of M. jannaschii

<400> SEQUENCE: 12
cccatggcgg atccatgcta accatattaa aattaggagg                             40

<210> SEQ ID NO 13
<211> LENGTH: 40
<212> TYPE: DNA
<213> ORGANISM: Artificial Sequence
<220> FEATURE:
<223> OTHER INFORMATION: Synthetic polynucleotide DNA for reverse primer
      for IPK of M. jannaschii

<400> SEQUENCE: 13
tggtggtgct cgagttattc tgaaaaatca atttctgttc                             40

<210> SEQ ID NO 14
<211> LENGTH: 42
<212> TYPE: DNA
<213> ORGANISM: Artificial Sequence
<220> FEATURE:
<223> OTHER INFORMATION: Synthetic polynucleotide DNA for forward primer
      for IPK of M. maripaludis

<400> SEQUENCE: 14
gagggcggat caaaattcta acgtttgtaa ggtacccttg gt                          42

<210> SEQ ID NO 15
<211> LENGTH: 42
<212> TYPE: DNA
<213> ORGANISM: Artificial Sequence
<220> FEATURE:
<223> OTHER INFORMATION: Synthetic polynucleotide DNA for reverse primer
      for IPK of M. maripaludis

<400> SEQUENCE: 15
gtggtgctcg agttaattta ttaatgttcc ttttacattt tt                          42

<210> SEQ ID NO 16
<211> LENGTH: 40
<212> TYPE: DNA
<213> ORGANISM: Artificial Sequence
<220> FEATURE:
<223> OTHER INFORMATION: Synthetic polynucleotide DNA for forward primer
      for IPK of M. jannaschii H60A

<400> SEQUENCE: 16
cgtccatgga ggaggagctt ttggtgctcc agtagctaaa                             40

<210> SEQ ID NO 17
<211> LENGTH: 40
```

-continued

```
<212> TYPE: DNA
<213> ORGANISM: Artificial Sequence
<220> FEATURE:
<223> OTHER INFORMATION: Synthetic polynucleotide DNA for reverse primer
      for IPK of M. jannaschii H60A

<400> SEQUENCE: 17
tttagctact ggagcaccaa aagctcctcc tccatggacg                              40

<210> SEQ ID NO 18
<211> LENGTH: 41
<212> TYPE: DNA
<213> ORGANISM: Artificial Sequence
<220> FEATURE:
<223> OTHER INFORMATION: Synthetic polynucleotide DNA for forward primer
      for IPK of M. jannaschii H60N

<400> SEQUENCE: 18
atggaggagg agcttttggt aatccagtag ctaaaaaata c                            41

<210> SEQ ID NO 19
<211> LENGTH: 41
<212> TYPE: DNA
<213> ORGANISM: Artificial Sequence
<220> FEATURE:
<223> OTHER INFORMATION: Synthetic polynucleotide DNA for reverse primer
      for IPK of M. jannaschii H60N

<400> SEQUENCE: 19 gtattttta gctactggat taccaaaagc tcctcctcca t                             41

<210> SEQ ID NO 20
<211> LENGTH: 36
<212> TYPE: DNA
<213> ORGANISM: Artificial Sequence
<220> FEATURE:
<223> OTHER INFORMATION: Synthetic polynucleotide DNA for forward primer
      for IPK of M. jannaschii H60Q

<400> SEQUENCE: 20
catggaggag gagctttttgg tcagccagta gctaaa                                 36

<210> SEQ ID NO 21
<211> LENGTH: 36
<212> TYPE: PRT
<213> ORGANISM: Artificial Sequence
<220> FEATURE:
<223> OTHER INFORMATION: Synthetic polynucleotide DNA for reverse primer
      for IPK of M. jannaschii H60Q

<400> SEQUENCE: 21
```

Thr Thr Thr Ala Gly Cys Thr Ala Cys Thr Gly Gly Cys Thr Gly Ala
1               5                   10                  15

Cys Cys Ala Ala Ala Ala Gly Cys Thr Cys Cys Thr Cys Cys Thr Cys
                20                  25                  30

Cys Ala Thr Gly
        35

```
<210> SEQ ID NO 22
<211> LENGTH: 258
<212> TYPE: PRT
<213> ORGANISM: Escherichia coli

<400> SEQUENCE: 22
```

Met Met Asn Pro Leu Ile Ile Lys Leu Gly Gly Val Leu Leu Asp Ser
1               5                   10                  15

```
Glu Glu Ala Leu Glu Arg Leu Phe Ser Ala Leu Val Asn Tyr Arg Glu
         20                  25                  30

Ser His Gln Arg Pro Leu Val Ile Val His Gly Gly Cys Val Val
     35                  40                  45

Asp Glu Leu Met Lys Gly Leu Asn Leu Pro Val Lys Lys Lys Asn Gly
     50                  55                  60

Leu Arg Val Thr Pro Ala Asp Gln Ile Asp Ile Ile Thr Gly Ala Leu
65                  70                  75                  80

Ala Gly Thr Ala Asn Lys Thr Leu Leu Ala Trp Ala Lys Lys His Gln
             85                  90                  95

Ile Ala Ala Val Gly Leu Phe Leu Gly Asp Gly Asp Ser Val Lys Val
             100                 105                 110

Thr Gln Leu Asp Glu Glu Leu Gly His Val Gly Leu Ala Gln Pro Gly
             115                 120                 125

Ser Pro Lys Leu Ile Asn Ser Leu Leu Glu Asn Gly Tyr Leu Pro Val
             130                 135                 140

Val Ser Ser Ile Gly Val Thr Asp Glu Gly Gln Leu Met Asn Val Asn
145                 150                 155                 160

Ala Asp Gln Ala Ala Thr Ala Leu Ala Ala Thr Leu Gly Ala Asp Leu
             165                 170                 175

Ile Leu Leu Ser Asp Val Ser Gly Ile Leu Asp Gly Lys Gly Gln Arg
             180                 185                 190

Ile Ala Glu Met Thr Ala Ala Lys Ala Glu Gln Leu Ile Glu Gln Gly
             195                 200                 205

Ile Ile Thr Asp Gly Met Ile Val Lys Val Asn Ala Ala Leu Asp Ala
     210                 215                 220

Ala Arg Thr Leu Gly Arg Pro Val Asp Ile Ala Ser Trp Arg His Ala
225                 230                 235                 240

Glu Gln Leu Pro Ala Leu Phe Asn Gly Met Pro Met Gly Thr Arg Ile
             245                 250                 255

Leu Ala
```